United States Patent
Torigoe et al.

(10) Patent No.: US 12,018,405 B2
(45) Date of Patent: Jun. 25, 2024

(54) PROTEIN FIBER CRIMPING METHOD, PROTEIN FIBER PRODUCTION METHOD, PROTEIN FIBERS, SPUN YARN, AND TEXTILE PRODUCT

(71) Applicants: SHIMA SEIKI MFG., LTD., Wakayama (JP); SPIBER INC., Tsuruoka (JP)

(72) Inventors: Shozo Torigoe, Wakayama (JP); Seiji Shimoda, Wakayama (JP); Akihiko Ozeki, Tsuruoka (JP)

(73) Assignees: SHIMA SEIKI MFG., LTD., Wakayama (JP); SPIBER INC, Yamagata (JP)

( * ) Notice: Subject to any disclaimer, the term of this patent is extended or adjusted under 35 U.S.C. 154(b) by 886 days.

(21) Appl. No.: 16/982,612

(22) PCT Filed: Mar. 20, 2019

(86) PCT No.: PCT/JP2019/011807
§ 371 (c)(1),
(2) Date: Sep. 21, 2020

(87) PCT Pub. No.: WO2019/182040
PCT Pub. Date: Sep. 26, 2019

(65) Prior Publication Data
US 2021/0017672 A1  Jan. 21, 2021

(30) Foreign Application Priority Data

Mar. 22, 2018  (JP) .................................. 2018-053915

(51) Int. Cl.
| | | |
|---|---|---|
| D01F 4/02 | (2006.01) | |
| C07K 14/435 | (2006.01) | |
| D02G 1/00 | (2006.01) | |
| D06M 15/15 | (2006.01) | |
| D06M 101/12 | (2006.01) | |

(52) U.S. Cl.
CPC .......... *D01F 4/02* (2013.01); *C07K 14/43518* (2013.01); *D02G 1/00* (2013.01); *D06M 15/15* (2013.01); *D06M 2101/12* (2013.01)

(58) Field of Classification Search
CPC ...... D01F 4/02; C07K 14/43518; D92G 1/00; D06M 15/15; D06M 2101/12
See application file for complete search history.

(56) References Cited

U.S. PATENT DOCUMENTS

| | | | | |
|---|---|---|---|---|
| 5,679,329 A | * | 10/1997 | Dupuis | .................... A61Q 5/06 424/47 |
| 2014/0058066 A1 | * | 2/2014 | Sekiyama | ................ D01D 5/16 530/353 |
| 2019/0135881 A1 | | 5/2019 | Morita et al. | |

FOREIGN PATENT DOCUMENTS

| | | | | |
|---|---|---|---|---|
| EP | 3 346 052 A1 | | 7/2018 | |
| JP | 54-30955 A | | 3/1979 | |
| JP | 58-039934 | * | 3/1979 | |
| JP | 62-62990 A | | 3/1987 | |
| JP | 63-249780 | * | 4/1987 | |
| JP | 63-249780 A | | 10/1988 | |
| JP | 2014-129639 A | | 7/2014 | |
| WO | WO 2017038814 | * | 3/2017 | ............ D06M 15/15 |
| WO | 2019/066006 A1 | | 4/2019 | |

OTHER PUBLICATIONS

Official Communication issued in International Patent Application No. PCT/JP2019/011807, mailed on May 21, 2019.
Teulé et al., "A protocol for the production of recombinant spider silk-like proteins for artificial fiber spinning", NIH Public Access Author Manuscript, Nat Protoc. 2009 ; 4(3): 341-355. doi:10.1038/nprot.2008.250, Aug. 4, 2009, pp. 1-32.
Xia et al., "Native-sized recombinant spider silk protein produced in metabolically engineered *Escherichia coli* results in a strong fiber", PNAS, vol. 107, No. 32, Aug. 10, 2010, pp. 14059-14063.
Hatae et al., "Construction of Novel Protein Fiber Consisted of Repeated Motifes from Spider Dragline Silk", Bio Industry, vol. 22, No. 10, 2005, pp. 48-53.

* cited by examiner

*Primary Examiner* — Amina S Khan
(74) *Attorney, Agent, or Firm* — Keating & Bennett, LLP

(57) ABSTRACT

A protein fiber having a crimp property, such that the protein fiber crimps in response to a stimulus, is immersed in a solution of protein having a different composition from the protein fiber. The protein fiber treated with the different protein composition is infiltrated into the protein and the protein fiber is made to crimp.

9 Claims, 5 Drawing Sheets

Specification includes a Sequence Listing.

PROTEIN FIBER CRIMPING METHOD, PROTEIN FIBER PRODUCTION METHOD, PROTEIN FIBERS, SPUN YARN, AND TEXTILE PRODUCT

FIELD OF THE INVENTION

The present invention relates to crimp of protein fiber.

BACKGROUND ART

Patent Document 1 (JP2014-129639) discloses artificial protein fiber similar to spider yarn. Patent Document 2 (WO2017-038814) discloses to dip yarn such as sheep wool and cashmere in an aqueous solution of hydrolyzed keratin resultant from feather.

PRIOR ART DOCUMENTS

Patent Documents

Patent Document 1: JP2014-129639
Patent Document 2: WO2017-038814

SUMMARY OF THE INVENTION

Problem to be Solved by the Invention

Artificial protein fiber does not have scales on the surface, while animal fiber such as sheep wool has. In addition, artificial protein fiber has basically a flat surface without bends and is not crimped. Furthermore, it can not be crimped by applying stress under a heated condition, while polyamide fiber can. These facts also apply to reclaimed protein fiber such as casein-protein fiber and semi-synthesized protein fiber such as Chinon.

Textile products made of fiber without crimp have a problem in their texture; in particular, they have not sufficient bulky touch. Further, textile products made of fiber without crimp nor scales can not be fulled. Here, fulling means a process applying force to textile products and entangling the fiber with each other by colliding the textile products immersed in water to walls and so on of the vessel. Textile products contract in fulling.

The objects of the invention are:
to provide a new method for crimping protein fiber or its spun yarn and also to provide a new production method of crimped protein fiber;
to provide a new fulling method for the textile products made of said protein fiber or said spun yarn; and
to provide crimped protein fiber, crimped spun yarn, and textile products made of said protein fiber or said spun yarn and fulled.

Means for Solving the Problem

According to a crimping method of the invention, protein fiber having crimp property such that the protein fiber crimps in response to a stimulus is immersed in a solution of protein having a different composition from the protein fiber, said protein having a different composition is infiltrated into said protein fiber, and said protein fiber is made crimped.

According to a production method of protein fiber of the invention, protein fiber having crimp property such that the protein fiber crimps in response to a stimulus is immersed in a solution of protein having a different composition from the protein fiber, said protein having a different composition is infiltrated into said protein fiber, and said protein fiber is made crimped.

A protein fiber according to the invention comprises: a mother fiber (mother protein fiber) having crimp property such that the protein fiber crimps in response to a stimulus; and a heterogeneous protein having a different composition from said mother fiber infiltrated in the inside of said mother protein fiber, and the protein fiber is crimped.

A spun yarn according to the invention comprises twisted plural staples of the above protein fiber.

A textile product according to the invention comprises the above protein fiber or the above spun yarn.

Preferably, said protein fiber (mother protein fiber) is made of artificial protein.

More preferably, the artificial protein is artificial spider silk protein.

Preferably, the staples of filaments of said protein fiber are immersed in said solution of protein.

More preferably, the spun yarn made of said staples twisted together is immersed in said solution of protein.

Preferably, a textile product made of said spun yarn is immersed in said solution of protein, said staples in the textile product are made crimped, and the textile product is fulled.

Preferably, the textile product is immersed in said solution of protein under a condition that impact is not applied to said textile product.

Preferably, the solution of protein is an aqueous solution of hydrolyzed keratin.

Preferably, the number averaged molecular weight of said hydrolyzed keratin is not less than 500 and not more than 5000.

Preferably, the concentration of said hydrolyzed keratin before immersing said textile product is not less than 0.1 mass % and not more than 2 mass % and immersing period of said textile product is not less than 5 minutes and not more than 120 minutes.

Preferably, the aqueous solution of hydrolyzed keratin is at a temperature range of 30 degree Celsius to 60 degree Celsius.

As shown in FIGS. 4 and 7, When the protein having a different composition infiltrates into the inside of mother protein fiber, the mother protein fiber crimps. When this protein fiber is made into spun yarn, the spun yarn is bulky and has improved texture. Here, the phenomenon that the protein fiber crimps in response to a stimulus indicates the crimp property to become crimped due to stimulus such as contact with water and so on. The stimulus is not limited to water but includes contact with other solvents or a cross-linking agent, heating, irradiation, and so on. For example, instead of water, aqueous solvents may be used. When crimp is formed by pressing or thermal setting, the staples are drawn during the spinning process, and therefore, sometimes crimp becomes weakened. However, when the protein having a different composition is infiltrated inside of the mother protein fiber, crimp is regenerated.

Preferably, the protein fiber is made of artificial protein whose amino-acid domain sequence is modified (for example, up to 10% of the original sequence) from that of natural protein. The artificial protein is preferably an artificial spider silk protein. The protein fiber may be semi-synthesized protein, such as ProMix or Chinon, or reclaimed protein, such as casein protein, peanut protein, corn protein, or soybean protein. Further, the protein fiber may comprise one kind of protein or plural kinds of protein. The protein fiber may include both an artificial protein fiber and wool or silk fiber.

Protein fibers other than animal hairs such as sheep wool do not have scales on their surface and naturally are not crimped. However, when staples of protein fiber are immersed in a solution of the protein having a different composition to infiltrate the protein into the mother protein fiber, crimp becomes conspicuous and the bulky feel of the spun yarn is enhanced.

When textile products made of spun yarn are immersed in said solution of the protein, the staples are crimped and the gaps between the spun yarn are decreased to make the products fulled (FIGS. 4 and 7). Here, the textile products include fabrics themselves, such as knitted fabrics, woven fabrics, unwoven fabrics, apparel products, such as clothes, handkerchieves, towels, curtains, table-clothes, and industrial products such as car sheets.

The crimp of staples increases the friction between spun yarn and decreases the gaps between the spun yarn so that fulling becomes possible. The inventors have confirmed that knitted fabrics made of artificial spider silk protein can not be fulled enough by regular fulling methods (FIGS. 5 and 8).

Preferably, the textile products are immersed in the solution of protein under the condition that no impacts are applied to the textile products, for example, under the condition that impacts due to collision to he wall of the vessel of the protein solution. Preferably, the solution is stirred or circulated to help the solution infiltrate. According to the invention, textile products are fulled by the contact with the protein solution not by the outer force applied to the textile products. Therefore, fine textile products can be fulled without damage.

Preferably, the solution of protein is an aqueous solution of hydrolyzed keratin. The hydrolyzed keratin affords better texture than hydrolyzed silk and so on, after the treatment. In particular, hydrolyzed keratin derived from feather is preferable. It is important to use low molecular weight hydrolyzed keratin, and the number averaged molecular weight is preferably down to 500 and up to 5000, in particular, down to 500 and up to 3000. The small molecular number helps the keratin infiltrate into the staples.

The keratin concentration of the aqueous solution before immersing the textile products is preferably down to 0.1 mass % and up to 2 mass %, and the immersing period is preferably down to 5 minutes and up to 120 minutes. The inventors have confirmed that within the above ranges the staples are crimped to improve the texture of the spun yarn and the textile products are fulled. The temperature of the hydrolyzed keratin aqueous solution is preferably down to 30 degree Celsius and up to 60 degree Celsius. Below 30 degree Celsius, the generation of crimp is slow, and above 60 degree Celsius, the immersed textile products become hard to decrease the texture.

The spun yarn according to the invention comprises or consists of plural twisted staples that are cut from protein fiber having a crimping character to crimp in response to stimulus, the protein having a different composition from that of the protein fiber is infiltrated into the staples, and the staples are crimped. The spun yarn has improved texture due to the crimp.

The condition for the protein fiber is that it has a crimping character to crimp in response to a stimulus, and the protein fiber may be a structural protein fiber or an artificial protein fiber. Preferably, the protein having a different composition from the protein fiber is hydrolyzed keratin.

The invention provides textile products comprising or consisting of the above spun yarn. If the protein is initially infiltrated to raw spun yarn, then the spun yarn is made crimped and the spun yarn is fulled at this stage. If the protein is infiltrated into the textile products, then crimp is generated and the products are fulled.

When carrying out the crimping method and the production method of protein fiber both according to the invention, preferably, the protein fiber is made of artificial protein, and hydrolyzed keratin and so on as the protein having a different composition improves the dyeing affinity of the protein fiber.

Regarding the protein fiber according to the invention, it is preferable that the protein fiber comprises or consists of artificial protein and that its dyeing affinity is improved by the hydrolyzed keratin and so on as the protein having a different composition.

When the protein having a different composition such as hydrolyzed keratin is infiltrated in the inside of artificial protein fiber, the fiber crimps and has improved dyeing affinity due to the protein having a different composition.

The improved dyeing affinity appears as the reduction of dyestuff migration by sweat (migration by sweat), improvement in light resistance or wash resistance, improvement in resistance to friction with surrounding objects (friction resistance), reduction of contamination of the surrounding textile products during dry-cleaning (dry cleaning contamination), and so on.

Particularly preferably, the protein having a different composition is hydrolyzed keratin, and said protein fiber is immersed in the aqueous solution of hydrolyzed keratin for down to 40 minutes and up to 80 minutes. When artificial protein fiber is immersed in the solution of hydrolyzed keratin, a peak of keratin absorption appears near about 60 minutes of immersing period. Therefore, the immersing period of 40 to 80 minutes near about 60 minutes affords infiltration of a large quantity of keratin into the artificial protein fiber.

FEATURES FOR CARRYING OUT THE INVENTION

Figure 1:
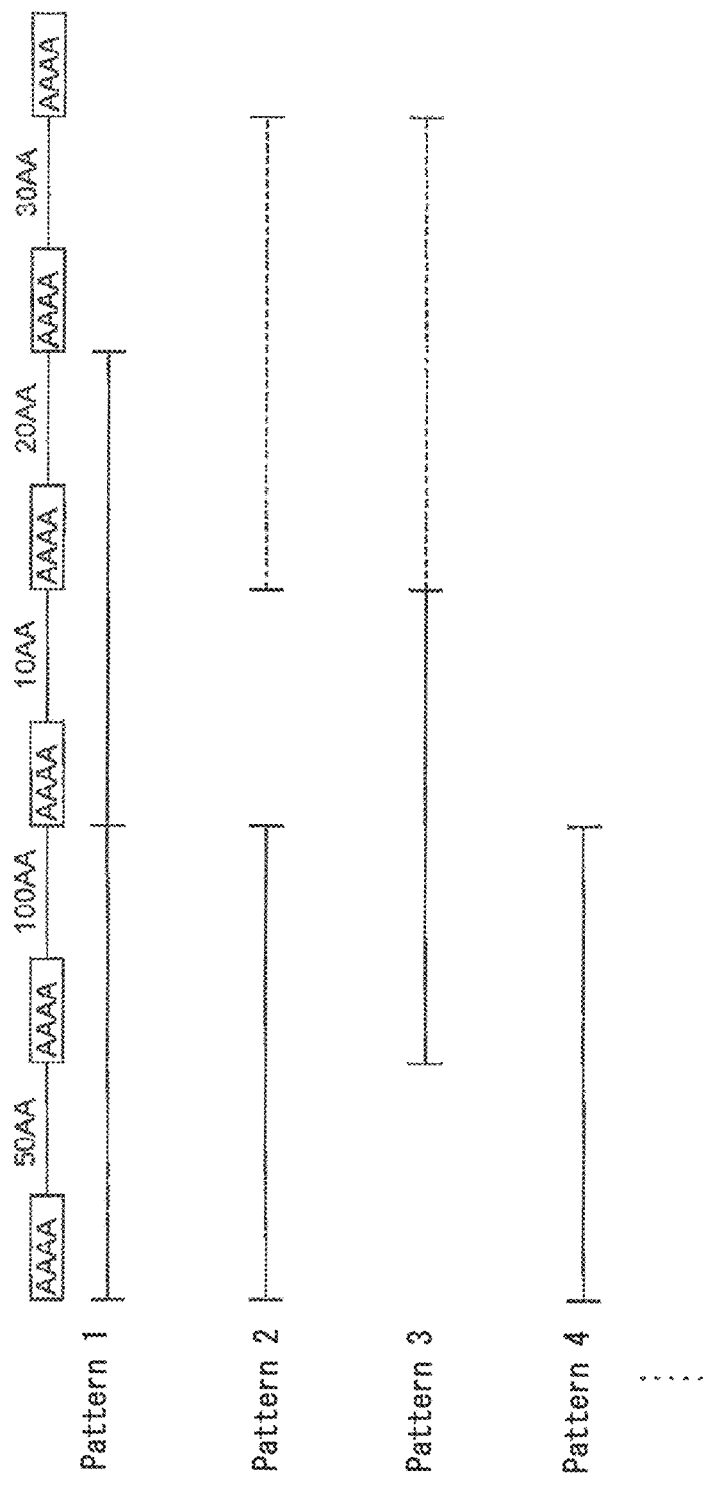
FIG. 1: A schematic view of an example of a domain sequence of a modified fibroin.

The best embodiment for carrying out the invention will be described.

<Protein>

The protein constituting the protein fiber may be a structural protein, and the structural protein may be fibroin. The fibroin may be natural fibroin or modified fibroin (artificial fibroin). The modified fibroin may be spider silk fibroin, and the modified spider silk fibroin may be one with artificially introduced hydrophobic amino-acid residues or one with artificially introduced hydrophilic amino-acid residues.

<Modified Fibroin>

The modified fibroin is a protein including a domain sequence represented by Formula 1: $[(A)_n$ motif-REP$]_m$ or Formula 2: $[(A)_n$ motif-REP$]_m$-$(A)_n$ motif. In the modified fibroin, an amino acid sequence (N-terminal sequence and C-terminal sequence) may be further added to either or both of the N-terminal side and the C-terminal side of the domain sequence. The N-terminal sequence and the C-terminal sequence, although not limited thereto, are typically regions that do not have repetitions of amino acid motifs characteristic of fibroin and consist of amino acids of about 100 residues.

The term "modified fibroin" as used herein means an artificially produced fibroin (an artificial fibroin). The domain sequence of modified fibroin may be different from the amino acid sequence of naturally occurring fibroin or the same to the amino acid sequence of naturally occurring fibroin. The "naturally occurring fibroin" referred to in the present specification is also a protein including a domain sequence represented by Formula 1: $[(A)_n$ motif-REP]m or Formula 2: $[(A)_n$ motif-REP$]_m$-$(A)_n$ motif.

The "modified fibroin" has the amino acid sequence specified in the present specification and may have an amino acid sequence of naturally occurring fibroin as are or have an amino acid sequence that has been modified based on naturally occurring fibroin (for example, a fibroin whose amino acid sequence has been modified by altering a cloned gene sequence of naturally occurring fibroin). It may be a fibroin artificially designed and synthesized independently of naturally occurring fibroin (for example, a fibroin having a desired amino acid sequence by chemical synthesis of a nucleic acid encoding the designed amino acid sequence).

The term "domain sequence" as used herein refers to an amino acid sequence which produces a crystalline region (typically, equivalent to $(A)_n$ motif in the amino acid sequence) and an amorphous region (typically, equivalent to REP in the amino acid sequence) peculiar to spider silk fibroin and means an amino acid sequence represented by Formula 1: $[(A)_n$ motif-REP$]_m$ or Formula 2: $[(A)_n$ motif-REP$]_m$-$(A)_n$ motif. Here, the $(A)_n$ motif represents an amino acid sequence mainly made of alanine residues, and n is 2 to 27. The integer n may be 2 to 20, 4 to 27, 4 to 20, 8 to 20, 10 to 20, 4 to 16, 8 to 16, or 10 to 16. The ratio of alanine residues is 40% or more in the total number of amino acid residues in the $(A)_n$ motif, preferably 60% or more, 70% or more, 80% or more, 83% or more, 85% or more, 86% or more, 90% or more, 95% or more, or 100% (which means that the $(A)_n$ motif consists of only alanine residues). At least seven of the plural $(A)_n$ motifs in the domain sequence may consist of alanine residues. REP represents an amino acid sequence consisting of 2 to 200 amino acid residues. m represents an integer of 10 to 200. The integer m is 2 to 300 and may be 10 to 300. represents. The plurality of $(A)_n$ motifs may be the same amino acid sequence or different amino acid sequences. The plurality of REPs may be the same amino acid sequences or different amino acid sequences.

The modified fibroin may be produced by transcribing the amino acid sequence corresponding to substitution, deletion, insertion, and/or addition of, for example, one or more amino acid residues to the gene sequence of cloned and naturally occurring fibroin. The substitution, deletion, insertion, and/or addition of amino acid residues may be carried out by methods well known to those skilled in the art, such as site-directed mutagenesis. Specifically, the modifications may be carried out by a method described in literature such as Nucleic Acid Res. 10, 6487 (1982), and Methods in Enzymology, 100, 448 (1983).

Naturally occurring fibroin is a protein including a domain sequence represented by Formula 1: $[(A)_n$ motif-REP$]_m$ or Formula 2: $[(A)_n$ motif-REP$]_m$-$(A)_n$ motif, specifically, for example, a fibroin produced by insects or spiders.

Examples of the fibroin produced by insects include silk proteins produced by silkworms such as *Bombyx mori, Bombyx mandarina, Antheraea yamamai, Anteraea pernyi, Eriogyna pyretorum, Pilosamia Cynthia ricini, Sarnia cynthia, Caligura japonica, Antheraea mylitta,* and *Antheraea assama*; and hornet silk proteins discharged by larvae of *Vespa simillima xanthoptera*.

A more specific example of the fibroin produced by insects includes a silkworm fibroin L chain (GenBank Accession No. M76430 (base sequence), AAA27840.1 (amino acid sequence)).

Examples of the fibroin produced by spiders include spider silk proteins produced by spiders belonging to the genus *Araneus* such as *Araneus ventricosus, Araneus diadematus, Araneus pinguis, Araneus pentagrammicus* and *Araneus nojimai*, spiders belonging to the genus *Neoscona* such as *Neoscona scylla, Neoscona nautica, Neoscona adianta* and *Neoscona scylloides*, spiders belonging to the genus *Pronus* such as *Pronous minutes*, spiders belonging to the genus *Cyrtarachne* such as *Cyrtarachne bufo* and *Cyrtarachne inaequalis*, spiders belonging to the genus *Gasteracantha* such as *Gasteracantha kuhli* and *Gasteracantha mammosa*, spiders belonging to the genus *Ordgarius* such as *Ordgarius hobsoni* and *Ordgarius sexspinosus*, spiders belonging to the genus *Argiope* such as *Argiope amoena, Argiope minuta* and *Argiope bruennich*, spiders belonging to the genus *Arachnura* such as *Arachnura logio*, spiders belonging to the genus *Acusilas* such as *Acusilas coccineus*, spiders belonging to the genus *Cytophora* such as *Cyrtophora moluccensis, Cyrtophora exanthematica* and *Cyrtophora unicolor*, spiders belonging to the genus *Poltys* such as *Poltys illepidus*, spiders belonging to the genus *Cyclosa* such as *Cyclosa octotuberculata, Cyclosa sedeculata, Cyclosa vallata* and *Cyclosa atrata*, and spiders belonging to the genus *Chorizopes* such as *Chorizopes nipponicus*; and spider silk proteins produced by spiders belonging to the genus *Tetragnatha* such as *Tetragnatha praedonia, Tetragnatha maxillosa, Tetragnatha extensa* and *Tetragnatha squamata*, spiders belonging to the genus *Leucauge* such as *Leucauge magnifica, Leucauge blanda* and *Leucauge subblanda*, spiders belonging to the genus *Nephila* such as *Nephila clavata* and *Nephila pilipes*, spiders belonging to the genus *Menosira* such as *Menosira omata*, spiders belonging to the genus *Dyschiriognatha* such as *Dyschiriognatha tenera*, spiders belonging to the genus *Latrodectus* such as *Latrodectus mactans, Latrodectus hasseltii, Latrodectus geometricus* and *Latrodectus tredecimguttatus*, and spiders belonging to the family Tetragnathidae such as spiders belonging to the genus *Euprosthenops*. Examples of spider silk proteins include traction yarn proteins such as MaSp (MaSp1 and MaSp2) and ADF (ADF3 and ADF4), and MiSp (MiSp1 and MiSp2).

More specific examples of the fibroin produced by spiders include fibroin-3 (adf-3) [derived from *Araneus diadematus*] (GenBank Accession Number AAC47010 (amino acid sequence), U47855 (base sequence)), fibroin-4 (adf-4) [derived from *Araneus diadematus*] (GenBank Accession Number AAC47011 (amino acid sequence), U47856 (base sequence)), dragline silk protein spidroin 1 [derived from *Nephila clavipes*] (GenBank Accession Number AAC04504 (amino acid sequence), U37520 (base sequence)), major angullate spidroin 1 [derived from *Latrodectus hesperus*] (GenBank Accession Number ABR68856 (amino acid sequence), EF595246 (base sequence)), dragline silk protein spidroin 2 [derived from *Nephila clavata*] (GenBank Accession Number AAL32472 (amino acid sequence), AF441245 (base sequence)), major anpullate spidroin 1 [derived from *Euprosthenops australis*] (GenBank Accession Number CAJ00428 (amino acid sequence), AJ973155 (base sequence)) and major ampullate spidroin 2 [*Euprosthenops australis*] (GenBank Accession Number CAM432249.1 (amino acid sequence), AM490169 (base sequence)), minor ampullate silk protein 1 [*Nephila clavipes*] (GenBank Accession Number AAC14589.1 (amino acid sequence), minor ampullate silk protein 2 [*Nephila clavipes*] (GenBank Accession Number AAC14591.1 (amino acid sequence)), and minor ampullate spidroin-like protein [*Nephilengys cruentata*] (GenBank Accession Number ABR37278.1 (amino acid sequence)).

As a further specified example of naturally occurring fibroin, fibroin whose sequence information is registered in NCBI GenBank may be mentioned. For example, sequences thereof may be confirmed by extracting sequences in which spidroin, ampullate, fibroin, "silk and polypeptide", or "silk and protein" is described as a keyword in DEFINITION among sequences containing INV as DIVISION among sequence information registered in NCBI GenBank, sequences in which a specific character string of products is described from CDS, or sequences in which a specific character string is described from SOURCE to TISSUE TYPE.

The modified fibroin may be a modified silk fibroin (a modified silk protein obtained by modifying an amino acid sequence of a silk protein produced by silkworm) and a modified spider silk fibroin (a modified spider silk protein obtained by modifying an amino acid sequence of a spider silk protein produced by spiders). The modified fibroin is preferably a modified spider silk fibroin.

Specific examples of the modified fibroin include: a modified fibroin derived from a large sphincter bookmark silk protein produced in a major ampullate of a spider; a modified fibroin having a domain sequence with a reduced content of glycine residue; and a modified fibroin having a domain sequence with a reduced content of $(A)_n$ motif.

The modified fibroin derived from a large sphincter bookmark silk protein produced in a major ampullate of spider includes a protein including a domain sequence represented by Formula 1: $[(A)_n$ motif-REP$]_m$. In the modified fibroin derived from a large sphincter bookmark silk protein produced in a major ampullate of spider, the number of amino acid residues of $(A)_n$ motif is preferably an integer of 3 to 20, more preferably an integer of 4 to 20, still more preferably an integer of 8 to 20, even more preferably an integer of 10 to 20, even further more preferably an integer of 4 to 16, particularly preferably an integer of 8 to 16, and most preferably an integer of 10 to 16. In the modified fibroin derived from a large sphincter bookmark silk protein produced in a major ampullate of spider, the number of amino acid residues constituting REP in Formula 1 is preferably 10 to 200 residues, more preferably 10 to 150 residues, and still more preferably 20 to 100 residues, and even more preferably 20 to 75 residues. In the modified fibroin derived from a large sphincter bookmark silk protein produced in a major ampullate of spider, the total number of glycine residues, serine residues, and alanine residues contained in the amino acid sequence represented by Formula 1: $[(A)$ n motif-REP$]_m$ is preferably 40% or more, more preferably 60% or more, and still more preferably 70% or more with respect to the total number of amino acid residues.

The modified fibroin derived from a large sphincter bookmark silk protein produced in a major ampullate of spider may be a polypeptide including an amino acid sequence unit represented by Formula 1: $[(A)n$ motif-REP$]_m$, and including a C-terminal sequence which is the amino acid sequence set forth in any of SEQ ID Nos: 14 to 16 or a C-terminal sequence which is an amino acid sequence having 90% or more homology with the amino acid sequence set forth in any of SEQ ID Nos: 14 to 16.

The amino acid sequence set forth in SEQ ID No. 14 is identical to the amino acid sequence consisting of 50 amino acid residues at the C-terminal of the amino acid sequence of ADF3 (GI: 1263287, NCBI). The amino acid sequence set forth in SEQ ID No. 15 is identical to the amino acid sequence obtained by removing 20 residues from the C-terminal of the amino acid sequence set forth in SEQ ID No. 14. The amino acid sequence set forth in SEQ ID No. 16 is identical to the amino acid sequence obtained by removing 29 residues from the C-terminal of the amino acid sequence set forth in SEQ ID No. 14.

More specific examples of the modified fibroin derived from a large sphincter bookmark silk protein produced in a major ampullate of spider can include a modified fibroin including (1-i) the amino acid sequence set forth in SEQ ID No. 17 (recombinant spider silk protein ADF3KaiLargeNRSH1) and (1-ii) an amino acid sequence having 90% or more sequence identity with the amino acid sequence set forth in SEQ ID No. 17. The sequence identity is preferably 95% or more.

The amino acid sequence set forth in SEQ ID No. 17 is an amino acid sequence obtained by approximately doubling repeating regions from the first repeating region to the 13th repeating region and performing mutation such that translation is terminated at the 1154th amino acid residue in an amino acid sequence obtained by adding the amino acid sequence (SEQ ID No. 18) consisting of a start codon, a His10 tag, and a recognition site for HRV3C protease (human rhinovirus 3C protease) to the N-terminal of ADF3. The C-terminal amino acid sequence of the amino acid sequence set forth in SEQ ID No. 17 is identical to the amino acid sequence set forth in SEQ ID No. 16.

The modified fibroin of (1-i) may consist of the amino acid sequence set forth in SEQ ID No. 17.

The domain sequence of the modified fibroin having a domain sequence with a reduced content of glycine residue has an amino acid sequence with a reduced content of glycine residue, as compared with naturally occurring fibroin. It can be said that the modified fibroin having a domain sequence with a reduced content of glycine residue has an amino acid sequence equivalent to an amino acid sequence in which at least one or a plurality of glycine residues in REP are substituted with other amino acid residues, as compared with naturally occurring fibroin.

The domain sequence of the modified fibroin having a domain sequence with a reduced content of glycine residue may have an amino acid sequence equivalent to an amino acid sequence in which one glycine residue in at least one or the plurality of motif sequences, at least one of which is selected from GGX and GPGXX (where G represents a glycine residue, P represents a proline residue, and X represents an amino acid residue other than glycine) in REP, is substituted with other amino acid residuee, as compared with naturally occurring fibroin.

In the modified fibroin having a domain sequence with a reduced content of glycine residue, the proportion of the motif sequences in which the above-described glycine residue is substituted with other amino acid residue may be 10% or more with respect to the entire motif sequences.

The modified fibroin having a domain sequence with a reduced content of glycine residue may include a domain sequence represented by Formula 1: $[(A)\ motif\text{-}REP]_m$ and have an amino acid sequence in which z/w is 30% or more, 40% or more, 50% or more, or 50.9% or more, in a case where the total number of amino acid residues in the amino acid sequence consisting of XGX (where X represents an amino acid residue other than glycine) in all REPs in a sequence excluding the sequence from the $(A)_n$ motif located at the most C-terminal side to the C-terminal of the domain sequence from the domain sequence is set as z, and the total number of amino acid residues in the sequence excluding the sequence from the $(A)_n$ motif located at the most C-terminal side to the C-terminal of the domain sequence from the domain sequence is set as w. The ratio of alanine residues is 83% or more in the total number of amino acid residues in the $(A)_n$ motif, preferably 86% or more, more preferably 90% or more, still more preferably 95% or more, and even still more preferably 100% (which means that the $(A)_n$ motif consists of only alanine residues).

In the modified fibroin having a domain sequence with a reduced content of glycine residue, the content proportion of an amino acid sequence consisting of XGX is preferably increased by substituting one glycine residue in GGX motif with other amino acid residues. In the modified fibroin having a domain sequence with a reduced content of glycine residue, the content proportion of an amino acid sequence consisting of GGX in the domain sequence is preferably 30% or less, more preferably 20% or less, still more preferably 10% or less, even still more preferably 6% or less, still further preferably 4% or less, and particularly preferably 2% or less. The content proportion of an amino acid sequence consisting of GGX in a domain sequence can be calculated by the same method as the method for calculating the content ratio (z/w) of the amino acid sequence consisting of XGX.

The calculation of z/w will be more specifically described. First, in the fibroin (modified fibroin) including a domain sequence represented by Formula 1: $[(A)_n\ motif\text{-}REP]_m$, in the domain sequence, the sequences from the $(A)_n$ motif nearest from the C-terminal to the C-terminal in the domain sequence are removed, and form all the remaining REP, the amino acid sequence consisting of XGX. The total number of amino acid residues constituting XGX is z. For example, when 50 pieces of amino acid sequences consisting of XGX are extracted (without duplication), z is equal to 150=3×50. When X contained in two XGX is present, for example, X in an amino acid sequence of XGXGX (X at the center), the duplication is subtracted (5 amino acid residues in XGXGX). The number w is the total amino acid residues contained in the domain sequence where the sequences from the $(A)_n$ motif nearest from the C-terminal to the C-terminal in the domain sequence are removed. For example, in the domain sequence shown in FIG. 1, w is equal to 230=4+50+4+100+4+10+4+20+4+30 ($(A)_n$ motif nearest to the C-terminal being removed). Then, z is divided by w to calculate z/w (%).

In the modified fibroin having a domain sequence with a reduced content of glycine residue, z/w is preferably 50.9% or more, more preferably 56.1% or more, still more preferably 58.7% or more, even still more preferably 70% or more, and still further preferably 80% or more. The upper limit of z/w is not particularly limited, but it may be 95% or less, for example.

The modified fibroin having a domain sequence with a reduced content of glycine residue can be obtained by, for example, modifying a cloned naturally occurring fibroin gene sequence such that at least a part of a base sequence encoding a glycine residue is substituted with other amino acid residue to encode other amino acid residue. At this time, one glycine residue in GGX motif and GPGXX motif may be selected as the glycine residue to be modified, or may be substituted so that z/w is 50.9% or more. Alternatively, the modified fibroin having a domain sequence with a reduced content of glycine residue according to the present embodiment may also be obtained, for example, by designing an amino acid sequence satisfying the above-described aspect based on the amino acid sequence of naturally occurring fibroin and chemically synthesizing a nucleic acid encoding the designed amino acid sequence. In any case, with respect to the amino acid sequence of naturally occurring fibroin, in addition to the modification equivalent to substitution of glycine residue in REP with other amino acid residue, further modification of amino acid sequence equivalent to substitution, deletion, insertion, and/or addition of one or a plurality of amino acid residues may be carried out.

The other amino acid residue described above is not particularly limited as long as it is an amino acid residue other than glycine residue, but is preferably a hydrophobic amino acid residue such as valine (V) residue, leucine (L) residue, isoleucine (I) residue, methionine (M) residue, proline (P) residue, phenylalanine (F) residue, and tryptophan (W) residue, or a hydrophilic amino acid residues such glutamine (Q) residue, asparagine (N) residue, serine (S) residue, lysine (K) residue, and glutamic acid (E) residue, more preferably valine (V) residue, leucine (L) residue, isoleucine (I) residue, phenylalanine (F) residue, and glutamine (Q) residue, and still more preferably glutamine (Q) residue.

More specific examples of the modified fibroin having a domain sequence with a reduced content of glycine residue can include a modified fibroin including (2-i) the amino acid sequence set forth in SEQ ID Nos. 3, 4, 10, or 12, and (2-ii) an amino acid sequence having 90% or more sequence identity with the amino acid sequence set forth in SEQ ID Nos. 3, 4, 10, or 12.

The modified fibroin of (2-i) will be described. The amino acid sequence set forth in SEQ ID No. 3 is obtained by substituting all GGXs in REP in the amino acid sequence set forth in SEQ ID No. 1 equivalent to naturally occurring fibroin with GQX. The amino acid sequence set forth in SEQ ID No. 4 is obtained by deleting one of every two $(A)_n$ motifs from the N-terminal side to the C-terminal side in the amino acid sequence set forth in SEQ ID No. 3 and further inserting one $[(A)_n\ motif\text{-}REP]$ just before the C-terminal sequence. The amino acid sequence set forth in SEQ ID No. 10 is obtained by inserting two alanine residues at the C-terminal side of each $(A)_n$ motif in the amino acid sequence set forth in SEQ ID No. 4, and further substituting a part of glutamine (Q) residues with serine (S) residues and deleting a part of amino acids on the C-terminal side such that the molecular weight thereof becomes approximately the same as that of SEQ ID No. 4. The amino acid sequence set forth in SEQ ID No. 12 is an amino acid sequence obtained by adding a predetermined hinge sequence and a His tag sequence to the C-terminal of a sequence obtained by repeating a region of 20 domain sequences (where several amino acid residues on the C-terminal side of the region are substituted) present in the amino acid sequence set forth in SEQ ID No. 9 four times.

The value of z/w in the amino acid sequence set forth SEQ ID No. 1 (equivalent to naturally occurring fibroin) is 46.8%. The values of z/w in the amino acid sequence set forth in SEQ ID No. 3, the amino acid sequence set forth in SEQ ID No. 4, the amino acid sequence set forth in SEQ ID No. 10, and the amino acid sequence set forth in SEQ ID No. 12 are respectively 58.7%, 70.1%, 66.1%, and 70.0%. In addition, the values of x/y with a Giza ratio (described later) of 1:1.8 to 11.3 in the amino acid sequences set forth in SEQ ID Nos. 1, 3, 4, 10 and 12 are respectively 15.0%, 15.0%, 93.4%, 92.7%, and 89.8%.

The modified fibroin of (2-i) may consist of the amino acid sequence set forth in SEQ ID Nos. 3, 4, 10, or 12.

The modified fibroin of (2-ii) includes an amino acid sequence having 90% or more sequence identity with the amino acid sequence set forth in SEQ ID Nos. 3, 4, 10, or 12. The modified fibroin of (2-ii) is also a protein including a domain sequence represented by Formula 1: $[(A)_n$ motif-$REP]_m$. The sequence identity is preferably 95% or more.

The modified fibroin of (2-ii) preferably has 90% or more sequence identity with the amino acid sequence set forth in SEQ ID Nos. 3, 4, 10, or 12, and when the total number of amino acid residues in the amino acid sequence consisting of XGX (where X represents an amino acid residue other than glycine) included in REP is referred to as z, and when the total number of amino acid residues in REP in the domain sequence is referred to as w, z/w is preferably 50.9% or more.

The above-described modified fibroin may include a tag sequence at either or both of the N-terminal and C-terminal. This makes it possible to isolate, immobilize, detect, and visualize the modified fibroin.

The tag sequence may be, for example, an affinity tag utilizing specific affinity (binding property, affinity) with another molecule. As a specific example of the affinity tag, a histidine tag (His tag) can be mentioned. The His tag is a short peptide in which about 4 to 10 histidine residues are arranged and has a property of specifically binding to a metal ion such as nickel, so it can be used for isolation of modified fibroin by chelating metal chromatography. A specific example of the tag sequence may include the amino acid sequence set forth in SEQ ID No. 5 (amino acid sequence including a His tag sequence and a hinge sequence).

In addition, a tag sequence such as glutathione-S-transferase (GST) that specifically binds to glutathione or a maltose binding protein (MBP) that specifically binds to maltose can also be used.

Further, an "epitope tag" utilizing an antigen-antibody reaction can also be used. By adding a peptide (epitope) showing antigenicity as a tag sequence, an antibody against the epitope can be bound. Examples of the epitope tag include an HA tag (peptide sequence of hemagglutinin of influenza virus tag), a myc tag, and a FLAG tag. The modified fibroin can easily be purified with high specificity by utilizing an epitope tag.

It is also possible to use a tag sequence which can be cleaved with a specific protease. By treating a protein adsorbed through the tag sequence with protease, it is also possible to recover the modified fibroin cleaved from the tag sequence.

A more specific example of the modified fibroin including a tag sequence may be one including (2-iii) the amino acid sequence set forth in SEQ ID Nos. 8, 9, 11, or 13, or (2-iv) an amino acid sequence having 90% or more sequence identity with the amino acid sequence set forth in SEQ ID Nos. 8, 9, 11, or 13.

The amino acid sequences set forth in SEQ ID Nos. 6, 7, 8, 9, 11, and 13 are respectively amino acid sequences obtained by adding the amino acid sequence (including a His tag sequence and a hinge sequence) set forth in SEQ ID No. 5 to the N-terminal of the amino acid sequences set forth in SEQ ID Nos. 1, 2, 3, 4, 10 and 12.

The modified fibroin of (2-iii) may consist of the amino acid sequence set forth in SEQ ID Nos. 8, 9, 11, or 13.

The modified fibroin of (2-iv) includes an amino acid sequence having 90% or more sequence identity with the amino acid sequence set forth in SEQ ID Nos. 8, 9, 11, or 13. The modified fibroin of (2-iv) is also a protein including a domain sequence represented by Formula 1: $[(A)_n$ motif-$REP]_m$. The sequence identity is preferably 95% or more.

The modified fibroin of (2-iv) preferably has 90% or more sequence identity with the amino acid sequence set forth in SEQ ID Nos. 8, 9, 11, or 13, and in when the total number of amino acid residues in the amino acid sequence consisting of XGX (where X represents an amino acid residue other than glycine) included in REP is referred to as z, and when the total number of amino acid residues in REP in the domain sequence is referred to as w, z/w is preferably 50.9% or more.

The above-described modified fibroin may include a secretory signal for releasing the protein produced in the recombinant protein production system to the outside of a host. The sequence of the secretory signal can be appropriately set depending on the type of the host.

The domain sequence of the modified fibroin having a reduced $(A)_n$ motif content has an amino acid sequence in which the content of $(A)_1$, motif is reduced, as compared with naturally occurring fibroin. It can be said that the domain sequence of the above-described modified fibroin has an amino acid sequence equivalent to an amino acid sequence in which at least one or a plurality of (A), motifs are deleted, as compared with naturally occurring fibroin.

The modified fibroin having a reduced $(A)_n$ motif content may have an amino acid sequence equivalent to an amino acid sequence in which 10% to 40% of (A) motifs is deleted from naturally occurring fibroin.

The domain sequence of the modified fibroin having a reduced $(A)_n$ motif content may have an amino acid sequence equivalent to an amino acid sequence obtained by deleting one of every one to three $(A)_n$ motifs at least from the N-terminal side to the C-terminal side, as compared with naturally occurring fibroin.

The domain sequence of the modified fibroin having a reduced $(A)_n$ motif content may have an amino acid sequence equivalent to an amino acid sequence obtained by repeating deletion of at least two consecutive $(A)_n$ motifs and deletion of one $(A)_n$ motif in this order from the N-terminal side to the C-terminal side, as compared with naturally occurring fibroin.

The domain sequence of the modified fibroin having a reduced $(A)_n$ motif content may have an amino acid sequence equivalent to an amino acid sequence obtained by deleting one of every two $(A)_n$ motifs at least from the N-terminal side to the C-terminal side.

The modified fibroin having a reduced $(A)_n$ motif content may include a domain sequence represented by Formula 1: $[(A)_n \text{ motif-REP}]_m$, and have an amino acid sequence when the number of amino acid residues of two $[(A)_n \text{ motif-REP}]$ units adjacent to each other is sequentially compared from the N-terminal side to the C-terminal side, and when the number of amino acid residues of REP having a small number of amino acid residues is set as 1, the maximum total value of the number of amino acid residues of two $[(A)_n \text{ motif-REP}]$ units adjacent to each other, in which the ratio (Giza ratio) of the number of amino acid residues of the other REP is 1.8 to 11.3, is set as x, and the total number of amino acid residues in the domain sequence is set as y, x/y may be 20% or more, 30% or more, 40% or more, or 50% or more. The ratio of alanine residues is 83% or more in the total number of amino acid residues in the (A) motif, preferably 86% or more, more preferably 90% or more, still more preferably 95% or more, and even still more preferably 100% (which means that the $(A)_n$ motif consists of only alanine residues).

The calculation of x/y will be described more specifically with reference to FIG. 1. FIG. 1 indicates the domain sequence of the modified fibroin where the N-terminal sequence and C-terminal sequence are removed. The above domain sequence has a sequence, from the N-terminal (from the left), comprising: $(A)_n$ motif—the first REP (50 amino acid residues)—$(A)_n$ motif—the second REP (100 amino acid residues)—$(A)_n$ motif—the third REP (10 amino acid residues)—$(A)_n$ motif—the fourth REP (20 amino acid residues)—$(A)_n$ motif—the fifth REP (30 amino acid residues)—$(A)_n$ motif.

The adjacent two $[(A)_n$ motif—REP] units are sequentially selected from the N-terminal side to the C-terminal side without duplication. Here, non-selected $[(A)_n$ motif—REP] unit may be present. FIG. 1 indicates: pattern 1 (comparison of the first REP and the second REP and of the third REP and the fourth REP); pattern 2 (comparison of the first REP and the second REP and of the fourth REP and the fifth REP); pattern 3 (comparison of the second REP and the third REP and of the fourth REP and the fifth REP); and pattern 4 (comparison of the first REP and the second REP). Other selection methods may be used.

Then, with respect to selected adjacent two $[(A)_n$ motif—REP] units, the numbers of the amino acid residues in the REPs are compared with. In the comparison. The amino acid residue numbers in the REP having less amino acid residues is set 1, and the relative amino acid residue numbers in the other REP is calculated. For example, when the first REP has 50 amino acid residues and the second REP has 100 amino acid residues, then, the ratio is equal to 2=100/50. Similarly, when the fourth REP has 20 amino acid residues and the fifth REP has 30 amino acid residues, then, the ratio is equal to 1.5=30/20.

In FIG. 1, the solid lines the combination of units of $[(A)_n$ motif—REP] having the relative amino acid residue ratio of 1.8 to 11.3. In the following, the above ratio will be referred to as Giza ratio. The combinations of unit having Giza ratio smaller than 1.8 or larger than 11.3 are indicated by broken lines.

For each pattern, all the amino acid residue numbers in the adjacent two $[(A)_n$ motif—REP] units indicated by the solid lines are summed up (not only for the REPs but also amino acid residues in $(A)_n$ motifs) to the total value. The greatest total value is set x. In FIG. 1, the spattern 1 has the greatest value.

Then, x is divided by y, namely the total amino acid residue numbers in the domain sequence, to calculate x/y (%).

In the modified fibroin having a reduced $(A)_n$ motif content, x/y is preferably 50% or more, more preferably 60% or more, still more preferably 65% or more, even still more preferably 70% or more, still further preferably 75% or more, and particularly preferably 80% or more. The upper limit of x/y is not particularly limited, but it may be 100% or less, for example. In a case where the Giza ratio is 1:1.9 to 11.3, x/y is preferably 89.6% or more. In a case where the Giza ratio is 1:1.8 to 3.4, x/y is more preferably 77.1% or more. In a case where the Giza ratio is 1:1.9 to 8.4, x/y is still more preferably 75.9% or more. In a case where the Giza ratio is 1:1.9 to 4.1, x/y is even still more preferably 64.2% or more.

In a case where the modified fibroin having a reduced $(A)_n$ motif content is a modified fibroin in which at least seven of multiple $(A)_n$ motifs present in the domain sequence are composed of only alanine residues, x/y is preferably 46.4% or more, more preferably 50% or more, still more preferably 55% or more, even still more preferably 60% or more, still further preferably 70% or more, and particularly preferably 80% or more. The upper limit of x/y is not particularly limited as long as it is 100% or less.

The modified fibroin having a reduced $(A)_n$ motif content, for example, can be obtained by deleting one or plural sequences encoding $(A)_n$ motif from a cloned gene sequence of naturally occurring fibroin such that x/y is 64.2% or more. Alternatively, the modified fibroin may also be obtained, for example, by designing an amino acid sequence equivalent to an amino acid sequence obtained by deleting one or a plurality $(A)_n$ motifs such that x/y is 64.2% or more based on the amino acid sequence of naturally occurring fibroin and chemically synthesizing a nucleic acid encoding the designed amino acid sequence. In any case, with respect to the amino acid sequence of naturally occurring fibroin, in addition to the modification equivalent to deletion of (A) motif, further modification of amino acid sequence equivalent to substitution, deletion, insertion and/or addition of one or a plurality of amino acid residues may be carried out.

More specific examples of the modified fibroin having a reduced $(A)_n$ motif content can include a modified fibroin including (3-i) the amino acid sequence set forth in SEQ ID Nos. 2, 4, 10, or 12, and (3-ii) an amino acid sequence having 90% or more sequence identity with the amino acid sequence set forth in SEQ ID Nos. 2, 4, 10, or 12.

The modified fibroin of (3-i) will be described. The amino acid sequence set forth in SEQ ID No. 2 is obtained by deleting one of every two $(A)_n$ motifs from the N-terminal side to the C-terminal side in the amino acid sequence set forth in SEQ ID No. 1 equivalent to naturally occurring fibroin and by further inserting one $[(A)$ motif-REP] just before the C-terminal sequence. The amino acid sequence set forth in SEQ ID No. 4 is obtained by substituting GQX for all GGX in the REPs in the amino acid sequence set forth in SEQ ID No. 4. The amino acid sequence set forth in SEQ ID No. 10 is obtained by inserting two alanine residues into the C-terminal of each $(A)_n$ motif in the amino acid sequence set forth in SEQ ID No. 4, substituting Serine residues (S) for a part of glutamine (Q) residues, and removing a part of amino acids at the N-terminal so that the molecular weight becomes nearly equal to that of SEQ ID No. 4. The amino acid sequence set forth in SEQ ID No. 12 comprises a sequence where a fourth repetition of a region of 20 domain sequences (several amino acid residues being added to the C-terminal) present in the amino acid sequence in SEQ ID No. 9 and a His tag is added to the C-terminal.

The value of x/y with a Giza ratio of 1:1.8 to 11.3 in the amino acid sequence set forth in SEQ ID No. 1 (equivalent to naturally occurring fibroin) is 15.0%. Both the value of x/y in the amino acid sequence set forth in SEQ ID No. 2 and the value of x/y in the amino acid sequence set forth in SEQ ID No. 4 are 93.4%. The value of x/y in the amino acid sequence set forth in SEQ ID No. 10 is 92.7%. The value of x/y in the amino acid sequence set forth in SEQ ID No. 12 is 89.3%. The values of z/w in the amino acid sequences set forth in SEQ ID Nos. 1, 2, 4, 10, and 12 are respectively 46.8%, 56.2%, 70.1%, 66.1%, and 70.0%.

The modified fibroin of (3-i) may consist of the amino acid sequence set forth in SEQ ID Nos. 2, 4, 10, or 12.

The modified fibroin of (3-ii) includes an amino acid sequence having 90% or more sequence identity with the amino acid sequence set forth in SEQ ID Nos. 2, 4, 10, or 12. The modified fibroin of (340 is also a protein including a domain sequence represented by Formula 1: $[(A)_n$ motif-REP$]_m$. The sequence identity is preferably 95% or more.

The modified fibroin of (3-ii) preferably has 90% or more sequence identity with the amino acid sequence set forth in SEQ ID Nos. 2, 4, 10, or 12, and when the number of amino acid residues of two $[(A)_n$ motif-REP] units adjacent to each other is sequentially compared from the N-terminal side to the C-terminal side, and when the number of amino acid residues of one REP having a small number of amino acid residues is set as 1, the maximum total value of the number of amino acid residues of two $[(A)_n$ motif-REP] units adjacent to each other, in which the ratio (1:1.8 to 11.3 as a Giza ratio) of the number of amino acid residues of the other REP is 1.8 to 11.3, is set as x, and the total number of amino acid residues in the domain sequence is set as y, x/y is preferably 64.2% or more.

The above-described modified fibroin may include a tag sequence described above at either or both of the N-terminal and C-terminal.

A more specific example of the modified fibroin including a tag sequence may be one including (3-iii) the amino acid sequence set forth in SEQ ID Nos. 7, 9, 11, or 13, or (2-iv) an amino acid sequence having 90% or more sequence identity with the amino acid sequence set forth in SEQ ID Nos. 7, 9, 11, or 13.

The amino acid sequences set forth in SEQ ID Nos. 6, 7, 8, 9, 11, and 13 are respectively amino acid sequences obtained by adding the amino acid sequence (including a His tag sequence and a hinge sequence) set forth in SEQ ID No. 5 to the N-terminal of the amino acid sequences set forth in SEQ ID Nos. 1, 2, 3, 4, 10, and 12.

The modified fibroin of (3-iii) may consist of the amino acid sequence set forth in SEQ ID Nos. 7, 9, 11, or 13.

The modified fibroin of (3-iv) includes an amino acid sequence having 90% or more sequence identity with the amino acid sequence set forth in SEQ ID Nos. 7, 9, 11, or 13. The modified fibroin of (3-iv) is also a protein including a domain sequence represented by Formula 1: $[(A)_n$ motif-REP$]_m$. The sequence identity is preferably 95% or more.

The modified fibroin of (3-iv) preferably has 90% or more sequence identity with the amino acid sequence set forth in SEQ ID Nos. 7, 9, 11, or 13, and when the number of amino acid residues of two $[(A)_n$ motif-REP] units adjacent to each other is sequentially compared from the N-terminal side to the C-terminal side, and when the number of amino acid residues of one REP having a small number of amino acid residues is set as 1, the maximum total value of the number of amino acid residues of two $[(A)_n$ motif-REP] units adjacent to each other, in which the ratio of the number of amino acid residues of the other REP is 1.8 to 11.3, is set as x, and the total number of amino acid residues in the domain sequence is set as y, is preferably 64.2% or more.

The above-described modified fibroin may include a secretory signal for releasing the protein produced in the recombinant protein production system to the outside of a host. The sequence of the secretory signal can be appropriately set depending on the type of the host.

The domain sequence of the modified fibroin having a reduced glycine residue content and a reduced $(A)_n$ motif content has an amino acid sequence with not only a reduced content of $(A)_n$ motif but also a reduced content of glycine residue, as compared with naturally occurring fibroin. It can be said that the domain sequence of the modified fibroin has an amino acid sequence equivalent to an amino acid sequence in which at least one or a plurality of $(A)_n$ motifs are deleted and at least one or a plurality of glycine residues in REP are further substituted with other amino acid residues, as compared with naturally occurring fibroin. That is, the modified fibroin is one having the characteristics of the modified fibroin having the reduced glycine residue content and the modified fibroin having the reduced $(A)_n$ motif content. Specific aspects of the modified fibroin are as described in the modified fibroin having the reduced glycine residue content and the modified fibroin having the reduced $(A)_n$ motif content.

More specific examples of the modified fibroin a reduced glycine residue content and a reduced $(A)_n$ motif content can include a modified fibroin including (4-i) the amino acid sequence set forth in SEQ ID Nos. 4, 10, 12, or and (4-ii) an amino acid sequence having 90% or more sequence identity with the amino acid sequence set forth in SEQ ID Nos. 4, 10, or 12. Specific aspects of the modified fibroin including the amino acid sequence set forth in SEQ ID Nos. 4, 10, or 12 are as described above.

The domain sequence of other modified fibroin may include a domain sequence having one or more amino acid residues having a higher hydropathy index compared to naturally occurring fibroin in REP replacing original amino acid residues or inserted into the REP. The amino acid sequence may have a local region having a higher hydropathy index.

It is preferable that the region locally having the higher hydropathy index is constituted of two to four consecutive amino acid residues.

It is more preferable that the amino acid residues with a high hydropathy index are selected from isoleucine (I), valine (V), leucine (L), phenylalanine (F), cysteine (C), methionine (M), and alanine (A).

The modified fibroin according to the present example may further include an amino acid sequence equivalent to an amino acid sequence in which one or a plurality of amino acid residues are substituted, deleted, inserted and/or added, as compared with naturally occurring fibroin, in addition to a modification corresponding to the modification in which one or a plurality of amino acid residues in REP are substituted with amino acid residues with a high hydropathy index and/or one or a plurality of amino acid residues with a high hydropathy index are inserted into REP, as compared with naturally occurring fibroin.

The modified fibroin according to the present example may be obtained by, with respect to a cloned gene sequence of naturally occurring fibroin, substituting one or a plurality of hydrophilic amino acid residues in REP (for example, amino acid residues having a negative hydropathy index) with a hydrophobic amino acid residue (for example, amino acid residues having a positive hydropathy index), and/or inserting one or a plurality of hydrophobic amino acid residues into REP. Further, for example, the fifth modified fibroin may also be obtained by designing an amino acid sequence equivalent to an amino acid sequence in which with respect to the amino acid sequence of naturally occurring fibroin, one or a plurality of hydrophilic amino acid residues in REP are substituted with hydrophobic amino acid residues and/or one or a plurality of hydrophobic amino acid residues are inserted into REP, and chemically synthesizing a nucleic acid encoding the designed amino acid sequence. In any case, with respect to the amino acid sequence naturally occurring fibroin, in addition to the modification equivalent to substitution of one or a plurality of hydrophilic amino acid residues in REP with hydrophobic amino acid residues and/or insertion of one or a plurality of hydrophobic amino acid residues into REP, further modification of amino acid sequence equivalent to substitution, deletion, insertion and/or addition of one or a plurality of amino acid residues may be carried out.

A modified fibroin according to another example may include a domain sequence represented by Formula 1: $[(A)_n$ motif-REP$]_m$ and have an amino acid sequence in which p/q is 6.2% or more, in a case where in all REPs included in a sequence excluding a sequence from an $(A)_n$ motif located to most C-terminal side to the C-terminal of the domain sequence from the domain sequence, the total number of amino acid residues contained in a region where an average value of hydropathy indices of four consecutive amino acid residues is 2.6 or more is set as p, and the total number of amino acid residues contained in the sequence excluding the sequence from the (A) motif located the most C-terminal side to the C-terminal of the domain sequence from the domain sequence is set as q.

Regarding the hydropathy index of amino acid residues, known indices (Hydropathy index: Kyte J, & Doolittle R (1982) from "A simple method for displaying the hydropathic character of a protein", J. Mol. Biol., 157, pp. 105-132) may be used as a reference. Specifically, the hydropathy index (hereinafter also referred to as "HI") of each amino acid is as shown in Table 1 below.

TABLE 1

| Amino acid | HI |
| --- | --- |
| Isoleucine (Ile) | 4.5 |
| Valine (Val) | 4.2 |
| Leucine (Leu) | 3.8 |
| Phenylalanine (Phe) | 2.8 |
| Cysteine (Cys) | 2.5 |
| Methionine (Met) | 1.9 |
| Alanine (Ala) | 1.8 |
| Glycine (Gly) | −0.4 |
| Threonine (Thr) | −0.7 |
| Serine (S) | −0.8 |
| Tryptophan (W) | −0.9 |
| Tyrosine (Tyr) | −1.3 |
| Proline (P) | −1.6 |
| Histidine (His) | −3.2 |
| Asparagine (Asn) | −3.5 |
| Asparagine acid (Asp) | −3.5 |
| Glutamine (Gln) | −3.5 |
| Glutamine acid (Glu) | −3.5 |
| Lysine (Lys) | −3.9 |
| Arginine (Arg) | −4.5 |

The calculation method of p/q will be described in more detail. In the calculation, the sequence (hereinafter also referred to as "sequence A") excluding the sequence from the $(A)_n$ motif located at the most C-terminal side to the C-terminal side of the domain sequence from the domain sequence represented by Formula 1: $[(A)_n$ motif-REP$]_m$ is used. First, in all REPs included in the sequence A, average values of hydropathy indices of four consecutive amino acid residues are calculated. The average value of the hydropathy indices is obtained by dividing the total sum of HI of each of the amino acid residues contained in the four consecutive amino acid residues by 4 (the number of amino acid residues). The average value of the hydropathy indices is obtained for all of the four consecutive amino acid residues (each of the amino acid residues is used for calculating the average value 1 to 4 times). Next, a region where the average value of the hydropathy indices of the four consecutive amino acid residues is 2.6 or more is specified. Even if a plurality of a certain amino acid residue are determined to correspond to the "four consecutive amino acid residues having an average value of the hydropathy indices of 2.6 or more", the amino acid residue is counted as one amino acid residue in the region. The total number of amino acid residues included in the region is set as p. The total number of amino acid residues included in the sequence A is set as q.

Figure 2:
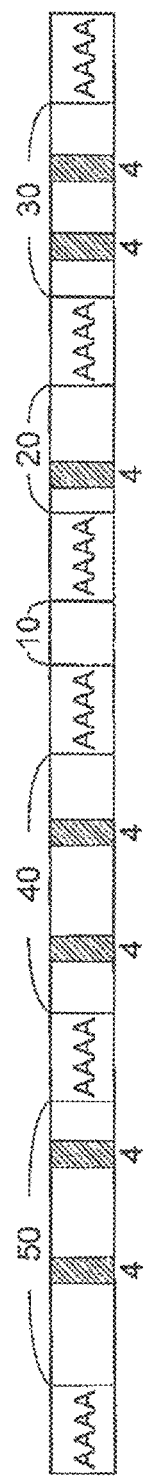
FIG. 2: A schematic view of an example of another domain sequence of a modified fibroin.
Figure 3:
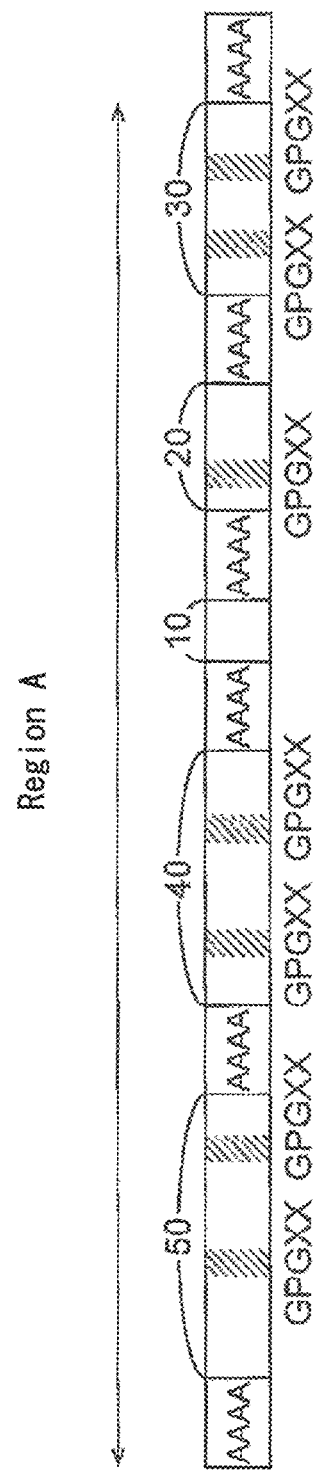
FIG. 3: A schematic view of an example of another domain sequence of a modified fibroin.

For example, in a case where the feature "four consecutive amino acid residues whose average value of hydropathy indices is 2.6 or more" is extracted from 20 places (no overlap), in the region where the average value of the hydropathy indices of four consecutive amino acid residues is 2.6 or more, the number of the four consecutive amino acid residues (no overlap) is 20, and thus p is 20×4=80. In addition, for example, when two of the "four consecutive amino acid residues having an average value of the hydropathy indices of 2.6 or more" overlap by one amino acid residue, in the region where the average value of the hydropathy indices of the four consecutive amino acid residues is 2.6 or more, the number of amino acid residues being included is 7 (p=2×4−1=7. "−1" is the deduction of overlap). For example, in the case of the domain sequence indicated in FIG. 2, there are seven pieces od consecutive four amino acid residues having an averaged hydropathy indexes not less than 2.6 without duplication, and p is equal to 28=7×4. Further, in the domain sequence indicated in FIG. 2, q is equal to 170=4+50+4+40+10+4+20+4+30 (The last $(A)_n$ motif at the C-terminal side being excluded). Next, p is divided by q to calculate p/q (%). In the case of FIG. 2, 28/170=16.47%.

In this example of modified fibroin, p/q is preferably 6.2% or more, more preferably 7% or more, still more preferably 10% or more, even still more preferably 20% or more, and still further preferably 30% or more. The upper limit of p/q is not particularly limited, but it may be 45% or less, for example.

The present example of modified fibroin may be obtained by, for example, modifying an amino acid sequence of cloned naturally occurring fibroin into an amino acid sequence containing a region locally having a high hydropathy index by substituting one or a plurality of hydrophilic amino acid residues in REP (for example, amino acid residues having a negative hydropathy index) with hydrophobic amino acid residues (for example, amino acid residues having a positive hydropathy index), and/or inserting one or a plurality of hydrophobic amino acid residues into REP, such that the p/q condition is satisfied. Alternatively, the modified fibroin may also be obtained, for example, by designing an amino acid sequence satisfying the p/q condition based on the amino acid sequence of naturally occurring fibroin and chemically synthesizing a nucleic acid encoding the designed amino acid sequence. In any case, in addition to the modification equivalent to substitution of one or a plurality of amino acid residues in REP with amino acid residues with a high hydropathy index and/or insertion of one or a plurality of amino acid residues with a high hydropathy index into REP, as compared with the naturally occurring fibroin, further modification equivalent to substitution, deletion, insertion, and/or addition of one or a plurality of amino acid residues may be carried out.

The amino acid residues with a high hydropathy index is preferably isoleucine (I), valine (V), leucine (L), phenylalanine (F), cysteine (C), methionine (M), and alanine (A), and more preferably valine (V), leucine (L), and isoleucine (I), but not particularly limited thereto.

More specific examples of the present example of modified fibroin can include a modified fibroin including (5-i) the amino acid sequence set forth in SEQ ID Nos. 20, 22, or 23, and (5-ii) an amino acid sequence having 90% or more sequence identity with the amino acid sequence set forth in SEQ ID Nos. 20, 22, or 23.

The modified fibroin of (5-i) will be described. The amino acid sequence set forth in SEQ ID No. 19 is obtained by deleting an amino acid sequence consisting of consecutive alanine residues in $(A)_n$ motif in the naturally occurring fibroin such that the number of the consecutive alanine residues becomes 5. The amino acid sequence set forth in SEQ ID No. 20 is obtained by inserting an amino acid sequence consisting of three amino acid residues (VLI) at two sites for every 2 REP with respect to the amino acid sequence set forth in SEQ ID No. 19, and deleting a part of the amino acid at the C-terminal side such that the molecular weight becomes equal to that of SEQ ID No. 19. The amino acid sequence set forth in SEQ ID No. 21 is obtained by inserting two alanine residues at the C-terminal side of each $(A)_n$ motif, substituting a part of glutamine (Q) residues with serine (S) residues, and deleting a part of amino acids on the C-terminal side. The amino acid sequence set forth in SEQ ID No. 22 is obtained by inserting an amino acid sequence consisting of three amino acid residues (VLI) at one site for each REP with respect to the amino acid sequence set forth in SEQ ID No. 21. The amino acid sequence set forth in SEQ ID No. 23 is obtained by inserting an amino acid sequence consisting of three amino acid residues (VLI) at two sites for each REP with respect to the amino acid sequence set forth in SEQ ID No. 21.

The modified fibroin of (5-i) may consist of the amino acid sequence set forth in SEQ ID Nos. 20, 22, or 23.

The modified fibroin of (5-ii) includes an amino acid sequence having 90% or more sequence identity with the amino acid sequence set forth in SEQ ID Nos. 20, 22, or 23. The modified fibroin of (5-ii) is also a protein including a domain sequence represented by Formula 1: $[(A)_n$ motif-$REP]_m$. The sequence identity is preferably 95% or more.

The modified fibroin of (5-ii) preferably has 90% or more sequence identity with the amino acid sequence set forth in SEQ ID Nos. 20, 22, or 23, and preferably has an amino acid sequence in which p/q is 6.2% or more, in a case where in all REPs included in a sequence excluding a sequence from an $(A)_n$ motif located the most C-terminal side to the C-terminal of the domain sequence from the domain sequence, the total number of amino acid residues contained in a region where an average value of hydropathy indices of four consecutive amino acid residues is 2.6 or more is set as p, and where the total number of amino acid residues contained in the sequence excluding the sequence from the $(A)_n$ motif located the most C-terminal side to the C-terminal of the domain sequence from the domain sequence is set as q.

The present example of the modified fibroin may include a tag sequence at either or both of the N-terminal and C-terminal.

A more specific example of the modified fibroin including a tag sequence may be one including (5-iii) the amino acid sequence set forth in SEQ ID Nos. 24, 25, or 26, or (5-iv) an amino acid sequence having 90% or more sequence identity with the amino acid sequence set forth in SEQ ID Nos. 24, 25, or 26.

The amino acid sequences set forth in SEQ ID Nos. 24, 25, and 26 are respectively amino acid sequences obtained by adding the amino acid sequence (including a His tag and a hinge sequence) set forth in SEQ ID No. 5 to the N-terminal of the amino acid sequences set forth in SEQ ID Nos. 20, 22, and 23.

The modified fibroin of (5-iii) may consist of the amino acid sequence set forth in SEQ ID Nos. 24, 25, or 26.

The modified fibroin of (5-iv) includes an amino acid sequence having 90% or more sequence identity with the amino acid sequence set forth in SEQ ID Nos. 24, 25, or 26. The modified fibroin of (5-iv) is also a protein including a domain sequence represented by Formula 1: $[(A)_n$ motif-$REP]_m$. The sequence identity is preferably 95% or more.

The modified fibroin of (5-iv) preferably has 90% or more sequence identity with the amino acid sequence set forth in SEQ ID Nos. 24, 25, or 26, and preferably has an amino acid sequence in which p/q is 6.2% or more, in a case where in all REPs included in a sequence excluding a sequence from an $(A)_1$ motif located the most C-terminal side to the C-terminal of the domain sequence from the domain sequence, the total number of amino acid residues contained in a region where an average value of hydropathy indices of four consecutive amino acid residues is 2.6 or more is set as p, and where the total number of amino acid residues contained in the sequence excluding the sequence from the $(A)_n$ motif located the most C-terminal side to the C-terminal of the domain sequence from the domain sequence is set as q.

The present example of the modified fibroin may include a secretory signal for releasing the protein produced in the recombinant protein production system to the outside of a host. The sequence of the secretory signal can be appropriately set depending on the type of the host.

A further modified fibroin has an amino acid sequence with a reduced content of glutamine residue, as compared with naturally occurring fibroin.

The modified fibroin according to the present example preferably includes at least one motif selected from GGX motif and GPGXX motif in the amino acid sequence in REP.

When the modified fibroin according to the present example including the GPGXX motif in the REP, the GGXX motif content is usually 1% or more, may be 5% or more, and is preferably 10% or more. The upper bound of the GPGXX content is arbitrary, may be 50% or less, and is preferably 30% or less.

In the present specification, the "GPGXX motif content rate" is a value calculated by the following method.

In a fibroin (modified fibroin or naturally occurring fibroin) including a domain sequence represented by Formula 1: $[(A)_n$ motif-$REP]_m$ or Formula 2: $[(A)$ motif-$REP]_m(A)_n$ motif, the number obtained by tripling the total number of the GPGXX motifs in all REPs included in a sequence excluding the sequence from the $(A)_n$ motif located at the most C-terminal side to the C-terminal of the domain sequence from the domain sequence (that is, equivalent to the total number of G and P in the GPGXX motifs) is set as s, and the total number of amino acid residues in all REPs excluding the sequence from the $(A)_n$ motif located at the most the C-terminal side to the C-terminal of the domain sequence from the domain sequence and further excluding $(A)_n$ motifs is set as t, the GPGXX motif content rate is calculated as s/t.

For the calculation of the GPGXX motif content rate, the "sequence excluding a sequence from the $(A)_n$ motif located at the most C-terminal side to the C-terminal of the domain sequence from the domain sequence" is used to exclude the effect occurring due to the fact that the "sequence from the $(A)_n$ motif located at the most C-terminal side to the C-terminal of the domain sequence" (sequence equivalent to REP) may include a sequence that is not correlated with the sequence characteristic of fibroin, which influences the calculation result of the GPGXX motif content rate in a case where m is small (that is, in a case where the domain sequence is short). In a case where a "GPGXX motif" is located at the C-terminal of REP, it is treated as the "GPGXX motif" even if "XX" is, for example, "AA".

FIG. 1 is a schematic diagram showing a domain sequence of a modified fibroin. The calculation method of the GPGXX motif content rate will be specifically described with reference to FIG. 1. First, in a domain sequence of a modified fibroin shown in FIG. 1 ($[(A)_n$ motif-REP$]_m$-$(A)_n$ motif] type), since all REPs are included in the "sequence excluding a sequence from the $(A)_n$ motif located at the most C-terminal side to the C-terminal of the domain sequence from the domain sequence" (shown as "region A" in FIG. 1), the number of GPGXX motifs for calculating s is 7, and s is 7×3=21. Similarly, since all REPs are included in the "sequence excluding a sequence from the $(A)_n$ motif located at the most C-terminal side to the C-terminal of the domain sequence from the domain sequence" (shown as "region A" in FIG. 1), t which is the total number of amino acid residues in all REPs excluding the sequence from the $(A)_n$ motif located at the most the C-terminal side to the C-terminal of the domain sequence from the domain sequence and further excluding $(A)_n$ motifs, is 50+40+10+20+30=150. Next, s/t (%) can be calculated by dividing s by t and is 21/150=14.0% in a case of the modified fibroin of FIG. 1.

In the modified fibroin according to the present embodiment, a glutamine residue content rate is preferably 9% or less, more preferably 7% or less, still more preferably 4% or less, and particularly preferably 0%.

In the present specification, the "glutamine residue content rate" is a value calculated by the following method.

In a fibroin including a domain sequence represented by Formula 1: [(A) motif-REP]$_m$ or Formula 2: [(A)$_n$ motif-REP]$_m$-$(A)_n$ motif, the total number of glutamine residues in all REPs included in a sequence (sequence equivalent to "region A" in FIG. 1) excluding the sequence from the $(A)_n$ motif located at the most C-terminal side to the C-terminal of the domain sequence from the domain sequence is set as u, and the total number of amino acid residues in all REPs excluding the sequence from the $(A)_n$ motif located at the most the C-terminal side to the C-terminal of the domain sequence from the domain sequence and further excluding $(A)_n$ motifs is set as t, and the glutamine residue content rate is calculated as u/t. For the calculation of the glutamine residue content rate, the "sequence excluding a sequence from the $(A)_n$ motif located at the most C-terminal side to the C-terminal of the domain sequence from the domain sequence" is used for the same reason described above.

The domain sequence of the modified fibroin according to the present embodiment may include an amino acid sequence equivalent to an amino acid sequence in which one or a plurality of glutamine residues in REP are deleted or substituted with other amino acid residues, as compared with naturally occurring fibroin.

"The other amino acid residue" may be an amino acid residue other than a glutamine residue, but is preferably an amino acid residue having a higher hydropathy index than that of a glutamine residue. The hydropathy index of each amino acid is as shown in Table 1 below.

As shown in Table 1, amino acid residues having a higher hydropathy index than that of a glutamine residue include an amino acid residue selected from isoleucine (I), valine (V), leucine (L), phenylalanine (F), cysteine (C), methionine (M), alanine (A), glycine (G), threonine (T), serine (S), tryptophan (W), tyrosine (Y), proline (P) and histidine (H). Among these, an amino acid residue selected from isoleucine (I), valine (V), leucine (L), phenylalanine (F), cysteine (C), methionine (M) and alanine (A) is more preferable, and an amino acid residue selected from isoleucine (I), valine (V), leucine (L) and phenylalanine (F) is still more preferable.

In the modified fibroin according to the present embodiment, the hydrophobicity of REP is preferably −0.8 or more, more preferably −0.7 or more, still more preferably 0 or more, even still more preferably 0.3 or more, and particularly preferably 0.4 or more. The upper limit of the hydrophobicity of REP is not particularly limited, may be 1.0 or less, and may be 0.7 or less.

In the present specification, the "hydrophobicity of REP" is a value calculated by the following method.

In a fibroin including a domain sequence represented by Formula 1: [(A) motif-REP]$_m$ or Formula 2: [(A)$_n$ motif-REP]$_m$-$(A)_n$ motif, the sum of the hydropathy indices of each amino acid residue in all REPs included in a sequence (sequence equivalent to "region A" in FIG. 1) excluding the sequence from the $(A)_n$ motif located at the most C-terminal side to the C-terminal of the domain sequence from the domain sequence is set as v, and the total number of amino acid residues in all REPs excluding the sequence from the $(A)_n$ motif located at the most the C-terminal side to the C-terminal of the domain sequence from the domain sequence and further excluding $(A)_n$ motifs is set as t, the hydrophobicity of REP is calculated as v/t. For the calculation of the hydrophobicity of REP, the "sequence excluding a sequence from the $(A)_n$ motif located at the most C-terminal side to the C-terminal of the domain sequence from the domain sequence" is used for the same reason described above.

The domain sequence of the modified fibroin according to the present embodiment may be modified compared to naturally occurring fibroin such that one or plural glutamine residues in REP may be deleted, one or plural glutamine residues in REP may be replaced by other amino acid residues, and the amino acid sequence may be modified so that one or plural amino acid residues are replaced, deleted, inserted, and/or added.

The modified fibroin according to the present embodiment can be obtained by, for example, with respect to a cloned gene sequence of naturally occurring fibroin, deleting one or a plurality of glutamine residues in REP and/or by substituting one or a plurality of glutamine residues in REP with other amino acid residues. Further, for example, the modified fibroin according to the present embodiment may also be obtained by designing an amino acid sequence equivalent to an amino acid sequence in which with respect to the amino acid sequence of naturally occurring fibroin, one or a plurality of glutamine residues in REP are deleted and/or one or a plurality of glutamine residues in REP are substituted with other amino acid residues, and chemically synthesizing a nucleic acid encoding the designed amino acid sequence.

A more specific example of the modified fibroin may be one containing (6-i) an amino acid sequence set forth in SEQ ID Nos. 27, 28, 29, 30, 31, 38, or 39, or (6-ii) one containing an amino acid sequence having 90% or more sequence identity with the amino acid sequence set forth in SEQ ID Nos. 27, 28, 29, 30, 31, 38, or 39.

The modified fibroin of (6-i) will be described.

The amino acid sequence set forth in SEQ ID No. 1 (Met-PRT410) is a modified amino acid sequence obtained by changing the number of consecutive alanine residues in (A) motif to five, or the like, so as to improve productivity, based on the base sequence and amino acid sequence of *Nephila clavipes* (GenBank Accession Number: P46804.1, GI: 1174415) which is naturally occurring fibroin. However, since Met-PRT410 has no modification of glutamine residue (Q), the glutamine residue content rate thereof is the same as the glutamine residue content of naturally occurring fibroin.

The amino acid sequence (M_PRT888) set forth in SEQ ID No. 27 is obtained by substituting all QQs in Met-PRT410 (SEQ ID No. 4) with VL.

The amino acid sequence (M_PRT965) set forth in SEQ ID No. 27 is obtained by substituting all QQs in Met-PRT410 (SEQ ID No. 4) with TS and substituting the remaining Q with A.

The amino acid sequence (M_PRT889) set forth in SEQ ID No. 29 is obtained by substituting all QQs in M_PRT410 (SEQ ID No. 4) with VL and substituting the remaining Q with I.

The amino acid sequence (M_PRT916) set forth in SEQ ID No. 30 is obtained by substituting all QQs in M_PRT410 (SEQ ID No. 4) with VI and substituting the remaining Q with L.

The amino acid sequence (M_PRT918) set forth in SEQ ID No. 31 is obtained by substituting all QQs in M_PRT410 (SEQ ID No. 4) with VF and substituting the remaining Q with I.

The amino acid sequence (M_PRT525) set forth in SEQ ID No. 37 is obtained by, with respect to M_PRT410 (SEQ ID No. 4), inserting two alanine residues in a region (A5) in which alanine residues are consecutive, and by deleting two domain sequences at the C-terminal side and substituting 13 glutamine (Q) residues with serine (S) residue or proline (P) residue such that the molecular weight thereof becomes approximately the same as that of M_PRT410.

The amino acid sequence (M_PRT699) set forth in SEQ ID No. 38 is obtained by substituting all QQs in M_PRT525 (SEQ ID No. 37) with VL.

The amino acid sequence (M_PRT698) set forth in SEQ ID No. 39 is obtained by substituting all QQs in M_PRT525 (SEQ ID No. 37) with VL and substituting the remaining Q with I.

The glutamine residue content rate of any of the amino acid sequences set forth in SEQ ID Nos. 27, 28, 29, 30, 31, and 38, 39 is 9% or less (Table 2).

TABLE 2

| Modified Fibroin | Glutamine Residue content rate (%) | GPGXX motif content rate (%) | Hydrophobicity of REP |
|---|---|---|---|
| Met-PRT410 (SEQ ID No. 4) | 17.7 | 27.9 | -1.52 |
| Met-PRT888 (SEQ ID No. 27) | 6.3 | 27.9 | -0.07 |

TABLE 2-continued

| Modified Fibroin | Glutamine Residue content rate (%) | GPGXX motif content rate (%) | Hydrophobicity of REP |
|---|---|---|---|
| Met-PRT965 (SEQ ID No. 28) | 0.0 | 27.9 | -0.65 |
| Met-PRT889 (SEQ ID No. 29) | 0.0 | 27.9 | 0.35 |
| Met-PRT916 (SEQ ID No. 30) | 0.0 | 27.9 | 0.47 |
| Met-PRT918 (SEQ ID No. 31) | 0.0 | 27.9 | 0.45 |
| Met-PRT525 (SEQ ID No. 37) | 13.7 | 26.4 | -1.24 |
| Met-PRT699 (SEQ ID No. 38) | 3.6 | 26.4 | -0.78 |
| Met-PRT698 (SEQ ID No. 39) | 0.0 | 26.4 | -0.03 |

The modified fibroin of (6-i) may consist of the amino acid sequence set forth in SEQ ID Nos. 2, 3, 4, 5, 6, 16, or 17.

The modified fibroin of (6-ii) includes an amino acid sequence having 90% or more sequence identity with the acid sequence set forth in SEQ ID Nos. 27, 28, 29, 30, 31, 38, or 39. The modified fibroin of (6-ii) is also a protein including a domain sequence represented by Formula 1: $[(A)_n\text{ motif-REP}]_m$ or Formula 2: $[(A)_n\text{ motif-REP}]_m\text{-}(A)_n$ motif. The sequence identity is preferably 95% or more.

The modified fibroin of (6-ii) preferably has the glutamine residue content rate of 9% or less. In addition, the modified fibroin of (6-ii) preferably has the GPGXX motif content rate of 10% or more.

The above-described modified fibroin may include a tag sequence at either or both of the N-terminal and C-terminal. This makes it possible to isolate, immobilize, detect and visualize the modified fibroin.

A more specific example of the modified fibroin having a tag sequence may be one containing (6-iii) an amino acid sequence set forth in SEQ ID Nos. 9, 10, 11, 12, 13, 19, or 20, or (6-iv) an amino acid sequence having 90% or more sequence identity with the amino acid sequence set forth in SEQ ID Nos. 9, 10, 11, 12, 13, 19, or 20.

The amino acid sequences set forth in SEQ ID Nos. 32, 33, 34, 35, 36, 40, and 41 are respectively amino acid sequences obtained by adding the amino acid sequence (including His tag) set forth in SEQ ID No. 5 to the N-terminal of the amino acid sequences set forth in SEQ ID Nos. 27, 28, 29, 30, 31, 38, and 39. Since only the tag sequence is added to the N-terminal, the glutamine residue content rates are not changed, and any of the amino acid sequences set forth in SEQ ID Nos. 32, 33, 34, 35, 36, 40, and 41 has the glutamine residue content rate of 9% or less (Table 3).

TABLE 3

| Modified Fibroin | Glutamine Residue content rate (%) | GPGXX motif content rate (%) | Hydrophobicity of REP |
|---|---|---|---|
| PRT888 (SEQ ID No. 32) | 6.3 | 27.9 | -0.07 |
| PRT965 (SEQ ID No. 33) | 0.0 | 27.9 | -0.65 |
| PRT889 (SEQ ID No. 34) | 0.0 | 27.9 | 0.35 |
| PRT916 (SEQ ID No. 35) | 0.0 | 27.9 | 0.47 |
| PRT918 (SEQ ID No. 36) | 0.0 | 27.9 | 0.45 |

TABLE 3-continued

| Modified Fibroin | Glutamine Residue content rate (%) | GPGXX motif content rate (%) | Hydrophobicity of REP |
|---|---|---|---|
| PRT699 (SEQ ID No. 40) | 3.6 | 26.4 | −0.78 |
| PRT698 (SEQ ID No. 41) | 0.0 | 26.4 | −0.03 |

The modified fibroin of (6-iii) may consist of the amino acid sequence set forth in SEQ ID Nos. 32, 33, 34, 35, 36, 40, or 41.

The modified fibroin of (6-iv) includes an amino acid sequence having 90% or more sequence identity with the acid sequence set forth in SEQ ID Nos. 32, 33, 34, 35, 36, 40 or 41. The modified fibroin of (6-iv) is also a protein including a domain sequence represented by Formula 1: [(A)$_n$ motif-REP]$_m$ or Formula 2: [(A) motif-REP]$_m$-(A)$_n$ motif. The sequence identity is preferably 95% or more.

The modified fibroin of (6-iv) preferably has the glutamine residue content rate of 9% or less. In addition, the modified fibroin of (6-iv) preferably has the GPGXX motif content rate of 10% or more.

The above-mentioned modified fibroin may include a secretory signal for releasing the protein produced in the recombinant protein production system to the outside of a host. The sequence of the secretory signal can be appropriately set depending on the type of the host.

<Production of Modified Fibroin>

The above modified fibroins (proteins) according to the above examples may be produced by the nucleic acid sequences encoding the proteins and the host transformed by expression vectors having one or more regulatory sequences connected to work on the nucleic acid sequences to express the nucleic acids.

The production methods of the nucleic acid encoding the modified fibroin are not specifically limited. For example, a method using a gene encoding naturally occurring fibroin, cloning and amplifying it by polymerase chain reaction (PCR), and modifying it with genetic technology, and a method using chemical synthesis are applicable. The chemical synthesis methods of the nucleic acid are not specifically limited, for example, the gene may be chemically synthesized, based upon amino acid sequence information of proteins from a web-database such as NCBI, and connecting oligo-nucleotide automatically synthesized with AKTA oligopilot plus 10/1000 (GE Health Care Japan) by PCR or the like. For making purification and/or confirmation of the fibroin easy, a nucleic acid encoding a modified fibroin that is added with an amino acid sequence consisting of a start codon and a HIS 10 tag at the N-terminal of the amino acid sequence according to the example may be synthesized.

The regulatory sequence is a sequence (for example, a promoter, an enhancer, a ribosome binding sequence, or a transcription termination sequence) that controls the expression of a recombinant protein in a host, and can be appropriately selected depending on the type of the host. The promoter may be an inductive promoter that functions in a host cell and can induce the expression the modified fibroins. The inductive promoter is one that can regulate the transcription under the presence of an induction material (expression inducing agent), absence of repressor molecules, or physical factors such as increase or decrease in temperature, osmotic pressure, or pH.

The type of the expression vector such as a plasmid vector, a viral vector, a cosmid vector, a fosmid vector, or an artificial chromosome vector can be appropriately selected depending on the type of the host. As the expression vector, an expression vector which can autonomously replicate in a host cell or can be incorporated into a chromosome of a host and which contains a promoter at a position capable of transcribing the nucleic acid is suitably used.

Both prokaryotes and eukaryotes such as yeast, filamentous fungi, insect cells, animal cells, and plant cells can be suitably used as hosts.

Examples of the preferable prokaryote host include microorganisms belonging to the genus *Escherichia, Brevibacillus, Serratia, Bacillus, Microbacterium, Brevibacterium, Corynebacterium*, and *Pseudomonas*. Examples of microorganisms belonging to the genus *Escherichia* include *Escherichia coli*. Examples of microorganisms belonging to the genus *Brevibacillus* include *Brevibacillus agri*. Examples of microorganisms belonging to the genus *Serratia* include *Serratia liquefacience*. Examples of microorganisms belonging to the genus *Bacillus* include *Bacillus subtilis*. Examples of microorganisms belonging to the genus *Microbacterium* include *Microbacterium ammoniaphilum*. Examples of microorganisms belonging to the genus *Brevibacterium* include *Brevibacterium divaricatum*. Examples of microorganisms belonging to the genus *Corynebacterium* include *Corynebacterium ammoniagenes*. Examples of microorganisms belonging to the genus *Pseudomonas* include *Pseudomonas putida*.

When a prokaryote host is used, examples of the vector into which the nucleic acid is introduced include pBTrp2 (commercially available from Boehringer Mannheim GmbH), pGEX (manufactured by Pharmacia Corporation), pSE280 (manufactured by Invitrogen Corporation), pGEMEX-1 (manufactured by Promega Corporation), pUC18, pBluescriptll, pSupex, pET22b, pCold, pUB110, and pNCO2 (Japanese Laid Open Patent 2002-238569).

Examples of eukaryotic hosts include yeast, filamentous fungi (mold and the like), and insect cells. Examples of the yeast include yeasts belonging to the genus *Saccharomyces, Schizosaccharomyces*, and *Pichia*. Examples of filamentous fungi include fungi belonging to the genus *Aspergillus, Penicillium*, and *Trichoderma*.

Examples of the vector in the case where a eukaryotic host is used include YEP13 (ATCC 37115) and YEp24 (ATCC 37051). As a method for introducing an expression vector into the foregoing host cell, any method can be used as long as it introduces DNA into the host cell. Examples thereof include a method using calcium ions [Proc. Natl. Acad. Sci. USA, 69, 2110 (1972)], an electroporation method, a spheroplast method, a protoplast method, a lithium acetate method, and a competent method.

As for the expression method of the nucleic acid by the host transformed by the expression vector, secretory production, fusion protein expression, or the like, in addition to direct expression, can be carried out according to the method described in Molecular Cloning, 2nd edition.

The modified fibroin can be produced, for example, by culturing a host transformed with the expression vector in a culture medium, producing and accumulating the modified fibroin in the culture medium, and then collecting the modified fibroin from the culture medium. The method for culturing the host in a culture medium can be carried out according to a method commonly used for culturing a host.

When the host is a prokaryote such as *Escherichia coli* or a eukaryote such as yeast, any of a natural medium and a synthetic medium may be used as a culture medium of the host as long as it contains a carbon source, a nitrogen source, inorganic salts and the like which can be assimilated by the host and it is capable of efficiently culturing the host.

As the carbon source, any carbon source that can be assimilated by the host may be used. Examples of the carbon source that can be used include carbohydrates such as glucose, fructose, sucrose, and molasses, starch and starch hydrolyzates containing them, organic acids such as acetic acid and propionic acid, and alcohols such as ethanol and propanol. Examples of the nitrogen source that can be used include ammonium salts of inorganic or organic acids such as ammonia, ammonium chloride, ammonium sulfate, ammonium acetate, and ammonium phosphate, other nitrogen-containing compounds, peptone, meat extract, yeast extract, corn steep liquor, casein hydrolyzate, soybean cake, and soybean cake hydrolyzate, various fermented microbial cells and digested products thereof. Examples of the inorganic salt that can be used include potassium dihydrogen phosphate, dipotassium phosphate, magnesium phosphate, magnesium sulfate, sodium chloride, ferrous sulfate, manganese sulfate, copper sulfate, and calcium carbonate.

Culture of a prokaryote such as *Escherichia coli* or a eukaryote such as yeast can be carried out under aerobic conditions such as shaking culture or deep aeration stirring culture. The culture temperature is, for example, 15° C. to 40° C. The culture time is usually 16 hours to 7 days. It is preferable to maintain the pH of the culture medium during the culture at 3.0 to 9.0. The pH of the culture medium can be adjusted using an inorganic acid, an organic acid, an alkali solution, urea, calcium carbonate, ammonia, or the like.

In addition, antibiotics such as ampicillin and tetracycline may be added to the culture medium as necessary during the culture. In the case of culturing a microorganism transformed with an expression vector using an inducible promoter as a promoter, an inducer may be added to the medium as necessary. For example, in the case of culturing a microorganism transformed with an expression vector using a lac promoter, isopropyl-β-D-thiogalactopyranoside or the like is used, and in the case of culturing a microorganism transformed with an expression vector using a trp promoter, indole acrylic acid or the like may be added to the medium.

The modified fibroin produced by the host transformed with the expression vector can be isolated and purified by a method commonly used for protein isolation and purification. For example, in the case where the modified fibroin is expressed in a dissolved state in cells, the host cells are recovered by centrifugation after completion of the culture, suspended in an aqueous buffer solution, and then disrupted using an ultrasonicator, a French press, a Manton-Gaulin homogenizer, a Dyno-Mill, or the like to obtain a cell-free extract. From the supernatant obtained by centrifuging the cell-free extract, a purified preparation can be obtained by a method commonly used for protein isolation and purification, that is, a solvent extraction method, a salting-out method using ammonium sulfate or the like, a desalting method, a precipitation method using an organic solvent, an anion exchange chromatography method using a resin such as diethyl-amino-ethyl (DEAE)-Sepharose or DIAION HPA-75 (manufactured by Mitsubishi Kasei Kogyo Kabushiki Kaisha), an cation exchange chromatography method using a resin such as S-Sepharose FF (Pharmacia Corporation), a hydrophobic chromatography method using a resin such as butyl sepharose or phenyl sepharose, a gel filtration method using a molecular sieve, an affinity chromatography method, a chromatofocusing method, an electrophoresis method such as isoelectric focusing or the like, alone or in combination thereof.

In the case where the modified fibroin is expressed by the formation of an insoluble matter in the cell, similarly, the host cells are recovered, disrupted, and centrifuged to recover the insoluble matter of the modified fibroin as a precipitated fraction. The recovered insoluble matter of the modified fibroin can be solubilized with a protein denaturing agent. After this operation, a purified preparation of modified fibroin can be obtained by the same isolation and purification method as described above. In the case where a modified fibroin or a derivative in which a sugar chain has been added to the modified fibroin is secreted extracellularly, the modified fibroin or the derivative thereof can be recovered from the culture supernatant. That is, a culture supernatant is obtained by treating the culture by a technique such as centrifugation, and a purified preparation can be obtained from the culture supernatant by using the same isolation and purification method as described above.

EXAMPLES

Hereinafter, the present invention will be described more specifically based on Examples. However, the present invention is not limited to the following Examples.

<Production of Modified Spider Fibroin>

<Plasmid Expression Line of Modified Spider Fibroin Fiber>

The plasmid expression line was produced as the following. Based on the base sequence and amino acid sequence of *Nephila clavipes* (GenBank Accession Number: P46804.1, GI: 1174415), a modified spider silk fibroin having amino acid sequences set forth in SEQ ID No: 36 (hereinafter, referred to as "PRT918") was designed. The amino acid sequence set forth in SEQ ID No. 36 has the backbone amino acid sequence of fibroin derived from *Nephila clavipes* that was modified by the substitution, insertion, and deletion of amino acid residues to improve the productivity, the addition of the amino acid sequence set forth in SEQ ID No. 5 (tag sequence and hinge sequence) to the terminal, and the substitution of QQs in the amino acid sequence with VF and substituting the remaining Q with I.

<Nucleic Acid Synthesis>

A nucleic acid encoding PRT918 was synthesized. In the nucleic acid, an NdeI site was added to the 5' end and an EcoRI site was added downstream of the stop codon. The nucleic acid was cloned into a cloning vector (pUC118; JP2002-238569). Thereafter, the nucleic acid was enzymatically cleaved by treatment with NdeI and EcoRI, and then recombined into a protein expression vector pET-22b(+) (JP2002-238569) to obtain the expression vector.

*Escherichia coli* BLR (DE3) was transformed with a pET22b(+) expression vector including a nucleic acid encoding protein having the amino acid sequences set forth in SEQ ID No: 36. The transformed *Escherichia coli* was cultured in 2 mL of an LB medium containing ampicillin for 15 hours. The culture solution was added to 100 mL of a seed culture medium (Table 4) containing ampicillin so that the $OD_{600}$ (optical density at 600 nm) was 0.005. While maintaining the temperature of the culture solution at 30° C., flask culture was carried out (for about 15 hours) until the $OD_{600}$ reached 5, thereby obtaining a seed culture solution.

TABLE 4

Seed Culture Medium

| Reagent | Concentration (g/L) |
|---|---|
| Glucose | 5.0 |
| $KH_2PO_4$ | 4.0 |
| $K_2HPO_4$ | 9.3 |
| Yeast Extract | 6.0 |
| Ampicillin | 0.1 |

The seed culture solution was added to a jar fermenter containing 500 mL of a production medium (Table 5) so that the transformed *Escherichia coli* was inoculated at the $OD_{600}$ of 0.05. The culture was carried out while keeping the culture solution temperature at 37° C. and controlling the pH constant at 6.9. Further, the dissolved oxygen concentration in the culture solution was maintained at 20% of the dissolved oxygen saturation concentration.

TABLE 5

Production Culture Medium

| Reagent | Concentration (per L) |
|---|---|
| Glucose | 12.0 g |
| $KH_2PO_4$ | 9.0 g |
| $MgSO_4$—$7H_2O$ | 2.4 g |
| Yeast Extract | 15 g |
| $FeSO_4$—$7H_2O$ | 40 mg |
| $MnSO_4$—$7H_2O$ | 40 mg |
| $CaC_2$—$2H_2O$ | 40 mg |
| GD-113 (defoaming agent) | 0.1 mL |

Immediately after glucose in the production medium was completely consumed, a feed solution (455 g/l L of glucose and 120 g/l L of Yeast Extract) was added at a rate of 1 m/min. The culture was carried out while keeping the culture solution temperature at 37° C. and controlling the pH constant at 6.9. Further, the dissolved oxygen concentration in the culture solution was maintained at 20% of the dissolved oxygen saturation concentration, and the culture was carried out for. 20 hours. Thereafter, 1 M isopropyl-β-thiogalactopyranoside (IPTG) was added to the culture solution to a final concentration of 1 mM to induce the expression of the target protein. 20 hours after the addition of IPTG, the culture solution was centrifuged to recover the bacterial cell pellet. SDS-PAGE was carried out using bacterial cell pellets prepared from the culture solution before the addition of IPTG and after the addition of IPTG, and the expression of the target protein was checked by the IPTG addition-dependent appearance of a band equivalent to a target protein size.

<Purification of Protein>

The bacterial cell pellet recovered 2 hours after the addition of IPTG was washed with a 20 mM Tris-HCl buffer solution (pH 7.4). The bacterial cell pellet after washing was suspended in 20 mM Tris-HCl buffer solution (pH 7.4) containing about 1 mM PMSF, and the cell suspension was disrupted with a high-pressure homogenizer (available from GEA Niro Soavi SpA). The disrupted cells were centrifuged to obtain a precipitate. The obtained precipitate was washed with 20 mM Tris-HCl buffer solution (pH 7.4) until the obtained precipitate became highly pure. The precipitate after washing was suspended in 8 M guanidine buffer solution (8 M guanidine hydrochloride, 10 mM sodium dihydrogen phosphate, 20 mM NaCl, 1 mM Tris-HCl, pH 7.0) so that the concentration of the suspension was 100 mg/mL, and dissolved by stirring with a stirrer at 60° C. for 30 minutes. After dissolution, dialysis was carried out in water using a dialysis tube (cellulose tube 36/32 manufactured by Sanko Junyaku Co., Ltd.). The white protein aggregate obtained after dialysis was recovered by centrifugation, the water content was removed with a lyophilizer, and lyophilized powder was recovered to get the artificial spider silk fibroin "PRT918."

<Production of Modified Spider Silk Protein Fiber>

The above modified fibroin (PRT918) was added into DMSO at a concentration of 24 mass %, and then LiCl was added as a dissolution promoter at a concentration of 4.0 mass %. After that, the modified fibroin was dissolved with shaking for 3 hours by a shaker to get a DMSO (dimethylsulfoxide) solution. The dirt and bubble in the solution were removed to get a dope solution. The solution viscosity of the dope liquid was 5000 cP (centipoise) at 90 degree Celsius.

The above dope liquid was treated by a spinning device to wind up artificial spider fibroin fiber on a bobbin by a known dry-wet spinning method. The dry-wet spinning was performed under the following conditions:

| | |
|---|---|
| Temperature of coagulation liquid (methanol): | 5-10 degree Celsius; |
| Draw ratio: | 4.52 |
| Drying temperature: | 80 degree Celsius |

<Production of Spun Yarn>

Several artificial spider silks consisting of the above artificial spider silk protein on the bobbin were bundled and cut into bundles of staples having a mean length of 40 mm by a bench-top fiber cutter. The staples were immersed in water at 40 degree Celsius to crimp them and then, dried at 40 degree Celsius for 18 hours to prepare crimped staples. The resultant staples were spun by a known spinning machine (a four threaded carding machine and a mule spinning machine) to prepare spun yarn consisting of the artificial spider silk protein fiber. The spun yarn had a count number of 30 Nm and a twist number of Z340. The contact condition with water is arbitrary; for example, the staples may be immersed in aqueous solvents such as water-methanol, or water-ethanol or may be kept in a hot humid atmosphere to absorb water.

The crimping character of artificial protein fiber (for example, the artificial spider silk protein fiber) is not sufficient, and the inventors observed that the staples were drawn during the spinning to lose crimp. Textile products made of the above spun yarn had insufficient textures such as bulkiness. Further, the above textile products were difficult in fulling.

Therefore, heterogeneous protein such as low molecular weight hydrolyzed keratin was infiltrated into the staples of artificial spider silk protein fiber to improve the texture by enhancing the crimping character and to make fulling possible. The infiltration of the protein may be applied to filaments, the staples, or the spun yarn of the protein fiber or may be applied to the textile products.

To 100 g of feather derived from water-birds, 1 Kg of 1.3 mass % aqueous solution of sodium hydro-oxide was added, the mixture was reacted at 120 degree Celsius for 20 minutes and then cooled down naturally to 20 degree Celsius. Then, the pH was adjusted to 4 by adding hydrochloric acid and was kept still at room temperature for 12 hours. The undecomposed substance was removed by centrifugal separation and pH was adjusted to 5.6 by sodium hydro-oxide to prepare a solution of alkaline hydrolyzed keratin derived from feather. The number averaged molecular weight by SDS-PAGE was 1500.

The above yarn made of several staples of the artificial spider silk protein fiber was used to knit knitted fabrics with a 14 gauge circular knitting machine.

The knitted fabrics were immersed in the above hydrolyzed keratin aqueous solution to crimp the staples and to full the textile products. In embodiments 1-6, they were immersed in an aqueous solution (pH: about 7) of the hydrolyzed keratin derived from feather (number averaged molecular weight: 1500) at a bath ratio (the mass ratio between the knitted fabrics and the aqueous solution of hydrolyzed keratin) of 1:2 and they were stirred in a paddle dyeing machine. During the stirring, the knitted fabrics moved calmly in the aqueous solution, and no strong collision between the knitted fabrics and the wall of the vessel was observed. The object of the stirring was to make contact with the knitted fabrics uniformly with the hydrolyzed keratin aqueous solution and to infiltrate the hydrolyzed keratin aqueous solution into the inside of the spun yarn of the knitted fabrics and was not to apply impact on the knitted fabrics.

The concentration of the hydrolyzed keratin aqueous solution was changed within a range of 0.01 mass % to 0.5 mass %, mainly in a region of 0.5 mass % to 0.1 mass %. The immersing period was changed within a range of 10 minutes to 480 minutes and was typically 60 minutes. The temperature of the hydrolyzed keratin aqueous solution was changed within a range of 10 to 95 degree Celsius and was typically at 40 degree Celsius. After the treatment in the aqueous hydrolyzed keratin solution, the knitted fabrics were naturally dried at room temperature for 12 hours. Then, the properties of the knitted fabrics were observed, the stitch numbers along the wale direction and the course direction were measured, and the texture such as touch feel was observed.

A 0.2 mass % aqueous solution of commercial hydrolyzed silk (number averaged molecular weight of 1000) that was a hydrolyzed product of silk fibroin was prepared. In the paddle dyeing machine, the above knitted fabric was immersed in the solution, at a bath ratio of 1:20, at a liquid temperature of 40 degree Celsius, and for 60 minutes and was similarly treated with the embodiments 1 to 6. This example is referred to as embodiment 7.

Figure 4:
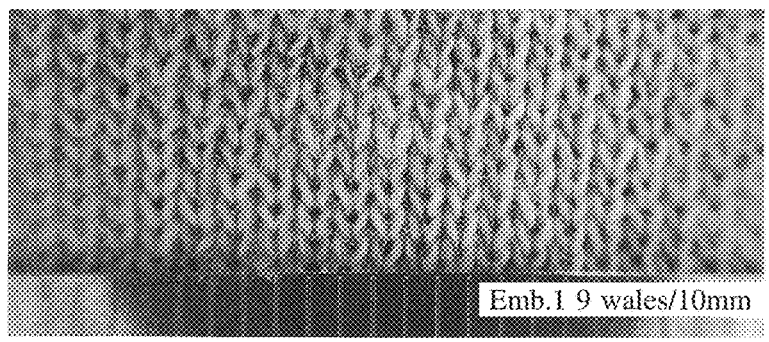
FIG. 4: A photograph of a knitted fabric fulled in embodiment 1.
Figure 5:
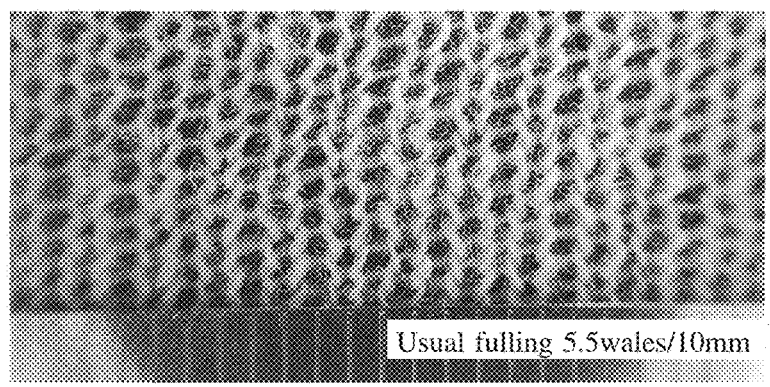
FIG. 5: A photograph of a knitted fabric fulled in comparative example 1.
Figure 6:
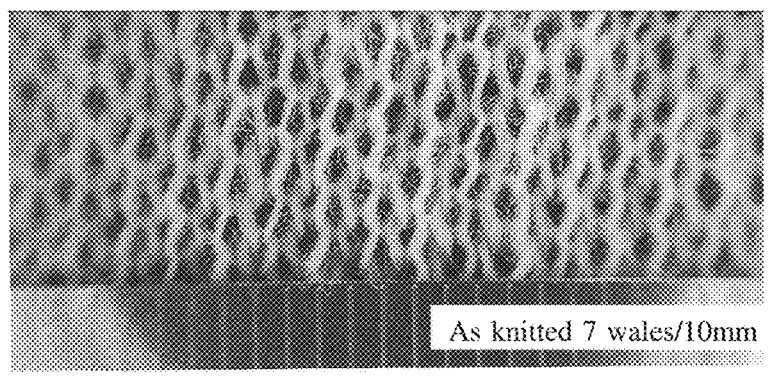
FIG. 6: A photograph of a knitted fabric before being fulled.
Figure 7:
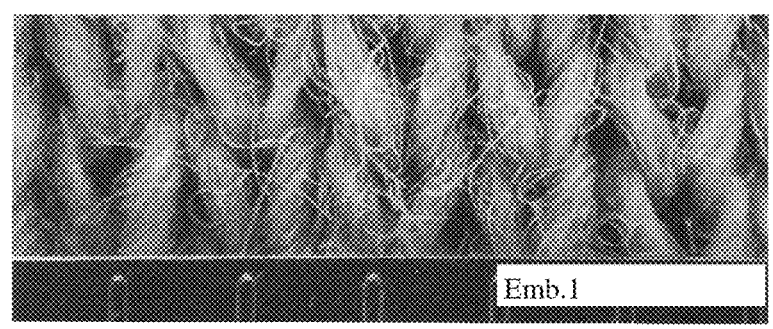
FIG. 7: An enlarged photograph of the knitted fabric fulled in embodiment 1.
Figure 8:
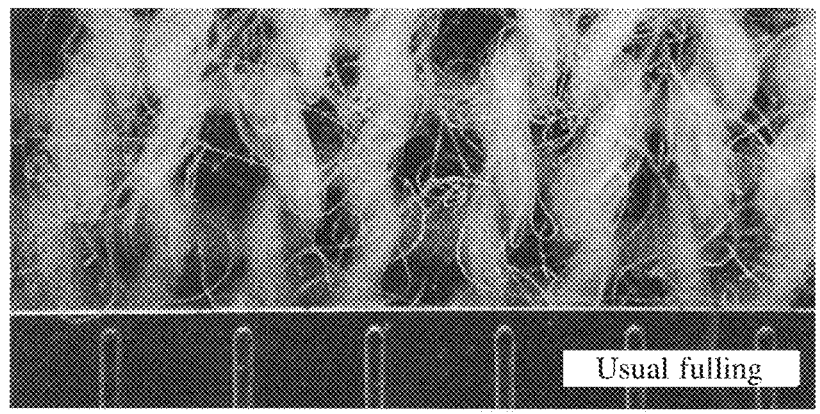
FIG. 8: An enlarged photograph of the knitted fabric fulled in the comparative example 1.
Figure 9:
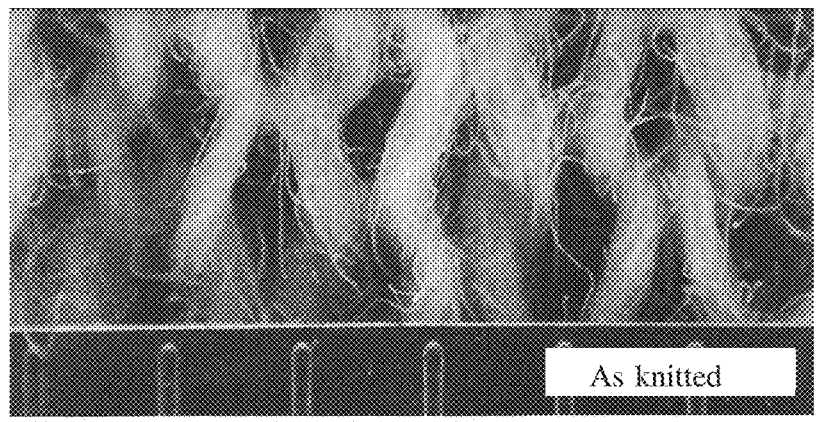
FIG. 9: An enlarged photograph of the knitted fabric before fulled.

In comparative example 1, the knitted fabric was similarly fulled as sheep wool knitted fabrics. Namely, in place of hydrolyzed keratin aqueous solution, water without additives was used, and, in place of the paddle dyeing machine, a washer dyeing machine was used to collide the knitted fabrics to the wall of the dyeing machine to full the knitted fabric. The bath ratio was 1:20, the treatment temperature was 40 degree Celsius, and the processing period was for 20 minutes. In comparative example 2, the paddle dyeing machine was used similarly with the embodiments, but, in place of the hydrolyzed keratin aqueous solution, water without additives was used to observe the effects by stirring in the paddle dyeing machine. In addition, a knitted fabric experienced no further treatment was evaluated. The results are shown in Table 6. The knitted fabric after the treatment according to Embodiment 1 is shown in the photos of FIGS. 4 and 7, that after the treatment according to Comparative example 1 is shown in the photos of FIGS. 5 and 8, and that without no further treatment after the knitting is shown in the photos of FIGS. 6 and 9. FIGS. 7 to 9 are enlarged photos allowing observation of crimp of the staples.

TABLE 6

Crimp and Fulling by Immersing in Hydrolyzed keratin Aq. Solution

| | Immersing Temp.[a] | Period (min.) | Conc. of Solution (mass %) | Stitch No.[b] (/cm) | Stitch No.[c] (/cm) | Stitch Density (/cm$^2$) |
|---|---|---|---|---|---|---|
| Com. 1 | 40 | 20 | 0 | 5.5 | 11 | 60.5 |
| Com. 2 | 40 | 60 | 0 | 7 | 6 | 42 |
| Untreated | None | None | None | 7 | 5.5 | 38.5 |
| Emb. 1 | 40 | 60 | 0.20 | 9 | 11 | 99 |
| Emb. 2 | 40 | 10 | 0.50 | 8 | 8.5 | 68 |
| Emb. 3 | 40 | 120 | 0.10 | 7 | 11 | 77 |
| Emb. 4 | 40 | 480 | 0.01 | 7 | 9.5 | 66.5 |
| Emb. 5 | 10 | 60 | 0.50 | 8 | 8.5 | 68 |
| Emb. 6 | 95 | 60 | 0.10 | 8 | 10 | 80 |
| Emb. 7* | 40 | 60 | 0.20 | 8.5 | 10.5 | 89.3 |

[a]in degree Celsius;
[b]Stitch number in the course direction; and
[c]Stitch number in the wale direction.
*In Emb. 7, hydrolyzed silk (number averaged molecular weight: 1000) was used in place of keratin.

The staples in Emb. 1 were remarkably crimped, the spun yarn was made bulky, and the knitted fabric had improved texture. The stitches were made denser along the course direction (the horizontal direction in the figures) and also the wale direction (the vertical direction in the figures), the gap between the stitches was made smaller, and the knitted fabric was successfully fulled.

On the contrary, in Comparative example 1 where regular fulling conditions were applied, the crimp was observed to be slightly enhanced than in the untreated sample, and the bulkiness of the spun yarn was slight. The stitches became denser along the wale direction but thinner along the course direction, conspicuous gaps appeared between the stitches along the course direction, and the fulling failed.

In Comparative example 2, the paddle dyeing machine was used similarly with the embodiments, but the keratin concentration was made 0 to try the fulling. Slight crimp appeared, the stitches became slightly denser along the wale direction, but the fulling failed.

As is apparent from these facts, that crimp recovered and the fulling was realized is due to keratin in the aqueous solution. Since the embodiments do not apply strong force to knitted fabrics, fine textile products can be fulled. By the way, woven fabrics and non-woven fabrics may be fulled instead of knitted fabrics. Further, the spun yarn may be immersed in a hydrolyzed keratin aqueous solution so as to make crimp.

The concentration of the hydrolyzed keratin aqueous solution was changed within the range of 0.01 mass % to 0.5 mass %, and in every example, crimp reappeared and fulling was successfully performed. However, the keratin concentration is preferably not less than 0.1 mass %, since, under 0.1 mass %, a long treatment period was necessary. Further, for performing a mild treatment, the concentration is preferably not more than 2 mass %. While all of the immersing period of 10 minutes to 480 minutes were successful, the immersing period of 480 minutes is long and not preferable. When the keratin concentration is made higher than in Embodiment 2 (keratin concentration of 0.5 mass %), shorter immersing periods may be used. From these observations, the immersing period is preferably not less than 5 minutes and not longer than 120 minutes. When the temperature of the hydrolyzed keratin aqueous solution was made at 90 degree Celsius (Emb. 6), the knitted fabric after the treatment became hard and the texture lowered. Further, when the temperature was made at 10 degree Celsius, the required processing period became four times. Therefore, the temperature of the aqueous solution is preferably from 30 degree Celsius to 60 degree Celsius. In the embodiments, a small bath ratio of 1:20 was usable. Therefore, the wasted water and the accompanying environmental load are reduced.

The keratin aqueous solution may include, other than water and keratin, other ingredients such as a chelate agent, a metal salt, ceramide, lipid, citric acid, a surf-actant, pH adjustment agent, antiseptic, ethanol, methanol. In place of the paddle dyeing machine, other arbitrary immersing devices such as a washer dyeing machine may be used. However, generation of crimp and fulling can be performed without collision to the vessel wall, it is preferable to immerse and to stir mildly the spun yarn or the textile products.

Other proteins than keratin may be used. Further, instead of feather derived keratin, sheep wool derived keratin and so on may be used. For example, in Emb. 7, hydrolyzed silk (number averaged molecular weight of 1000) was successfully used to regenerate crimp and to full the knitted fabric. This shows that aqueous solutions of collagen or artificial protein may be used. However, in Emb. 7, the knitted fabric after fulling was not sufficient in inflation (bulkiness) and firmness (tendency to keep the shape) in comparison with Emb. 1.

There are two species of keratin: low molecular weight hydrolyzed keratin (number averaged molecular weight from 500 to 5000) and high molecular weight solvable keratin (number averaged molecular weight of about 10,000). By hydrolyzed keratin aqueous solution, crimp of staples and fulling of knitted fabrics are possible, and the inventors found keratin of number averaged molecular weight from 500 to 3000 is preferable. However, solvable keratin was not sufficient in these advantageous results. The inventors considered how keratin worked to the staples of artificial spider silk protein when the staples were immersed in the hydrolyzed keratin aqueous solution.

The protein fiber may be, other than the artificial spider fiber, artificial silk introduced with amino acid residue and so on. In addition, semi-artificial protein fiber such as ProMix and Chinon and reclaimed protein fiber such as casein protein fiber, peanut protein fiber, corn protein fiber, and soybean protein fiber may be usable.

<Improvement in Color-Fastness and Crimping Character>

The above modified fibroin (PRT918) was used to produce the artificial protein fiber and the spun yarn according to the embodiments already described. Knitted fabrics were knitted with the 14 gauge knitting machine from the spun yarn. The knitted fabrics were immersed in hydrolyzed keratin aqueous solutions to test the improvement in the crimping character and color-fastness.

To 100 g of feather derived from water-birds, 1 Kg of 1.3 mass % aqueous solution of sodium hydro-oxide was added, the mixture was reacted at 120 degree Celsius for 20 minutes and then cooled down naturally to 20 degree Celsius. Then, the pH was adjusted to 4 by adding hydrochloric acid and was kept still at room temperature for 12 hours. The undecomposed substance was removed by centrifugal separation and pH was adjusted to 5.6 by sodium hydro-oxide. Then, ingredients having a molecular weight of 5000 or more were removed by dialysis to prepare a solution of alkaline hydrolyzed keratin derived from feather. The number averaged molecular weight by SDS-PAGE was 1500. The number averaged molecular weight is preferably not less than 750 and not more than 4000, in particular, not less than 750 and not more than 2000, for permeating the hydrolyzed keratin into the inside of artificial protein fiber.

In embodiments regarding the crimping character and dyeing, then knitted fabrics were first immersed in the hydrolyzed keratin solution and then died. In comparative examples, the knitted fabrics were died without the treatment by the hydrolyzed keratin. In the embodiments, in an aqueous solution of hydrolyzed keratin (number averaged molecular weight 1500, 0.1 mass % concentration, pH about 7, liquid temperature 40 degree Celsius, 20 L of the solution per 1 Kg of the knitted fabrics), the knitted fabrics comprising the artificial protein fiber were immersed in the paddle dyeing machine for 60 minutes. The pH is preferably not less than 6 and not more than 8, in particular, not less than 6.5 and not more than 7.5, the liquid temperature is preferably not less than 30 degree Celsius and not more than 80 degree Celsius, in particular, not less than 30 degree Celsius and not more than 60 degree Celsius. The concentration of keratin is preferably not less than 0.01 mass % and not more than 0.5 mass %, in particular, not less than 0.02 mass % and not more than 0.5 mass %. At 1 mass %, the knitted fabric became hard and not suited for clothes. At concentrations lower than 0.01 mass %, the keratin absorption of the knitted fabrics was not sufficient and the crimping character and the color-fastness were not sufficient. The immersing period is preferably not shorter than 40 minutes and not longer than 80 minutes; the keratin absorption of the knitted fabrics showed a maximum at an immersing period of about 60 minutes.

The paddle dyeing machine circulates the keratin aqueous solution to contact it with the knitted fabrics, and the contact method between the keratin aqueous solution and the knitted fabrics are arbitrary. While in the embodiments, the knitted fabrics were treated with the keratin aqueous solution, but the fiber itself, spun yarn, woven fabrics, non-woven fabrics, textile products may be treated. Namely, the form of artificial protein fiber when treated by keratin aqueous solution is arbitrary.

1 g of the artificial protein fiber was filled in a liquid chromatography column (Econo-Pac; BIO-RAD). A keratin aqueous solution of (number averaged molecular weight: 1500, 40 degree Celsius, 0.1 mass %) was circulated within the column for 120 minutes and the keratin concentrations at an immediately upstream position and an immediately downstream position were measured to measure the total absorption amount in the fiber. The measurement was repeated three-times with exchanging the fiber, the average total absorption amount is indicated in Table 7 in a relative value where the absorption amount at 60 minutes is normalized as 1. In each of the three measurements, a peak of the absorption amount is observed at 30 minutes of the immersing period.

TABLE 7

| Keratin Absorption Amounts and Immersing period | |
|---|---|
| Immersing Period (min.) | Relative keratin Absorption Amount (%) |
| 0 | 0 |
| 10 | 9 |
| 20 | 55 |
| 30 | 85 |
| 40 | 92 |
| 50 | 97 |
| 60 | 100 |
| 70 | 98 |
| 80 | 97 |

TABLE 7-continued

Keratin Absorption Amounts and Immersing period

| Immersing Period (min.) | Relative keratin Absorption Amount (%) |
|---|---|
| 100 | 83 |
| 110 | 83 |
| 120 | 82 |

The knitted fabrics were dehydrated and naturally dried after being immersed in the keratin aqueous solutions. The knitted fabrics shrank and the fibers therein crimped as is similar to the artificial spider silk protein fiber after the hydrolyzed keratin treatment. In the following, embodiments regarding dyeing and crimp were performed similarly with the embodiments regarding crimp unless otherwise noted, and the description of the embodiments regarding crimp applies to the embodiments regarding dyeing and crimp.

The inventors have observed that when the knitted fabrics after the keratin treatment were immersed in weakly acidic aqueous solutions of pH 5.5 (the preferable range of pH is not less than 5 and not more than 6) keratin was stably combined to the knitted fabrics to improve the resistance to washing. The inventors have speculated this phenomenon as the combination of several molecules of keratin in the fiber to a kind of polymerization or association. Direct dye and sheep wool reactive dye used in dyeing are weakly acidic, and therefore, keratin is more firmly fixed in fiber by dyeing.

The knitted fabrics were dyed by four kinds of sheep wool reactive dyes. As the yellow dye, LANAZOL Yellow 4G, (LANAZOL is a registered trademark of Huntsman) 3% (owf), anhydrous sodium sulfate ($Na_2SO_4$) 10% (owf), and acetic acid 1% (owf) were used, as the red dye, LANAZOL Red 6G 3% (owf), anhydrous sodium sulfate ($Na_2SO_4$) 10% (owf), and acetic acid 1% (owf), as the black dye, LANAZOL Deep Black CE-R 7% (owf), anhydrous sodium sulfate ($Na_2SO_4$) 5% (owf), and acetic acid 4% (owf), and as the blue dye, LANAZOL Blue 3G 3% (owf), anhydrous sodium sulfate ($Na_2SO_4$) 10% (owf), and acetic acid 1% (owf). Since the blue dye afforded relatively good results without the keratin treatment, results of the yellow, red, and black dyes are indicated in Table 8-10 where washing resistance is clearly improved by the keratin treatment. The dyeing condition was as follows: In water at 20 degree Celsius, the dyestuff and other agents and the fabrics were immersed and kept for 10 minutes; heated to 90 degree Celsius and then kept for 30 minutes; and then the fabrics were washed in water.

TABLE 8

Dyeing Color-Fastness (Yellow)

| Tested Properties | Test Method | Hydrolyzed Keratin Absent | Hydrolyzed Keratin Present | Difference* |
|---|---|---|---|---|
| Light Resistance | JIS L 0842 | 4.5 | 4.5 | +0.5 |
| Wash Resistance | JIS L 0844 (A-2) | 4.5 | 4.5 | 0 |
| Wash Contamination | ditto | 4.5 | 4.5 | 0 |
| Migration by Sweat (Acid) | JIS L 0848 | 3.0 | 4.0 | +1.0 |
| Migration by Sweat (Alkali) | ditto | 2.5 | 3.0 | +0.5 |
| Friction Resistance (Dry) | JIS L 0849 (II) | 4.5 | 4.5 | 0 |
| Dry Cleaning Contamination | JIS L 0860 (A-1) | 4.0 | 4.5 | +0.5 |

*Difference indicates one in class.

TABLE 9

Dyeing Color-Fastness (Red)

| Tested Properties | Test Method | Hydrolyzed Keratin Absent | Hydrolyzed Keratin Present | Difference* |
|---|---|---|---|---|
| Light Resistance | JIS L 0842 | 4.5 | 4.5 | 0 |
| Wash Resistance | JIS L 0844 (A-2) | 4.0 | 4.5 | +0.5 |
| Wash Contamination | ditto | 4.5 | 4.5 | 0 |
| Migration by Sweat (Acid) | JIS L 0848 | 3.0 | 4.0 | +1.0 |
| Migration by Sweat (Alkali) | ditto | 2.5 | 3.5 | +1.0 |
| Friction Resistance (Dry) | JIS L 0849 (II) | 4.0 | 4.5 | +0.5 |
| Dry Cleaning Contamination | JIS L 0860 (A-1) | 4.0 | 4.5 | +0.5 |

*Difference indicates one in class.

TABLE 10

Dyeing Color-Fastness (Black)

| Tested Properties | Test Method | Hydrolyzed Keratin Absent | Hydrolyzed Keratin Present | Difference* |
|---|---|---|---|---|
| Light Resistance | JIS L 0842 | 4.5 | 4.5 | 0 |
| Wash Resistance | JIS L 0844 (A-2) | 4.5 | 4.5 | 0 |
| Wash Contamination | ditto | 3.5 | 4.0 | +0.5 |
| Migration by Sweat (Acid) | JIS L 0848 | 1.5 | 2.5 | +1.0 |
| Migration by Sweat (Alkali) | ditto | 1.5 | 2.5 | +1.0 |
| Friction Resistance (Dry) | JIS L 0849 (II) | 3.5 | 4.0 | +0.5 |
| Dry Cleaning Contamination | JIS L 0860 (A-1) | 4.5 | 4.5 | 0 |

*Difference indicates one in class.

The meaning of each tested properties is described. The light resistance indicates the resistance to light, and the wash resistance indicates the resistance to washing. The wash contamination indicates the migration of color into the surrounding white portion of the fabrics due to washing. The migration by sweat (acid) indicates the degree of color migration into the surrounding white portion by acidic artificial sweat, and the migration by sweat (alkali) indicates the degree of color migration into the surrounding white portion by alkaline artificial sweat. The friction resistance indicates the migration of color between dyed knitted fabrics and white fabrics due to friction between them in a dry condition. The dry cleaning contamination indicates the degree of dissolution of dyestuff into the perfluoro-ethylene solvent used for dry-cleaning. The classes of these dyeing color-fastness are higher when good results are gotten, and, practically, at least class 2.5 or more is necessary.

The hydrolyzed keratin treatment improved the dyeing color-fastness, and the insufficiency in the tested properties is removed. Regarding black dye, the migrations by sweat (both acid and alkali) are improved to class 2.5 from class 1.5. The improvement in the dyeing color-fastness shows that the water-birds feather derived hydrolyzed keratin improves the connection strength between the dyestuff and the fiber.

What is claimed is:

1. A crimping method comprising:
a step for immersing protein fiber having crimp property such that the protein fiber crimps in response to a stimulus, in a solution of protein having a different composition from the protein fiber; and
a step for infiltrating said protein having the different composition into said protein fiber and crimping said protein fiber; wherein
said protein is artificial spider silk protein; and
said solution of protein is an aqueous solution of hydrolyzed keratin having a number averaged molecular weight not less than 500 and not more than 5000.

2. The crimping method of claim 1, wherein staples of filaments of said protein fiber are immersed in said solution of protein.

3. The crimping method of claim 2, wherein spun yarn made of said staples twisted together is immersed in said solution of protein.

4. The crimping method of claim 3, wherein a textile product made of said spun yarn is immersed in said solution of protein, said staples in the textile product are made crimped, and the textile product is fulled.

5. The crimping method of claim 4, wherein said textile product is immersed in said solution of protein under a condition that impact is not applied to said textile product.

6. The crimping method of claim 1, wherein concentration of said hydrolyzed keratin before immersing said textile product is not less than 0.1 mass % and not more than 2 mass % and an immersing period of said textile product is not less than 5 minutes and not more than 120 minutes.

7. The crimping method of claim 1, wherein said aqueous solution of hydrolyzed keratin is at a temperature range of 30 degree Celsius to 60 degree Celsius.

8. The crimping method of claim 1, wherein dyeing affinity of said protein fiber is made improved by said protein having the different composition.

9. The crimping method of claim 1, wherein said protein fiber is immersed in the aqueous solution of said hydrolyzed keratin for at least 40 minutes and utmost 80 minutes.

* * * * *

```
                              SEQUENCE LISTING

<160> NUMBER OF SEQ ID NOS: 41

<210> SEQ ID NO 1
<211> LENGTH: 597
<212> TYPE: PRT
<213> ORGANISM: Artificial Sequence
<220> FEATURE:
<223> OTHER INFORMATION: Met-PRT313

<400> SEQUENCE: 1

Met Gly Pro Gly Gly Gln Gly Pro Tyr Gly Pro Gly Ala Ser Ala Ala
1               5                   10                  15

Ala Ala Ala Gly Gly Asn Gly Pro Gly Ser Gly Gln Gln Gly Pro Gly
            20                  25                  30

Gly Ser Ala Ala Ala Ala Gly Gly Tyr Gly Pro Gly Gly Gln Gly
        35                  40                  45

Pro Gly Gln Gln Gly Pro Gly Ser Ser Ala Ala Ala Ala Gly Pro
    50                  55                  60

Gly Gly Tyr Gly Pro Gly Gly Gln Gly Pro Ser Ala Ser Ala Ala Ala
65                  70                  75                  80

Ala Ala Gly Pro Gly Ser Gly Gln Gln Gly Pro Gly Ala Ser Ala Ala
                85                  90                  95

Ala Ala Ala Gly Gly Tyr Gly Pro Gly Gly Gln Gly Pro Gly Gln Gln
            100                 105                 110

Gly Pro Gly Ser Ser Ala Ala Ala Ala Gly Gly Tyr Gly Ser Gly
        115                 120                 125

Pro Gly Gln Gln Gly Pro Tyr Gly Ser Ala Ala Ala Ala Gly Pro
    130                 135                 140

Gly Ser Gly Gly Tyr Gly Gln Gly Pro Tyr Gly Pro Gly Ala Ser Ala
145                 150                 155                 160

Ala Ala Ala Gly Pro Gly Gly Tyr Gly Pro Gly Gly Gln Gly Pro
            165                 170                 175

Ser Ala Ser Ala Ala Ala Ala Gly Ser Gly Gln Gln Gly Pro Gly
        180                 185                 190

Gly Tyr Gly Pro Tyr Ala Ser Ala Ala Ala Ala Gly Gly Tyr Gly
    195                 200                 205

Ser Gly Pro Gly Gln Gln Gly Pro Tyr Gly Pro Gly Gly Ser Ala Ala
        210                 215                 220

Ala Ala Ala Gly Ser Gly Gln Gln Gly Pro Gly Gln Gln Gly Pro Tyr
225                 230                 235                 240

Ala Ser Ala Ala Ala Ala Gly Pro Gly Gly Gln Gly Pro Tyr Gly
            245                 250                 255

Pro Gly Ser Ser Ala Ala Ala Ala Gly Gly Tyr Gly Tyr Gly Pro
        260                 265                 270

Gly Gly Gln Gly Pro Tyr Gly Pro Gly Ala Ser Ala Ala Ala Ala
    275                 280                 285

Gly Gly Asn Gly Pro Gly Ser Gly Tyr Gly Pro Gly Gln Gln Gly
        290                 295                 300

Pro Gly Gly Ser Ala Ala Ala Ala Ala Gly Pro Gly Gly Gln Gly Pro
305                 310                 315                 320
```

-continued

Tyr Gly Pro Gly Ala Ser Ala Ala Ala Ala Gly Gly Tyr Gly Pro
                325                 330                 335

Gly Gly Gln Gly Pro Gly Gly Tyr Gly Pro Gly Ser Ser Ala Ala
            340                 345                 350

Ala Ala Gly Pro Gly Gly Gln Gly Pro Tyr Gly Pro Gly Ser Ser Ala
            355                 360                 365

Ala Ala Ala Ala Gly Gly Tyr Gly Pro Gly Gln Gln Gly Pro Tyr Gly
            370                 375                 380

Pro Gly Gly Ser Ala Ala Ala Ala Gly Gly Tyr Gln Gln Gly Pro
385                 390                 395                 400

Gly Gly Gln Gly Pro Tyr Gly Pro Gly Ala Ser Ala Ala Ala Ala
                405                 410                 415

Gly Pro Gly Gly Gln Gly Pro Tyr Gly Pro Gly Ala Ser Ala Ala
            420                 425                 430

Ala Ala Gly Pro Gly Gly Tyr Gly Pro Gly Gly Gln Gly Pro Ser Ala
            435                 440                 445

Ser Ala Ala Ala Ala Gly Gly Tyr Gly Ser Gly Pro Gly Gly Tyr
    450                 455                 460

Gly Pro Tyr Gly Pro Gly Gly Ser Ala Ala Ala Ala Gly Pro Gly
465                 470                 475                 480

Ser Gly Gln Gln Gly Gln Gly Pro Tyr Gly Pro Gly Ala Ser Ala Ala
            485                 490                 495

Ala Ala Ala Gly Gly Tyr Gly Pro Gly Gln Gln Gly Pro Tyr Gly Pro
            500                 505                 510

Gly Gly Ser Ala Ala Ala Ala Gly Pro Gly Ser Gly Gly Tyr Gly
            515                 520                 525

Pro Gly Ala Ser Ala Ala Ala Ala Gly Gly Asn Gly Pro Gly Ser
            530                 535                 540

Gly Gly Tyr Gly Pro Gly Gln Gln Gly Pro Gly Gly Ser Ala Ala Ala
545                 550                 555                 560

Ala Ala Gly Gly Tyr Gln Gln Gly Pro Gly Gly Gln Gly Pro Tyr Gly
            565                 570                 575

Pro Gly Ala Ser Ala Ala Ala Ala Gly Pro Gly Ser Gly Gln Gln
            580                 585                 590

Gly Pro Gly Ala Ser
        595

<210> SEQ ID NO 2
<211> LENGTH: 590
<212> TYPE: PRT
<213> ORGANISM: Artificial Sequence
<220> FEATURE:
<223> OTHER INFORMATION: Met-PRT399

<400> SEQUENCE: 2

Met Gly Pro Gly Gly Gln Gly Pro Tyr Gly Pro Gly Ala Ser Ala Ala
1               5                   10                  15

Ala Ala Ala Gly Gly Asn Gly Pro Gly Ser Gly Gln Gln Gly Pro Gly
                20                  25                  30

Gly Ser Gly Gly Tyr Gly Pro Gly Gln Gly Pro Gly Gln Gln Gly
            35                  40                  45

Pro Gly Ser Ser Ala Ala Ala Ala Gly Pro Gly Gly Tyr Gly Pro
    50                  55                  60

Gly Gly Gln Gly Pro Ser Ala Ser Ala Ala Ala Ala Gly Pro Gly
65                  70                  75                  80

```
Ser Gly Gln Gln Gly Pro Ala Ser Gly Tyr Gly Pro Gly Gly
                85                  90                  95

Gln Gly Pro Gly Gln Gln Gly Pro Gly Ser Ser Ala Ala Ala Ala Ala
            100                 105                 110

Gly Gly Tyr Gly Ser Gly Pro Gly Gln Gln Gly Pro Tyr Gly Ser Ala
            115                 120                 125

Ala Ala Ala Ala Gly Pro Gly Ser Gly Gly Tyr Gly Gln Gly Pro Tyr
130                 135                 140

Gly Pro Gly Ala Ser Gly Pro Gly Gly Tyr Gly Pro Gly Gly Gln Gly
145                 150                 155                 160

Pro Ser Ala Ser Ala Ala Ala Ala Ala Gly Ser Gly Gln Gln Gly Pro
                165                 170                 175

Gly Gly Tyr Gly Pro Tyr Ala Ser Ala Ala Ala Ala Gly Gly Tyr
            180                 185                 190

Gly Ser Gly Pro Gly Gln Gln Gly Pro Tyr Gly Pro Gly Gly Ser Gly
            195                 200                 205

Ser Gly Gln Gln Gly Pro Gly Gln Gln Gly Pro Tyr Ala Ser Ala Ala
            210                 215                 220

Ala Ala Ala Gly Pro Gly Gln Gly Pro Tyr Gly Pro Gly Ser Ser
225                 230                 235                 240

Ala Ala Ala Ala Ala Gly Gly Tyr Gly Tyr Gly Pro Gly Gln Gly
                245                 250                 255

Pro Tyr Gly Pro Gly Ala Ser Gly Gly Asn Gly Pro Gly Ser Gly Gly
            260                 265                 270

Tyr Gly Pro Gly Gln Gln Gly Pro Gly Gly Ser Ala Ala Ala Ala Ala
            275                 280                 285

Gly Pro Gly Gly Gln Gly Pro Tyr Gly Pro Gly Ala Ser Ala Ala Ala
290                 295                 300

Ala Ala Gly Gly Tyr Gly Pro Gly Gln Gly Pro Gly Gly Tyr Gly
305                 310                 315                 320

Pro Gly Ser Ser Gly Pro Gly Gln Gly Pro Tyr Gly Pro Gly Ser
            325                 330                 335

Ser Ala Ala Ala Ala Ala Gly Gly Tyr Gly Pro Gly Gln Gln Gly Pro
                340                 345                 350

Tyr Gly Pro Gly Gly Ser Ala Ala Ala Ala Gly Gly Tyr Gln Gln
            355                 360                 365

Gly Pro Gly Gly Gln Gly Pro Tyr Gly Pro Gly Ala Ser Gly Pro Gly
370                 375                 380

Gly Gln Gly Pro Tyr Gly Pro Gly Ala Ser Ala Ala Ala Ala Gly
385                 390                 395                 400

Pro Gly Gly Tyr Gly Pro Gly Gln Gly Pro Ser Ala Ser Ala Ala
            405                 410                 415

Ala Ala Ala Gly Gly Tyr Gly Ser Gly Pro Gly Gly Tyr Gly Pro Tyr
                420                 425                 430

Gly Pro Gly Gly Ser Gly Pro Gly Ser Gly Gln Gln Gly Gln Gly Pro
            435                 440                 445

Tyr Gly Pro Gly Ala Ser Ala Ala Ala Ala Gly Gly Tyr Gly Pro
450                 455                 460

Gly Gln Gln Gly Pro Tyr Gly Pro Gly Ser Ala Ala Ala Ala Ala
465                 470                 475                 480

Gly Pro Gly Ser Gly Gly Tyr Gly Pro Gly Ala Ser Gly Gly Asn Gly
                485                 490                 495
```

```
Pro Gly Ser Gly Gly Tyr Gly Pro Gly Gln Gln Gly Pro Gly Gly Ser
                500                 505                 510

Ala Ala Ala Ala Ala Gly Gly Tyr Gln Gln Gly Pro Gly Gly Gln Gly
            515                 520                 525

Pro Tyr Gly Pro Gly Ala Ser Ala Ala Ala Ala Gly Gly Tyr Gly
        530                 535                 540

Ser Gly Pro Gly Gln Gln Gly Pro Tyr Gly Pro Gly Ser Gly Ser
545                 550                 555                 560

Gly Gln Gln Gly Pro Gly Gln Gln Gly Pro Tyr Ala Ser Ala Ala Ala
                565                 570                 575

Ala Ala Gly Pro Gly Ser Gly Gln Gln Gly Pro Gly Ala Ser
            580                 585                 590
```

<210> SEQ ID NO 3
<211> LENGTH: 597
<212> TYPE: PRT
<213> ORGANISM: Artificial Sequence
<220> FEATURE:
<223> OTHER INFORMATION: Met-PRT380

<400> SEQUENCE: 3

```
Met Gly Pro Gly Gln Gln Gly Pro Tyr Gly Pro Gly Ala Ser Ala Ala
1               5                   10                  15

Ala Ala Ala Gly Gln Asn Gly Pro Gly Ser Gly Gln Gln Gly Pro Gly
                20                  25                  30

Gln Ser Ala Ala Ala Ala Ala Gly Gln Tyr Gly Pro Gly Gln Gln Gly
            35                  40                  45

Pro Gly Gln Gln Gly Pro Gly Ser Ser Ala Ala Ala Ala Ala Gly Pro
50                  55                  60

Gly Gln Tyr Gly Pro Gly Gln Gln Gly Pro Ser Ala Ser Ala Ala Ala
65                  70                  75                  80

Ala Ala Gly Pro Gly Ser Gly Gln Gln Gly Pro Gly Ala Ser Ala Ala
                85                  90                  95

Ala Ala Ala Gly Gln Tyr Gly Pro Gly Gln Gln Gly Pro Gly Gln Gln
                100                 105                 110

Gly Pro Gly Ser Ser Ala Ala Ala Ala Ala Gly Gln Tyr Gly Ser Gly
            115                 120                 125

Pro Gly Gln Gln Gly Pro Tyr Gly Ser Ala Ala Ala Ala Ala Gly Pro
130                 135                 140

Gly Ser Gly Gln Tyr Gly Gln Gly Pro Tyr Gly Pro Gly Ala Ser Ala
145                 150                 155                 160

Ala Ala Ala Ala Gly Pro Gly Gln Tyr Gly Pro Gly Gln Gln Gly Pro
                165                 170                 175

Ser Ala Ser Ala Ala Ala Ala Gly Ser Gly Gln Gln Gly Pro Gly
            180                 185                 190

Gln Tyr Gly Pro Tyr Ala Ser Ala Ala Ala Ala Gly Gln Tyr Gly
            195                 200                 205

Ser Gly Pro Gly Gln Gln Gly Pro Tyr Gly Pro Gly Gln Ser Ala Ala
            210                 215                 220

Ala Ala Ala Gly Ser Gly Gln Gln Gly Pro Gly Gln Gln Gly Pro Tyr
225                 230                 235                 240

Ala Ser Ala Ala Ala Ala Ala Gly Pro Gly Gln Gln Gly Pro Tyr Gly
                245                 250                 255

Pro Gly Ser Ser Ala Ala Ala Ala Ala Gly Gln Tyr Gly Tyr Gly Pro
                260                 265                 270
```

```
Gly Gln Gln Gly Pro Tyr Gly Pro Gly Ala Ser Ala Ala Ala Ala
            275                 280                 285

Gly Gln Asn Gly Pro Gly Ser Gly Gln Tyr Gly Pro Gly Gln Gln Gly
            290                 295                 300

Pro Gly Gln Ser Ala Ala Ala Ala Gly Pro Gly Gln Gln Gly Pro
305                 310                 315                 320

Tyr Gly Pro Gly Ala Ser Ala Ala Ala Ala Gly Gln Tyr Gly Pro
                325                 330                 335

Gly Gln Gln Gly Pro Gly Gln Tyr Pro Gly Ser Ser Ala Ala
            340                 345                 350

Ala Ala Gly Pro Gly Gln Gln Gly Pro Tyr Gly Pro Gly Ser Ser Ala
            355                 360                 365

Ala Ala Ala Ala Gly Gln Tyr Gly Pro Gly Gln Gln Gly Pro Tyr Gly
            370                 375                 380

Pro Gly Gln Ser Ala Ala Ala Ala Gly Gln Tyr Gln Gln Gly Pro
385                 390                 395                 400

Gly Gln Gln Gly Pro Tyr Gly Pro Gly Ala Ser Ala Ala Ala Ala
            405                 410                 415

Gly Pro Gly Gln Gln Gly Pro Tyr Gly Pro Gly Ala Ser Ala Ala
            420                 425                 430

Ala Ala Gly Pro Gly Gln Tyr Gly Pro Gly Gln Gln Gly Pro Ser Ala
            435                 440                 445

Ser Ala Ala Ala Ala Gly Gln Tyr Gly Ser Gly Pro Gly Gln Tyr
            450                 455                 460

Gly Pro Tyr Gly Pro Gly Gln Ser Ala Ala Ala Ala Gly Pro Gly
465                 470                 475                 480

Ser Gly Gln Gln Gly Gln Gly Pro Tyr Gly Pro Gly Ala Ser Ala Ala
            485                 490                 495

Ala Ala Ala Gly Gln Tyr Gly Pro Gly Gln Gln Gly Pro Tyr Gly Pro
            500                 505                 510

Gly Gln Ser Ala Ala Ala Ala Gly Pro Gly Ser Gly Gln Tyr Gly
            515                 520                 525

Pro Gly Ala Ser Ala Ala Ala Ala Gly Gln Asn Gly Pro Gly Ser
530                 535                 540

Gly Gln Tyr Gly Pro Gly Gln Gly Pro Gly Gln Ser Ala Ala Ala
545                 550                 555                 560

Ala Ala Gly Gln Tyr Gln Gln Gly Pro Gly Gln Gln Gly Pro Tyr Gly
            565                 570                 575

Pro Gly Ala Ser Ala Ala Ala Ala Gly Pro Gly Ser Gly Gln Gln
            580                 585                 590

Gly Pro Gly Ala Ser
        595

<210> SEQ ID NO 4
<211> LENGTH: 590
<212> TYPE: PRT
<213> ORGANISM: Artificial Sequence
<220> FEATURE:
<223> OTHER INFORMATION: Met-PRT410

<400> SEQUENCE: 4

Met Gly Pro Gly Gln Gln Gly Pro Tyr Gly Pro Gly Ala Ser Ala Ala
1               5                   10                  15

Ala Ala Ala Gly Gln Asn Gly Pro Gly Ser Gly Gln Gln Gly Pro Gly
            20                  25                  30
```

-continued

Gln Ser Gly Gln Tyr Gly Pro Gly Gln Gln Gly Pro Gly Gln Gln Gly
                35                  40                  45

Pro Gly Ser Ser Ala Ala Ala Ala Gly Pro Gly Gln Tyr Gly Pro
 50                  55                  60

Gly Gln Gln Gly Pro Ser Ala Ser Ala Ala Ala Ala Gly Pro Gly
 65                  70                  75                  80

Ser Gly Gln Gln Gly Pro Gly Ala Ser Gly Gln Tyr Gly Pro Gly Gln
                85                  90                  95

Gln Gly Pro Gly Gln Gln Gly Pro Gly Ser Ser Ala Ala Ala Ala
            100                 105                 110

Gly Gln Tyr Gly Ser Gly Pro Gly Gln Gly Pro Tyr Gly Ser Ala
            115                 120                 125

Ala Ala Ala Ala Gly Pro Gly Ser Gly Gln Tyr Gly Gln Gly Pro Tyr
            130                 135                 140

Gly Pro Gly Ala Ser Gly Pro Gly Gln Tyr Gly Pro Gly Gln Gln Gly
145                 150                 155                 160

Pro Ser Ala Ser Ala Ala Ala Ala Gly Ser Gly Gln Gln Gly Pro
            165                 170                 175

Gly Gln Tyr Gly Pro Tyr Ala Ser Ala Ala Ala Ala Gly Gln Tyr
            180                 185                 190

Gly Ser Gly Pro Gly Gln Gly Pro Tyr Gly Pro Gly Ser Gly
            195                 200                 205

Ser Gly Gln Gln Gly Pro Gly Gln Gln Gly Pro Tyr Ala Ser Ala Ala
            210                 215                 220

Ala Ala Ala Gly Pro Gly Gln Gln Gly Pro Tyr Gly Pro Gly Ser Ser
225                 230                 235                 240

Ala Ala Ala Ala Ala Gly Gln Tyr Gly Tyr Gly Pro Gly Gln Gln Gly
            245                 250                 255

Pro Tyr Gly Pro Gly Ala Ser Gly Gln Asn Gly Pro Gly Ser Gly Gln
            260                 265                 270

Tyr Gly Pro Gly Gln Gln Gly Pro Gly Gln Ser Ala Ala Ala Ala
            275                 280                 285

Gly Pro Gly Gln Gln Gly Pro Tyr Gly Pro Gly Ala Ser Ala Ala Ala
            290                 295                 300

Ala Ala Gly Gln Tyr Gly Pro Gly Gln Gly Pro Gly Gln Tyr Gly
305                 310                 315                 320

Pro Gly Ser Ser Gly Pro Gly Gln Gln Gly Pro Tyr Gly Pro Gly Ser
            325                 330                 335

Ser Ala Ala Ala Ala Gly Gln Tyr Gly Pro Gly Gln Gln Gly Pro
            340                 345                 350

Tyr Gly Pro Gly Gln Ser Ala Ala Ala Ala Gly Gln Tyr Gln Gln
            355                 360                 365

Gly Pro Gly Gln Gln Gly Pro Tyr Gly Pro Gly Ala Ser Gly Pro Gly
            370                 375                 380

Gln Gln Gly Pro Tyr Gly Pro Gly Ala Ser Ala Ala Ala Ala Gly
385                 390                 395                 400

Pro Gly Gln Tyr Gly Pro Gly Gln Gln Gly Pro Ser Ala Ser Ala
            405                 410                 415

Ala Ala Ala Gly Gln Tyr Gly Ser Gly Pro Gly Gln Tyr Gly Pro Tyr
            420                 425                 430

Gly Pro Gly Gln Ser Gly Pro Gly Ser Gly Gln Gln Gly Gln Gly Pro
            435                 440                 445

Tyr Gly Pro Gly Ala Ser Ala Ala Ala Ala Gly Gln Tyr Gly Pro

```
                    450                 455                 460
Gly Gln Gln Gly Pro Tyr Pro Gly Gln Ser Ala Ala Ala Ala
465                 470                 475                 480

Gly Pro Gly Ser Gly Gln Tyr Gly Pro Gly Ala Ser Gly Asn Gly
                485                 490                 495

Pro Gly Ser Gly Gln Tyr Gly Pro Gly Gln Gln Gly Pro Gly Gln Ser
                500                 505                 510

Ala Ala Ala Ala Ala Gly Gln Tyr Gln Gln Gly Pro Gln Gln Gly
            515                 520                 525

Pro Tyr Gly Pro Gly Ala Ser Ala Ala Ala Ala Gly Gln Tyr Gly
        530                 535                 540

Ser Gly Pro Gly Gln Gln Gly Pro Tyr Gly Pro Gly Gln Ser Gly Ser
545                 550                 555                 560

Gly Gln Gln Gly Pro Gln Gln Gly Pro Tyr Ala Ser Ala Ala Ala
                565                 570                 575

Ala Ala Gly Pro Gly Ser Gly Gln Gln Gly Pro Gly Ala Ser
            580                 585                 590

<210> SEQ ID NO 5
<211> LENGTH: 12
<212> TYPE: PRT
<213> ORGANISM: Artificial Sequence
<220> FEATURE:
<223> OTHER INFORMATION: HisTag

<400> SEQUENCE: 5

Met His His His His His His Ser Ser Gly Ser Ser
1               5                   10

<210> SEQ ID NO 6
<211> LENGTH: 608
<212> TYPE: PRT
<213> ORGANISM: Artificial Sequence
<220> FEATURE:
<223> OTHER INFORMATION: PRT313

<400> SEQUENCE: 6

Met His His His His His His Ser Ser Gly Ser Ser Gly Pro Gly Gly
1               5                   10                  15

Gln Gly Pro Tyr Gly Pro Gly Ala Ser Ala Ala Ala Ala Gly Gly
            20                  25                  30

Asn Gly Pro Gly Ser Gly Gln Gln Gly Pro Gly Gly Ser Ala Ala
        35                  40                  45

Ala Ala Gly Gly Tyr Gly Pro Gly Gly Gln Gly Pro Gly Gln Gln Gly
    50                  55                  60

Pro Gly Ser Ser Ala Ala Ala Ala Ala Gly Pro Gly Tyr Gly Pro
65                  70                  75                  80

Gly Gly Gln Gly Pro Ser Ala Ser Ala Ala Ala Ala Gly Pro Gly
                85                  90                  95

Ser Gly Gln Gln Gly Pro Gly Ala Ser Ala Ala Ala Ala Gly Gly
            100                 105                 110

Tyr Gly Pro Gly Gly Gln Gly Pro Gly Gln Gln Gly Pro Gly Ser Ser
        115                 120                 125

Ala Ala Ala Ala Ala Gly Gly Tyr Gly Ser Gly Pro Gly Gln Gln Gly
    130                 135                 140

Pro Tyr Gly Ser Ala Ala Ala Ala Ala Gly Pro Gly Ser Gly Gly Tyr
145                 150                 155                 160
```

-continued

```
Gly Gln Gly Pro Tyr Gly Pro Gly Ala Ser Ala Ala Ala Ala Gly
                165                 170                 175
Pro Gly Gly Tyr Gly Pro Gly Gln Gly Pro Ser Ala Ser Ala Ala
                180                 185                 190
Ala Ala Ala Gly Ser Gly Gln Gln Gly Pro Gly Gly Tyr Gly Pro Tyr
            195                 200                 205
Ala Ser Ala Ala Ala Ala Ala Gly Gly Tyr Gly Ser Gly Pro Gly Gln
            210                 215                 220
Gln Gly Pro Tyr Gly Pro Gly Ser Ala Ala Ala Ala Gly Ser
225                 230                 235                 240
Gly Gln Gln Gly Pro Gln Gln Gly Pro Tyr Ala Ser Ala Ala
                245                 250                 255
Ala Ala Gly Pro Gly Gly Gln Gly Pro Tyr Gly Pro Gly Ser Ser Ala
                260                 265                 270
Ala Ala Ala Ala Gly Gly Tyr Gly Tyr Gly Pro Gly Gly Gln Gly Pro
            275                 280                 285
Tyr Gly Pro Gly Ala Ser Ala Ala Ala Ala Gly Gly Asn Gly Pro
            290                 295                 300
Gly Ser Gly Gly Tyr Gly Pro Gly Gln Gln Gly Pro Gly Gly Ser Ala
305                 310                 315                 320
Ala Ala Ala Gly Pro Gly Gln Gly Pro Tyr Gly Pro Gly Ala
                325                 330                 335
Ser Ala Ala Ala Ala Gly Gly Tyr Gly Pro Gly Gly Gln Gly Pro
            340                 345                 350
Gly Gly Tyr Gly Pro Gly Ser Ser Ala Ala Ala Ala Gly Pro Gly
            355                 360                 365
Gly Gln Gly Pro Tyr Gly Pro Gly Ser Ser Ala Ala Ala Ala Gly
            370                 375                 380
Gly Tyr Gly Pro Gly Gln Gln Gly Pro Tyr Gly Pro Gly Ser Ala
385                 390                 395                 400
Ala Ala Ala Gly Gly Tyr Gln Gln Gly Pro Gly Gly Gln Gly Pro
                405                 410                 415
Tyr Gly Pro Gly Ala Ser Ala Ala Ala Ala Gly Pro Gly Gly Gln
            420                 425                 430
Gly Pro Tyr Gly Pro Gly Ala Ser Ala Ala Ala Ala Gly Pro Gly
            435                 440                 445
Gly Tyr Gly Pro Gly Gly Gln Gly Pro Ser Ala Ser Ala Ala Ala
            450                 455                 460
Ala Gly Gly Tyr Gly Ser Gly Pro Gly Gly Tyr Gly Pro Tyr Gly Pro
465                 470                 475                 480
Gly Gly Ser Ala Ala Ala Ala Gly Pro Gly Ser Gly Gln Gln Gly
                485                 490                 495
Gln Gly Pro Tyr Gly Pro Gly Ala Ser Ala Ala Ala Ala Gly Gly
                500                 505                 510
Tyr Gly Pro Gly Gln Gln Gly Pro Tyr Gly Pro Gly Gly Ser Ala Ala
            515                 520                 525
Ala Ala Ala Gly Pro Gly Ser Gly Gly Tyr Gly Pro Gly Ala Ser Ala
            530                 535                 540
Ala Ala Ala Gly Gly Asn Gly Pro Gly Ser Gly Gly Tyr Gly Pro
545                 550                 555                 560
Gly Gln Gln Gly Pro Gly Gly Ser Ala Ala Ala Ala Gly Gly Tyr
                565                 570                 575
Gln Gln Gly Pro Gly Gly Gln Gly Pro Tyr Gly Pro Gly Ala Ser Ala
```

-continued

```
                580                 585                 590
Ala Ala Ala Ala Gly Pro Gly Ser Gly Gln Gln Gly Pro Gly Ala Ser
            595                 600                 605

<210> SEQ ID NO 7
<211> LENGTH: 601
<212> TYPE: PRT
<213> ORGANISM: Artificial Sequence
<220> FEATURE:
<223> OTHER INFORMATION: PRT399

<400> SEQUENCE: 7

Met His His His His His Ser Ser Gly Ser Ser Gly Pro Gly Gly
1               5                   10                  15

Gln Gly Pro Tyr Gly Pro Gly Ala Ser Ala Ala Ala Ala Gly Gly
                20                  25                  30

Asn Gly Pro Gly Ser Gly Gln Gln Gly Pro Gly Gly Ser Gly Gly Tyr
                35                  40                  45

Gly Pro Gly Gly Gln Gly Pro Gly Gln Gln Gly Pro Gly Ser Ser Ala
            50                  55                  60

Ala Ala Ala Ala Gly Pro Gly Gly Tyr Gly Pro Gly Gln Gly Pro
65                  70                  75                  80

Ser Ala Ser Ala Ala Ala Ala Gly Pro Gly Ser Gly Gln Gln Gly
                85                  90                  95

Pro Gly Ala Ser Gly Gly Tyr Gly Pro Gly Gln Gly Pro Gly Gln
                100                 105                 110

Gln Gly Pro Gly Ser Ser Ala Ala Ala Ala Gly Gly Tyr Gly Ser
                115                 120                 125

Gly Pro Gly Gln Gln Gly Pro Tyr Gly Ser Ala Ala Ala Ala Gly
            130                 135                 140

Pro Gly Ser Gly Gly Tyr Gly Gln Gly Pro Tyr Gly Pro Gly Ala Ser
145                 150                 155                 160

Gly Pro Gly Gly Tyr Gly Pro Gly Gly Gln Gly Pro Ser Ala Ser Ala
                165                 170                 175

Ala Ala Ala Gly Ser Gly Gln Gln Gly Pro Gly Gly Tyr Gly Pro
                180                 185                 190

Tyr Ala Ser Ala Ala Ala Ala Gly Gly Tyr Gly Ser Gly Pro Gly
            195                 200                 205

Gln Gln Gly Pro Tyr Gly Pro Gly Ser Gly Ser Gly Gln Gln Gly
            210                 215                 220

Pro Gly Gln Gln Gly Pro Tyr Ala Ser Ala Ala Ala Ala Gly Pro
225                 230                 235                 240

Gly Gly Gln Gly Pro Tyr Gly Pro Gly Ser Ser Ala Ala Ala Ala
                245                 250                 255

Gly Gly Tyr Gly Tyr Gly Pro Gly Gly Gln Gly Pro Tyr Gly Pro Gly
                260                 265                 270

Ala Ser Gly Gly Asn Pro Gly Ser Gly Gly Tyr Gly Pro Gly Gln
            275                 280                 285

Gln Gly Pro Gly Gly Ser Ala Ala Ala Ala Gly Pro Gly Gly Gln
            290                 295                 300

Gly Pro Tyr Gly Pro Gly Ala Ser Ala Ala Ala Ala Gly Gly Tyr
305                 310                 315                 320

Gly Pro Gly Gly Gln Gly Pro Gly Gly Tyr Gly Pro Gly Ser Ser Gly
                325                 330                 335

Pro Gly Gly Gln Gly Pro Tyr Gly Pro Gly Ser Ser Ala Ala Ala Ala
```

```
            340                 345                 350
Ala Gly Gly Tyr Gly Pro Gly Gln Gln Gly Pro Tyr Gly Pro Gly Gly
                355                 360                 365

Ser Ala Ala Ala Ala Gly Gly Tyr Gln Gln Gly Pro Gly Gly Gln
    370                 375                 380

Gly Pro Tyr Gly Pro Gly Ala Ser Gly Pro Gly Gln Gly Pro Tyr
385                 390                 395                 400

Gly Pro Gly Ala Ser Ala Ala Ala Ala Gly Pro Gly Gly Tyr Gly
                405                 410                 415

Pro Gly Gly Gln Gly Pro Ser Ala Ser Ala Ala Ala Ala Gly Gly
                420                 425                 430

Tyr Gly Ser Gly Pro Gly Gly Tyr Gly Pro Tyr Gly Pro Gly Gly Ser
                435                 440                 445

Gly Pro Gly Ser Gly Gln Gln Gly Gln Gly Pro Tyr Gly Pro Gly Ala
                450                 455                 460

Ser Ala Ala Ala Ala Gly Gly Tyr Gly Pro Gly Gln Gln Gly Pro
465                 470                 475                 480

Tyr Gly Pro Gly Gly Ser Ala Ala Ala Ala Gly Pro Gly Ser Gly
                485                 490                 495

Gly Tyr Gly Pro Gly Ala Ser Gly Gly Asn Gly Pro Gly Ser Gly Gly
                500                 505                 510

Tyr Gly Pro Gly Gln Gln Gly Pro Gly Gly Ser Ala Ala Ala Ala
                515                 520                 525

Gly Gly Tyr Gln Gln Gly Pro Gly Gln Gly Pro Tyr Gly Pro Gly
                530                 535                 540

Ala Ser Ala Ala Ala Ala Gly Gly Tyr Gly Ser Gly Pro Gly Gln
545                 550                 555                 560

Gln Gly Pro Tyr Gly Pro Gly Gly Ser Gly Ser Gly Gln Gln Gly Pro
                565                 570                 575

Gly Gln Gln Gly Pro Tyr Ala Ser Ala Ala Ala Ala Gly Pro Gly
                580                 585                 590

Ser Gly Gln Gln Gly Pro Gly Ala Ser
            595                 600

<210> SEQ ID NO 8
<211> LENGTH: 608
<212> TYPE: PRT
<213> ORGANISM: Artificial Sequence
<220> FEATURE:
<223> OTHER INFORMATION: PRT380

<400> SEQUENCE: 8

Met His His His His His Ser Ser Gly Ser Gly Pro Gly Gln
1               5                   10                  15

Gln Gly Pro Tyr Gly Pro Gly Ala Ser Ala Ala Ala Ala Gly Gln
                20                  25                  30

Asn Gly Pro Gly Ser Gly Gln Gln Gly Pro Gly Gln Ser Ala Ala
            35                  40                  45

Ala Ala Gly Gln Tyr Gly Pro Gly Gln Gly Pro Gly Gln Gln Gly
    50                  55                  60

Pro Gly Ser Ser Ala Ala Ala Ala Gly Pro Gly Gln Tyr Gly Pro
65                  70                  75                  80

Gly Gln Gln Gly Pro Ser Ala Ser Ala Ala Ala Ala Gly Pro Gly
                85                  90                  95

Ser Gly Gln Gln Gly Pro Gly Ala Ser Ala Ala Ala Ala Gly Gln
```

```
                100             105             110
Tyr Gly Pro Gly Gln Gln Gly Pro Gly Gln Gly Pro Gly Ser Ser
            115             120             125
Ala Ala Ala Ala Ala Gly Gln Tyr Gly Ser Gly Pro Gly Gln Gln Gly
            130             135             140
Pro Tyr Gly Ser Ala Ala Ala Ala Gly Pro Gly Ser Gly Gln Tyr
145             150             155             160
Gly Gln Gly Pro Tyr Gly Pro Gly Ala Ser Ala Ala Ala Ala Gly
                165             170             175
Pro Gly Gln Tyr Gly Pro Gly Gln Gln Gly Pro Ser Ala Ser Ala Ala
                180             185             190
Ala Ala Ala Gly Ser Gly Gln Gln Gly Pro Gly Gln Tyr Gly Pro Tyr
            195             200             205
Ala Ser Ala Ala Ala Ala Gly Gln Tyr Gly Ser Gly Pro Gly Gln
            210             215             220
Gln Gly Pro Tyr Gly Pro Gly Gln Ser Ala Ala Ala Ala Gly Ser
225             230             235             240
Gly Gln Gln Gly Pro Gly Gln Gly Pro Tyr Ala Ser Ala Ala Ala
                245             250             255
Ala Ala Gly Pro Gly Gln Gln Gly Pro Tyr Gly Pro Gly Ser Ser Ala
            260             265             270
Ala Ala Ala Ala Gly Gln Tyr Gly Tyr Gly Pro Gly Gln Gln Gly Pro
            275             280             285
Tyr Gly Pro Gly Ala Ser Ala Ala Ala Ala Gly Gln Asn Gly Pro
            290             295             300
Gly Ser Gly Gln Tyr Gly Pro Gly Gln Gln Gly Pro Gly Gln Ser Ala
305             310             315             320
Ala Ala Ala Ala Gly Pro Gly Gln Gln Gly Pro Tyr Gly Pro Gly Ala
                325             330             335
Ser Ala Ala Ala Ala Gly Gln Tyr Gly Pro Gly Gln Gln Gly Pro
            340             345             350
Gly Gln Tyr Gly Pro Gly Ser Ser Ala Ala Ala Ala Gly Pro Gly
            355             360             365
Gln Gln Gly Pro Tyr Gly Pro Gly Ser Ser Ala Ala Ala Ala Gly
            370             375             380
Gln Tyr Gly Pro Gly Gln Gln Gly Pro Tyr Gly Pro Gly Gln Ser Ala
385             390             395             400
Ala Ala Ala Gly Gln Tyr Gln Gln Gly Pro Gly Gln Gln Gly Pro
                405             410             415
Tyr Gly Pro Gly Ala Ser Ala Ala Ala Ala Gly Pro Gly Gln Gln
                420             425             430
Gly Pro Tyr Gly Pro Gly Ala Ser Ala Ala Ala Ala Gly Pro Gly
            435             440             445
Gln Tyr Gly Pro Gly Gln Gln Gly Pro Ser Ala Ser Ala Ala Ala Ala
            450             455             460
Ala Gly Gln Tyr Gly Ser Gly Pro Gly Gln Tyr Gly Pro Tyr Gly Pro
465             470             475             480
Gly Gln Ser Ala Ala Ala Ala Gly Pro Gly Ser Gly Gln Gln Gly
                485             490             495
Gln Gly Pro Tyr Gly Pro Gly Ala Ser Ala Ala Ala Ala Gly Gln
            500             505             510
Tyr Gly Pro Gly Gln Gln Gly Pro Tyr Gly Pro Gly Gln Ser Ala Ala
            515             520             525
```

Ala Ala Ala Gly Pro Gly Ser Gly Gln Tyr Gly Pro Gly Ser Ala
            530                 535                 540

Ala Ala Ala Ala Gly Gln Asn Gly Pro Gly Ser Gly Gln Tyr Gly Pro
545                 550                 555                 560

Gly Gln Gln Gly Pro Gly Gln Ser Ala Ala Ala Ala Gly Gln Tyr
                565                 570                 575

Gln Gln Gly Pro Gly Gln Gly Pro Tyr Gly Pro Gly Ala Ser Ala
            580                 585                 590

Ala Ala Ala Ala Gly Pro Gly Ser Gly Gln Gln Gly Pro Gly Ala Ser
            595                 600                 605

<210> SEQ ID NO 9
<211> LENGTH: 601
<212> TYPE: PRT
<213> ORGANISM: Artificial Sequence
<220> FEATURE:
<223> OTHER INFORMATION: PRT410

<400> SEQUENCE: 9

Met His His His His His Ser Ser Gly Ser Ser Gly Pro Gly Gln
1               5                   10                  15

Gln Gly Pro Tyr Gly Pro Gly Ala Ser Ala Ala Ala Ala Gly Gln
            20                  25                  30

Asn Gly Pro Gly Ser Gly Gln Gln Gly Pro Gly Gln Ser Gly Gln Tyr
            35                  40                  45

Gly Pro Gly Gln Gln Gly Pro Gln Gln Gly Pro Gly Ser Ser Ala
        50                  55                  60

Ala Ala Ala Ala Gly Pro Gly Gln Tyr Gly Pro Gly Gln Gln Gly Pro
65                  70                  75                  80

Ser Ala Ser Ala Ala Ala Ala Ala Gly Pro Gly Ser Gly Gln Gln Gly
                85                  90                  95

Pro Gly Ala Ser Gly Gln Tyr Gly Pro Gly Gln Gln Gly Pro Gly Gln
                100                 105                 110

Gln Gly Pro Gly Ser Ser Ala Ala Ala Ala Gly Gln Tyr Gly Ser
            115                 120                 125

Gly Pro Gly Gln Gln Gly Pro Tyr Gly Ser Ala Ala Ala Ala Gly
        130                 135                 140

Pro Gly Ser Gly Gln Tyr Gly Gln Gly Pro Tyr Gly Pro Gly Ala Ser
145                 150                 155                 160

Gly Pro Gly Gln Tyr Gly Pro Gly Gln Gln Gly Pro Ser Ala Ser Ala
                165                 170                 175

Ala Ala Ala Gly Ser Gly Gln Gln Gly Pro Gly Gln Tyr Gly Pro
            180                 185                 190

Tyr Ala Ser Ala Ala Ala Ala Gly Gln Tyr Gly Ser Gly Pro Gly
            195                 200                 205

Gln Gln Gly Pro Tyr Gly Pro Gly Gln Ser Gly Ser Gly Gln Gln Gly
            210                 215                 220

Pro Gly Gln Gln Gly Pro Tyr Ala Ser Ala Ala Ala Ala Gly Pro
225                 230                 235                 240

Gly Gln Gln Gly Pro Tyr Gly Pro Gly Ser Ser Ala Ala Ala Ala
                245                 250                 255

Gly Gln Tyr Gly Tyr Gly Pro Gly Gln Gln Gly Pro Tyr Gly Pro Gly
            260                 265                 270

Ala Ser Gly Gln Asn Gly Pro Gly Ser Gly Gln Tyr Gly Pro Gly Gln
            275                 280                 285

-continued

```
Gln Gly Pro Gly Gln Ser Ala Ala Ala Ala Gly Pro Gly Gln Gln
        290                 295                 300

Gly Pro Tyr Gly Pro Gly Ala Ser Ala Ala Ala Ala Gly Gln Tyr
305                 310                 315                 320

Gly Pro Gly Gln Gln Gly Pro Gly Gln Tyr Gly Pro Gly Ser Ser Gly
                325                 330                 335

Pro Gly Gln Gln Gly Pro Tyr Gly Pro Gly Ser Ser Ala Ala Ala
                340                 345                 350

Ala Gly Gln Tyr Gly Pro Gly Gln Gln Gly Pro Tyr Gly Pro Gly Gln
        355                 360                 365

Ser Ala Ala Ala Ala Gly Gln Tyr Gln Gly Pro Gly Gln Gln
370                 375                 380

Gly Pro Tyr Gly Pro Gly Ala Ser Gly Pro Gly Gln Gln Gly Pro Tyr
385                 390                 395                 400

Gly Pro Gly Ala Ser Ala Ala Ala Ala Gly Pro Gly Gln Tyr Gly
                405                 410                 415

Pro Gly Gln Gln Gly Pro Ser Ala Ser Ala Ala Ala Ala Gly Gln
                420                 425                 430

Tyr Gly Ser Gly Pro Gly Gln Tyr Gly Pro Tyr Gly Pro Gly Gln Ser
        435                 440                 445

Gly Pro Gly Ser Gly Gln Gln Gly Gln Gly Pro Tyr Gly Pro Gly Ala
        450                 455                 460

Ser Ala Ala Ala Ala Gly Gln Tyr Gly Pro Gly Gln Gln Gly Pro
465                 470                 475                 480

Tyr Gly Pro Gly Gln Ser Ala Ala Ala Ala Gly Pro Gly Ser Gly
                485                 490                 495

Gln Tyr Gly Pro Gly Ala Ser Gly Gln Asn Gly Pro Gly Ser Gly Gln
        500                 505                 510

Tyr Gly Pro Gly Gln Gln Gly Pro Gln Ser Ala Ala Ala Ala
        515                 520                 525

Gly Gln Tyr Gln Gln Gly Pro Gly Gln Gln Gly Pro Tyr Gly Pro Gly
        530                 535                 540

Ala Ser Ala Ala Ala Ala Gly Gln Tyr Gly Ser Gly Pro Gly Gln
545                 550                 555                 560

Gln Gly Pro Tyr Gly Pro Gly Gln Ser Gly Ser Gly Gln Gln Gly Pro
                565                 570                 575

Gly Gln Gln Gly Pro Tyr Ala Ser Ala Ala Ala Ala Gly Pro Gly
                580                 585                 590

Ser Gly Gln Gln Gly Pro Gly Ala Ser
        595                 600
```

<210> SEQ ID NO 10
<211> LENGTH: 565
<212> TYPE: PRT
<213> ORGANISM: Artificial Sequence
<220> FEATURE:
<223> OTHER INFORMATION: Met-PRT468

<400> SEQUENCE: 10

```
Met Gly Pro Gly Gln Gln Gly Pro Tyr Gly Pro Gly Ala Ser Ala Ala
1               5                   10                  15

Ala Ala Ala Ala Gly Ser Asn Gly Pro Gly Ser Gly Gln Gln Gly
                20                  25                  30

Pro Gly Ser Gly Gln Tyr Gly Pro Gly Gln Gln Gly Pro Gly Gln
        35                  40                  45
```

-continued

Gln Gly Pro Gly Ser Ser Ala Ala Ala Ala Ala Gly Pro Gly
              50                  55                  60

Gln Tyr Gly Pro Gly Gln Gly Pro Ser Ala Ser Ala Ala Ala
 65                  70                  75                  80

Ala Ala Ala Gly Pro Gly Ser Gly Gln Gln Gly Pro Gly Ala Ser Gly
                 85                  90                  95

Gln Tyr Gly Pro Gly Gln Gln Gly Pro Gly Gln Gln Gly Pro Gly Ser
                100                 105                 110

Ser Ala Ala Ala Ala Ala Ala Gly Ser Tyr Gly Ser Gly Pro Gly
        115                 120                 125

Gln Gln Gly Pro Tyr Gly Ser Ala Ala Ala Ala Ala Gly Pro
    130                 135                 140

Gly Ser Gly Gln Tyr Gly Gln Gly Pro Tyr Gly Pro Gly Ala Ser Gly
145                 150                 155                 160

Pro Gly Gln Tyr Gly Pro Gly Gln Gln Gly Pro Ser Ala Ser Ala Ala
                165                 170                 175

Ala Ala Ala Ala Ala Gly Ser Gly Gln Gln Gly Pro Gly Gln Tyr Gly
        180                 185                 190

Pro Tyr Ala Ser Ala Ala Ala Ala Ala Ala Gly Ser Tyr Gly Ser
        195                 200                 205

Gly Pro Gly Gln Gln Gly Pro Tyr Gly Pro Gly Gln Ser Gly Ser Gly
    210                 215                 220

Gln Gln Gly Pro Gly Gln Gln Gly Pro Tyr Ala Ser Ala Ala Ala
225                 230                 235                 240

Ala Ala Ala Gly Pro Gly Gln Gln Gly Pro Tyr Gly Pro Gly Ser Ser
                245                 250                 255

Ala Ala Ala Ala Ala Ala Gly Ser Tyr Gly Tyr Gly Pro Gly Gln
        260                 265                 270

Gln Gly Pro Tyr Gly Pro Gly Ala Ser Gly Gln Asn Gly Pro Gly Ser
    275                 280                 285

Gly Gln Tyr Gly Pro Gly Gln Gln Gly Pro Gly Pro Ser Ala Ala Ala
    290                 295                 300

Ala Ala Ala Ala Gly Pro Gly Gln Gln Gly Pro Tyr Gly Pro Gly Ala
305                 310                 315                 320

Ser Ala Ala Ala Ala Ala Ala Gly Ser Tyr Gly Pro Gly Gln Gln
        325                 330                 335

Gly Pro Gly Gln Tyr Gly Pro Gly Ser Ser Gly Pro Gly Gln Gln Gly
    340                 345                 350

Pro Tyr Gly Pro Gly Ser Ser Ala Ala Ala Ala Ala Gly Ser
    355                 360                 365

Tyr Gly Pro Gly Gln Gln Gly Pro Tyr Gly Pro Gly Pro Ser Ala Ala
370                 375                 380

Ala Ala Ala Ala Ala Gly Ser Tyr Gln Gln Gly Pro Gly Gln Gln Gly
385                 390                 395                 400

Pro Tyr Gly Pro Gly Ala Ser Gly Pro Gly Gln Gln Gly Pro Tyr Gly
                405                 410                 415

Pro Gly Ala Ser Ala Ala Ala Ala Ala Ala Gly Pro Gly Gln Tyr
        420                 425                 430

Gly Pro Gly Gln Gln Gly Pro Ser Ala Ser Ala Ala Ala Ala Ala
        435                 440                 445

Ala Gly Ser Tyr Gly Ser Gly Pro Gly Gln Tyr Gly Pro Tyr Gly Pro
450                 455                 460

Gly Gln Ser Gly Pro Gly Ser Gly Gln Gln Gly Gly Pro Tyr Gly
465                 470                 475                 480

Pro Gly Ala Ser Ala Ala Ala Ala Ala Ala Gly Ser Tyr Gly Pro
            485                 490                 495

Gly Gln Gln Gly Pro Tyr Gly Pro Gly Ser Ala Ala Ala Ala
        500                 505                 510

Ala Ala Gly Pro Gly Ser Gly Gln Tyr Gly Pro Gly Ala Ser Gly Gln
        515                 520                 525

Asn Gly Pro Gly Ser Gly Gln Tyr Gly Pro Gly Gln Gln Gly Pro Gly
        530                 535                 540

Pro Ser Ala Ala Ala Ala Ala Ala Gly Pro Gly Ser Gly Gln Gln
545                 550                 555                 560

Gly Pro Gly Ala Ser
            565

<210> SEQ ID NO 11
<211> LENGTH: 576
<212> TYPE: PRT
<213> ORGANISM: Artificial Sequence
<220> FEATURE:
<223> OTHER INFORMATION: PRT468

<400> SEQUENCE: 11

Met His His His His His Ser Ser Gly Ser Ser Gly Pro Gly Gln
1               5                   10                  15

Gln Gly Pro Tyr Gly Pro Gly Ala Ser Ala Ala Ala Ala Ala Ala
                20                  25                  30

Gly Ser Asn Gly Pro Gly Ser Gln Gln Gly Pro Gln Ser Gly
        35                  40                  45

Gln Tyr Gly Pro Gly Gln Gln Gly Pro Gly Gln Gln Gly Pro Gly Ser
    50                  55                  60

Ser Ala Ala Ala Ala Ala Ala Gly Pro Gly Gln Tyr Gly Pro Gly
65                  70                  75                  80

Gln Gln Gly Pro Ser Ala Ser Ala Ala Ala Ala Ala Ala Gly Pro
            85                  90                  95

Gly Ser Gly Gln Gln Gly Pro Gly Ala Ser Gly Gln Tyr Gly Pro Gly
        100                 105                 110

Gln Gln Gly Pro Gly Gln Gln Gly Pro Gly Ser Ser Ala Ala Ala Ala
        115                 120                 125

Ala Ala Ala Gly Ser Tyr Gly Ser Gly Pro Gly Gln Gln Gly Pro Tyr
130                 135                 140

Gly Ser Ala Ala Ala Ala Ala Ala Gly Pro Gly Ser Gly Gln Tyr
145                 150                 155                 160

Gly Gln Gly Pro Tyr Gly Pro Gly Ala Ser Gly Pro Gly Gln Tyr Gly
            165                 170                 175

Pro Gly Gln Gln Gly Pro Ser Ala Ser Ala Ala Ala Ala Ala Ala
            180                 185                 190

Gly Ser Gly Gln Gln Gly Pro Gly Gln Tyr Gly Pro Tyr Ala Ser Ala
        195                 200                 205

Ala Ala Ala Ala Ala Gly Ser Tyr Gly Ser Gly Pro Gly Gln Gln
        210                 215                 220

Gly Pro Tyr Gly Pro Gly Gln Ser Gly Gln Gln Gly Pro Gly
225                 230                 235                 240

Gln Gln Gly Pro Tyr Ala Ser Ala Ala Ala Ala Ala Ala Gly Pro
            245                 250                 255

Gly Gln Gln Gly Pro Tyr Gly Pro Gly Ser Ala Ala Ala Ala
                260                 265                 270

Ala Ala Gly Ser Tyr Gly Tyr Gly Pro Gly Gln Gln Gly Pro Tyr Gly
            275                 280                 285

Pro Gly Ala Ser Gly Gln Asn Gly Pro Gly Ser Gly Gln Tyr Gly Pro
            290                 295                 300

Gly Gln Gln Gly Pro Gly Pro Ser Ala Ala Ala Ala Ala Ala Gly
305                 310                 315                 320

Pro Gly Gln Gln Gly Pro Tyr Gly Pro Gly Ala Ser Ala Ala Ala Ala
                325                 330                 335

Ala Ala Ala Gly Ser Tyr Gly Pro Gly Gln Gln Gly Pro Gly Gln Tyr
            340                 345                 350

Gly Pro Gly Ser Ser Gly Pro Gly Gln Gln Gly Pro Tyr Gly Pro Gly
            355                 360                 365

Ser Ser Ala Ala Ala Ala Ala Ala Gly Ser Tyr Gly Pro Gly Gln
            370                 375                 380

Gln Gly Pro Tyr Gly Pro Gly Pro Ser Ala Ala Ala Ala Ala Ala
385                 390                 395                 400

Gly Ser Tyr Gln Gln Gly Pro Gly Gln Gln Gly Pro Tyr Gly Pro Gly
            405                 410                 415

Ala Ser Gly Pro Gly Gln Gln Gly Pro Tyr Gly Pro Gly Ala Ser Ala
            420                 425                 430

Ala Ala Ala Ala Ala Ala Gly Pro Gly Gln Tyr Gly Pro Gly Gln Gln
            435                 440                 445

Gly Pro Ser Ala Ser Ala Ala Ala Ala Ala Gly Ser Tyr Gly
            450                 455                 460

Ser Gly Pro Gly Gln Tyr Gly Pro Tyr Gly Pro Gly Gln Ser Gly Pro
465                 470                 475                 480

Gly Ser Gly Gln Gln Gly Gly Pro Tyr Gly Pro Gly Ala Ser Ala
            485                 490                 495

Ala Ala Ala Ala Ala Gly Ser Tyr Gly Pro Gly Gln Gln Gly Pro
            500                 505                 510

Tyr Gly Pro Gly Pro Ser Ala Ala Ala Ala Ala Ala Gly Pro Gly
            515                 520                 525

Ser Gly Gln Tyr Gly Pro Gly Ala Ser Gly Gln Asn Gly Pro Gly Ser
            530                 535                 540

Gly Gln Tyr Gly Pro Gly Gln Gln Gly Pro Gly Pro Ser Ala Ala Ala
545                 550                 555                 560

Ala Ala Ala Ala Gly Pro Gly Ser Gly Gln Gln Gly Pro Gly Ala Ser
            565                 570                 575

<210> SEQ ID NO 12
<211> LENGTH: 2364
<212> TYPE: PRT
<213> ORGANISM: Artificial Sequence
<220> FEATURE:
<223> OTHER INFORMATION: Met-PRT799

<400> SEQUENCE: 12

Met Gly Pro Gly Gln Gln Gly Pro Tyr Gly Pro Gly Ala Ser Ala Ala
1               5                   10                  15

Ala Ala Ala Gly Gln Asn Gly Pro Gly Ser Gly Gln Gln Gly Pro Gly
            20                  25                  30

Gln Ser Gly Gln Tyr Gly Pro Gly Gln Gln Gly Pro Gly Gln Gln Gly
            35                  40                  45

```
Pro Gly Ser Ser Ala Ala Ala Ala Gly Pro Gln Tyr Gly Pro
    50              55              60

Gly Gln Gln Gly Pro Ser Ala Ser Ala Ala Ala Ala Gly Pro Gly
65              70              75              80

Ser Gly Gln Gln Gly Pro Gly Ala Ser Gly Gln Tyr Gly Pro Gly Gln
                85              90              95

Gln Gly Pro Gly Gln Gln Gly Pro Gly Ser Ser Ala Ala Ala Ala
            100             105             110

Gly Gln Tyr Gly Ser Gly Pro Gly Gln Gln Gly Pro Tyr Gly Ser Ala
        115             120             125

Ala Ala Ala Ala Gly Pro Gly Ser Gly Gln Tyr Gly Gln Gly Pro Tyr
130             135             140

Gly Pro Gly Ala Ser Gly Pro Gly Gln Tyr Gly Pro Gly Gln Gln Gly
145             150             155             160

Pro Ser Ala Ser Ala Ala Ala Ala Gly Ser Gly Gln Gln Gly Pro
            165             170             175

Gly Gln Tyr Gly Pro Tyr Ala Ser Ala Ala Ala Ala Gly Gln Tyr
        180             185             190

Gly Ser Gly Pro Gly Gln Gln Gly Pro Tyr Gly Pro Gly Ser Gly
        195             200             205

Ser Gly Gln Gln Gly Pro Gly Gln Gln Gly Pro Tyr Ala Ser Ala Ala
210             215             220

Ala Ala Ala Gly Pro Gly Gln Gln Gly Pro Tyr Gly Pro Gly Ser Ser
225             230             235             240

Ala Ala Ala Ala Ala Gly Gln Tyr Gly Tyr Gly Pro Gly Gln Gln Gly
                245             250             255

Pro Tyr Gly Pro Gly Ala Ser Gly Gln Asn Gly Pro Gly Ser Gly Gln
        260             265             270

Tyr Gly Pro Gly Gln Gln Gly Pro Gly Gln Ser Ala Ala Ala Ala
        275             280             285

Gly Pro Gly Gln Gln Gly Pro Tyr Gly Pro Gly Ala Ser Ala Ala Ala
290             295             300

Ala Ala Gly Gln Tyr Gly Pro Gly Gln Gln Gly Pro Gly Gln Tyr Gly
305             310             315             320

Pro Gly Ser Ser Gly Pro Gly Gln Gln Gly Pro Tyr Gly Pro Gly Ser
            325             330             335

Ser Ala Ala Ala Ala Gly Gln Tyr Gly Pro Gly Gln Gln Gly Pro
            340             345             350

Tyr Gly Pro Gly Gln Ser Ala Ala Ala Ala Gly Gln Tyr Gln Gln
        355             360             365

Gly Pro Gly Gln Gln Gly Pro Tyr Gly Pro Gly Ala Ser Gly Pro Gly
370             375             380

Gln Gln Gly Pro Tyr Gly Pro Gly Ala Ser Ala Ala Ala Ala Gly
385             390             395             400

Pro Gly Gln Tyr Gly Pro Gly Gln Gly Pro Ser Ala Ser Ala Ala
        405             410             415

Ala Ala Ala Gly Gln Tyr Gly Ser Gly Pro Gly Gln Tyr Gly Pro Tyr
        420             425             430

Gly Pro Gly Gln Ser Gly Pro Ser Gly Gln Gln Gln Gly Pro
        435             440             445

Tyr Gly Pro Gly Ala Ser Ala Ala Ala Ala Gly Gln Tyr Gly Pro
        450             455             460

Gly Gln Gln Gly Pro Tyr Gly Pro Gly Gln Ser Ala Ala Ala Ala Ala
```

-continued

```
            465                 470                 475                 480
Gly Pro Gly Ser Gly Gln Tyr Gly Pro Gly Ala Ser Gly Gln Asn Gly
                    485                 490                 495
Pro Gly Ser Gly Gln Tyr Gly Pro Gln Gln Gly Pro Gly Gln Ser
                500                 505                 510
Ala Ala Ala Ala Ala Gly Gln Gly Gln Gly Pro Gly Gln Gln Gly
            515                 520                 525
Pro Tyr Gly Pro Gly Ala Ser Ala Ala Ala Ala Gly Gln Tyr Gly
        530                 535                 540
Ser Gly Pro Gly Gln Gln Gly Pro Tyr Gly Pro Gly Gln Ser Gly Ser
545                 550                 555                 560
Gly Gln Gln Gly Pro Gly Gln Gly Pro Tyr Ala Ser Ala Ala Ala
                565                 570                 575
Ala Ala Gly Pro Gly Ser Gly Gln Gly Pro Gly Ala Ser Gly Gln
            580                 585                 590
Gln Gly Pro Tyr Gly Pro Gly Ala Ser Ala Ala Ala Ala Gly Gln
        595                 600                 605
Asn Gly Pro Gly Ser Gly Gln Gln Gly Pro Gly Gln Ser Gly Gln Tyr
    610                 615                 620
Gly Pro Gly Gln Gln Gly Pro Gly Gln Gln Gly Pro Gly Ser Ser Ala
625                 630                 635                 640
Ala Ala Ala Ala Gly Pro Gly Gln Tyr Gly Pro Gly Gln Gln Gly Pro
                645                 650                 655
Ser Ala Ser Ala Ala Ala Ala Gly Pro Gly Ser Gly Gln Gln Gly
            660                 665                 670
Pro Gly Ala Ser Gly Gln Tyr Gly Pro Gly Gln Gln Gly Pro Gly Gln
        675                 680                 685
Gln Gly Pro Gly Ser Ser Ala Ala Ala Ala Gly Tyr Gly Ser
    690                 695                 700
Gly Pro Gly Gln Gln Gly Pro Tyr Gly Ser Ala Ala Ala Ala Gly
705                 710                 715                 720
Pro Gly Ser Gly Gln Tyr Gly Gln Gly Pro Tyr Gly Pro Gly Ala Ser
                725                 730                 735
Gly Pro Gly Gln Tyr Gly Pro Gly Gln Gln Gly Pro Ser Ala Ser Ala
                740                 745                 750
Ala Ala Ala Gly Ser Gly Gln Gln Gly Pro Gly Gln Tyr Gly Pro
        755                 760                 765
Tyr Ala Ser Ala Ala Ala Ala Gly Gln Tyr Gly Ser Gly Pro Gly
    770                 775                 780
Gln Gln Gly Pro Tyr Gly Pro Gly Ser Gly Ser Gly Gln Gln Gly
785                 790                 795                 800
Pro Gly Gln Gln Gly Pro Tyr Ala Ser Ala Ala Ala Ala Gly Pro
                805                 810                 815
Gly Gln Gln Gly Pro Tyr Gly Pro Gly Ser Ser Ala Ala Ala Ala
            820                 825                 830
Gly Gln Tyr Gly Tyr Gly Pro Gly Gln Gln Gly Pro Tyr Gly Pro Gly
        835                 840                 845
Ala Ser Gly Gln Asn Gly Pro Gly Ser Gly Gln Tyr Gly Pro Gly Gln
    850                 855                 860
Gln Gly Pro Gly Gln Ser Ala Ala Ala Ala Gly Pro Gly Gln Gln
865                 870                 875                 880
Gly Pro Tyr Gly Pro Gly Ala Ser Ala Ala Ala Ala Gly Gln Tyr
                885                 890                 895
```

-continued

Gly Pro Gly Gln Gln Gly Pro Gly Gln Tyr Gly Pro Gly Ser Ser Gly
                900                 905                 910

Pro Gly Gln Gln Gly Pro Tyr Gly Pro Gly Ser Ser Ala Ala Ala
            915                 920                 925

Ala Gly Gln Tyr Gly Pro Gly Gln Gln Gly Pro Tyr Gly Pro Gly Gln
930                 935                 940

Ser Ala Ala Ala Ala Gly Gln Tyr Gln Gln Gly Pro Gly Gln Gln
945                 950                 955                 960

Gly Pro Tyr Gly Pro Gly Ala Ser Gly Pro Gly Gln Gln Pro Tyr
            965                 970                 975

Gly Pro Gly Ala Ser Ala Ala Ala Ala Gly Pro Gly Gln Tyr Gly
                980                 985                 990

Pro Gly Gln Gln Gly Pro Ser Ala Ser Ala Ala Ala Ala Gly Gln
            995                 1000                1005

Tyr Gly Ser Gly Pro Gly Gln Tyr Gly Pro Tyr Gly Pro Gly Gln
1010                1015                1020

Ser Gly Pro Gly Ser Gly Gln Gln Gly Gln Gly Pro Tyr Gly Pro
1025                1030                1035

Gly Ala Ser Ala Ala Ala Ala Gly Gln Tyr Gly Pro Gly Gln
1040                1045                1050

Gln Gly Pro Tyr Gly Pro Gly Gln Ser Ala Ala Ala Ala Ala Gly
1055                1060                1065

Pro Gly Ser Gly Gln Tyr Gly Pro Gly Ala Ser Gly Gln Asn Gly
1070                1075                1080

Pro Gly Ser Gly Gln Tyr Gly Pro Gly Gln Gly Pro Gly Gln
1085                1090                1095

Ser Ala Ala Ala Ala Gly Gln Tyr Gln Gln Gly Pro Gly Gln
1100                1105                1110

Gln Gly Pro Tyr Gly Pro Gly Ala Ser Ala Ala Ala Ala Ala Gly
1115                1120                1125

Gln Tyr Gly Ser Gly Pro Gly Gln Gln Gly Pro Tyr Gly Pro Gly
1130                1135                1140

Gln Ser Gly Ser Gly Gln Gln Gly Pro Gly Gln Gln Gly Pro Tyr
1145                1150                1155

Ala Ser Ala Ala Ala Ala Gly Pro Gly Ser Gly Gln Gln Gly
1160                1165                1170

Pro Gly Ala Ser Gly Gln Gln Gly Pro Tyr Gly Pro Gly Ala Ser
1175                1180                1185

Ala Ala Ala Ala Gly Gln Asn Gly Pro Gly Ser Gly Gln Gln
1190                1195                1200

Gly Pro Gly Gln Ser Gly Gln Tyr Gly Pro Gly Gln Gln Gly Pro
1205                1210                1215

Gly Gln Gln Gly Pro Gly Ser Ser Ala Ala Ala Ala Gly Pro
1220                1225                1230

Gly Gln Tyr Gly Pro Gly Gln Gln Gly Pro Ser Ala Ser Ala Ala
1235                1240                1245

Ala Ala Ala Gly Pro Gly Ser Gly Gln Gln Gly Pro Gly Ala Ser
1250                1255                1260

Gly Gln Tyr Gly Pro Gly Gln Gln Gly Pro Gly Gln Gln Gly Pro
1265                1270                1275

Gly Ser Ser Ala Ala Ala Ala Gly Gln Tyr Gly Ser Gly Pro
1280                1285                1290

```
Gly Gln Gln Gly Pro Tyr Gly Ser Ala Ala Ala Ala Gly Pro
    1295                1300                1305

Gly Ser Gly Gln Tyr Gly Gln Gly Pro Tyr Gly Pro Gly Ala Ser
    1310                1315                1320

Gly Pro Gly Gln Tyr Gly Pro Gly Gln Gln Gly Pro Ser Ala Ser
    1325                1330                1335

Ala Ala Ala Ala Ala Gly Ser Gly Gln Gln Gly Pro Gly Gln Tyr
    1340                1345                1350

Gly Pro Tyr Ala Ser Ala Ala Ala Ala Gly Gln Tyr Gly Ser
    1355                1360                1365

Gly Pro Gly Gln Gln Gly Pro Tyr Gly Pro Gly Gln Ser Gly Ser
    1370                1375                1380

Gly Gln Gln Gly Pro Gly Gln Gln Gly Pro Tyr Ala Ser Ala Ala
    1385                1390                1395

Ala Ala Ala Gly Pro Gly Gln Gln Gly Pro Tyr Gly Pro Gly Ser
    1400                1405                1410

Ser Ala Ala Ala Ala Gly Gln Tyr Gly Tyr Gly Pro Gly Gln
    1415                1420                1425

Gln Gly Pro Tyr Gly Pro Gly Ala Ser Gly Gln Asn Gly Pro Gly
    1430                1435                1440

Ser Gly Gln Tyr Gly Pro Gly Gln Gln Gly Pro Gly Gln Ser Ala
    1445                1450                1455

Ala Ala Ala Gly Pro Gly Gln Gln Gly Pro Tyr Gly Pro Gly
    1460                1465                1470

Ala Ser Ala Ala Ala Ala Ala Gly Gln Tyr Gly Pro Gly Gln Gln
    1475                1480                1485

Gly Pro Gly Gln Tyr Gly Pro Gly Ser Ser Gly Pro Gly Gln Gln
    1490                1495                1500

Gly Pro Tyr Gly Pro Gly Ser Ser Ala Ala Ala Ala Gly Gln
    1505                1510                1515

Tyr Gly Pro Gly Gln Gln Gly Pro Tyr Gly Pro Gly Gln Ser Ala
    1520                1525                1530

Ala Ala Ala Gly Gln Tyr Gln Gln Gly Pro Gly Gln Gln Gly
    1535                1540                1545

Pro Tyr Gly Pro Gly Ala Ser Gly Pro Gly Gln Gln Gly Pro Tyr
    1550                1555                1560

Gly Pro Gly Ala Ser Ala Ala Ala Ala Gly Pro Gly Gln Tyr
    1565                1570                1575

Gly Pro Gly Gln Gln Gly Pro Ser Ala Ser Ala Ala Ala Ala Ala
    1580                1585                1590

Gly Gln Tyr Gly Ser Gly Pro Gly Gln Tyr Gly Tyr Gly Pro
    1595                1600                1605

Gly Gln Ser Gly Pro Gly Ser Gly Gln Gln Gly Gln Gly Pro Tyr
    1610                1615                1620

Gly Pro Gly Ala Ser Ala Ala Ala Ala Gly Gln Tyr Gly Pro
    1625                1630                1635

Gly Gln Gln Gly Pro Tyr Gly Pro Gly Gln Ser Ala Ala Ala Ala
    1640                1645                1650

Ala Gly Pro Gly Ser Gly Gln Tyr Gly Pro Gly Ala Ser Gly Gln
    1655                1660                1665

Asn Gly Pro Gly Ser Gly Gln Tyr Gly Pro Gly Gln Gln Gly Pro
    1670                1675                1680

Gly Gln Ser Ala Ala Ala Ala Ala Gly Gln Tyr Gln Gln Gly Pro
```

-continued

```
            1685                1690                1695

Gly Gln Gln Gly Pro Tyr Gly Pro Gly Ala Ser Ala Ala Ala Ala
            1700                1705                1710

Ala Gly Gln Tyr Gly Ser Gly Pro Gly Gln Gln Gly Pro Tyr Gly
            1715                1720                1725

Pro Gly Gln Ser Gly Ser Gly Gln Gln Gly Pro Gly Gln Gln Gly
            1730                1735                1740

Pro Tyr Ala Ser Ala Ala Ala Ala Gly Pro Gly Ser Gly Gln
            1745                1750                1755

Gln Gly Pro Gly Ala Ser Gly Gln Gln Gly Pro Tyr Gly Pro Gly
            1760                1765                1770

Ala Ser Ala Ala Ala Ala Gly Gln Asn Gly Pro Gly Ser Gly
            1775                1780                1785

Gln Gln Gly Pro Gly Gln Ser Gly Gln Tyr Gly Pro Gly Gln Gln
            1790                1795                1800

Gly Pro Gly Gln Gln Gly Pro Gly Ser Ser Ala Ala Ala Ala Ala
            1805                1810                1815

Gly Pro Gly Gln Tyr Gly Pro Gly Gln Gln Gly Pro Ser Ala Ser
            1820                1825                1830

Ala Ala Ala Ala Ala Gly Pro Gly Ser Gly Gln Gln Gly Pro Gly
            1835                1840                1845

Ala Ser Gly Gln Tyr Gly Pro Gly Gln Gln Gly Pro Gly Gln Gln
            1850                1855                1860

Gly Pro Gly Ser Ser Ala Ala Ala Ala Ala Gly Gln Tyr Gly Ser
            1865                1870                1875

Gly Pro Gly Gln Gln Gly Pro Tyr Gly Ser Ala Ala Ala Ala Ala
            1880                1885                1890

Gly Pro Gly Ser Gly Gln Tyr Gly Gln Gly Pro Tyr Gly Pro Gly
            1895                1900                1905

Ala Ser Gly Pro Gly Gln Tyr Gly Pro Gly Gln Gln Gly Pro Ser
            1910                1915                1920

Ala Ser Ala Ala Ala Ala Ala Gly Ser Gly Gln Gln Gly Pro Gly
            1925                1930                1935

Gln Tyr Gly Pro Tyr Ala Ser Ala Ala Ala Ala Gly Gln Tyr
            1940                1945                1950

Gly Ser Gly Pro Gly Gln Gln Gly Pro Tyr Gly Pro Gly Gln Ser
            1955                1960                1965

Gly Ser Gly Gln Gln Gly Pro Gly Gln Gln Gly Pro Tyr Ala Ser
            1970                1975                1980

Ala Ala Ala Ala Ala Gly Pro Gly Gln Gln Gly Pro Tyr Gly Pro
            1985                1990                1995

Gly Ser Ser Ala Ala Ala Ala Ala Gly Gln Tyr Gly Tyr Gly Pro
            2000                2005                2010

Gly Gln Gln Gly Pro Tyr Gly Pro Gly Ala Ser Gly Gln Asn Gly
            2015                2020                2025

Pro Gly Ser Gly Gln Tyr Gly Pro Gly Gln Gln Gly Pro Gly Gln
            2030                2035                2040

Ser Ala Ala Ala Ala Ala Gly Pro Gly Gln Gln Gly Pro Tyr Gly
            2045                2050                2055

Pro Gly Ala Ser Ala Ala Ala Ala Gly Gln Tyr Gly Pro Gly
            2060                2065                2070

Gln Gln Gly Pro Gly Gln Tyr Gly Pro Gly Ser Ser Gly Pro Gly
            2075                2080                2085
```

```
Gln Gln Gly Pro Tyr Gly Pro Gly Ser Ser Ala Ala  Ala Ala Ala
    2090            2095                2100

Gly Gln Tyr Gly Pro Gly Gln Gln Gly Pro Tyr Gly  Pro Gly Gln
    2105            2110                2115

Ser Ala Ala Ala Ala Ala Gly Gln Tyr Gln Gln Gly  Pro Gly Gln
    2120            2125                2130

Gln Gly Pro Tyr Gly Pro Gly Ala Ser Gly Pro Gly  Gln Gln Gly
    2135            2140                2145

Pro Tyr Gly Pro Gly Ala Ser Ala Ala Ala Ala Gly  Pro Gly
    2150            2155                2160

Gln Tyr Gly Pro Gly Gln Gln Gly Pro Ser Ala Ser  Ala Ala Ala
    2165            2170                2175

Ala Ala Gly Gln Tyr Gly Ser Gly Pro Gly Gln Tyr  Gly Pro Tyr
    2180            2185                2190

Gly Pro Gly Gln Ser Gly Pro Gly Ser Gly Gln Gln  Gly Gln Gly
    2195            2200                2205

Pro Tyr Gly Pro Gly Ala Ser Ala Ala Ala Ala Gly  Gln Tyr
    2210            2215                2220

Gly Pro Gly Gln Gln Gly Pro Tyr Gly Pro Gly Gln  Ser Ala Ala
    2225            2230                2235

Ala Ala Ala Gly Pro Gly Ser Gly Gln Tyr Gly Pro  Gly Ala Ser
    2240            2245                2250

Gly Gln Asn Gly Pro Gly Ser Gly Gln Tyr Gly Pro  Gly Gln Gln
    2255            2260                2265

Gly Pro Gly Gln Ser Ala Ala Ala Ala Ala Gly Gln  Tyr Gln Gln
    2270            2275                2280

Gly Pro Gly Gln Gln Gly Pro Tyr Gly Pro Gly Ala  Ser Ala Ala
    2285            2290                2295

Ala Ala Ala Gly Gln Tyr Gly Ser Gly Pro Gly Gln  Gln Gly Pro
    2300            2305                2310

Tyr Gly Pro Gly Gln Ser Gly Ser Gly Gln Gln Gly  Pro Gly Gln
    2315            2320                2325

Gln Gly Pro Tyr Ala Ser Ala Ala Ala Ala Ala Gly  Pro Gly Ser
    2330            2335                2340

Gly Gln Gln Gly Ser Ser Val Asp Lys Leu Ala Ala  Ala Leu Glu
    2345            2350                2355

His His His His His His
    2360

<210> SEQ ID NO 13
<211> LENGTH: 2375
<212> TYPE: PRT
<213> ORGANISM: Artificial Sequence
<220> FEATURE:
<223> OTHER INFORMATION: PRT799

<400> SEQUENCE: 13

Met His His His His His His Ser Ser Gly Ser Ser Gly Pro Gly Gln
1               5                   10                  15

Gln Gly Pro Tyr Gly Pro Gly Ala Ser Ala Ala Ala Ala Gly Gln
            20                  25                  30

Asn Gly Pro Gly Ser Gly Gln Gln Gly Pro Gly Gln Ser Gly Gln Tyr
        35                  40                  45

Gly Pro Gly Gln Gln Gly Pro Gly Gln Gln Gly Pro Gly Ser Ser Ala
    50                  55                  60
```

Ala Ala Ala Ala Gly Pro Gly Gln Tyr Gly Pro Gln Gln Gly Pro
65                  70                  75                  80

Ser Ala Ser Ala Ala Ala Ala Gly Pro Gly Ser Gly Gln Gln Gly
                85                  90                  95

Pro Gly Ala Ser Gly Gln Tyr Gly Pro Gly Gln Gln Gly Pro Gly Gln
            100                 105                 110

Gln Gly Pro Gly Ser Ser Ala Ala Ala Ala Gly Gln Tyr Gly Ser
        115                 120                 125

Gly Pro Gly Gln Gln Gly Pro Tyr Gly Ser Ala Ala Ala Ala Gly
    130                 135                 140

Pro Gly Ser Gly Gln Tyr Gly Gln Gly Pro Tyr Gly Pro Gly Ala Ser
145                 150                 155                 160

Gly Pro Gly Gln Tyr Gly Pro Gly Gln Gln Gly Pro Ser Ala Ser Ala
                165                 170                 175

Ala Ala Ala Ala Gly Ser Gly Gln Gln Gly Pro Gly Gln Tyr Gly Pro
                180                 185                 190

Tyr Ala Ser Ala Ala Ala Ala Gly Gln Tyr Gly Ser Gly Pro Gly
        195                 200                 205

Gln Gln Gly Pro Tyr Gly Pro Gly Gln Ser Gly Ser Gly Gln Gln Gly
    210                 215                 220

Pro Gly Gln Gln Gly Pro Tyr Ala Ser Ala Ala Ala Ala Gly Pro
225                 230                 235                 240

Gly Gln Gln Gly Pro Tyr Gly Pro Gly Ser Ser Ala Ala Ala Ala
            245                 250                 255

Gly Gln Tyr Gly Tyr Gly Pro Gly Gln Gly Pro Tyr Gly Pro Gly
            260                 265                 270

Ala Ser Gly Gln Asn Gly Pro Gly Ser Gly Gln Tyr Gly Pro Gly Gln
        275                 280                 285

Gln Gly Pro Gly Gln Ser Ala Ala Ala Ala Gly Pro Gly Gln Gln
    290                 295                 300

Gly Pro Tyr Gly Pro Gly Ala Ser Ala Ala Ala Ala Gly Gln Tyr
305                 310                 315                 320

Gly Pro Gly Gln Gln Gly Pro Gly Gln Tyr Gly Pro Gly Ser Ser Gly
            325                 330                 335

Pro Gly Gln Gln Gly Pro Tyr Gly Pro Gly Ser Ser Ala Ala Ala Ala
        340                 345                 350

Ala Gly Gln Tyr Gly Pro Gly Gln Gly Pro Tyr Gly Pro Gly Gln
        355                 360                 365

Ser Ala Ala Ala Ala Gly Gln Tyr Gln Gln Gly Pro Gly Gln Gln
370                 375                 380

Gly Pro Tyr Gly Pro Gly Ala Ser Gly Pro Gly Gln Gln Gly Pro Tyr
385                 390                 395                 400

Gly Pro Gly Ala Ser Ala Ala Ala Ala Gly Pro Gly Gln Tyr Gly
            405                 410                 415

Pro Gly Gln Gln Gly Pro Ser Ala Ser Ala Ala Ala Ala Gly Gln
        420                 425                 430

Tyr Gly Ser Gly Pro Gly Gln Tyr Gly Pro Tyr Gly Pro Gly Gln Ser
        435                 440                 445

Gly Pro Gly Ser Gly Gln Gln Gly Gln Gly Pro Tyr Gly Pro Gly Ala
    450                 455                 460

Ser Ala Ala Ala Ala Ala Gly Gln Tyr Gly Pro Gly Gln Gln Gly Pro
465                 470                 475                 480

-continued

Tyr Gly Pro Gly Gln Ser Ala Ala Ala Ala Gly Pro Gly Ser Gly
                485                 490                 495

Gln Tyr Gly Pro Gly Ala Ser Gly Gln Asn Gly Pro Gly Ser Gly Gln
                500                 505                 510

Tyr Gly Pro Gly Gln Gln Gly Pro Gly Gln Ser Ala Ala Ala Ala
                515                 520                 525

Gly Gln Tyr Gln Gln Gly Pro Gly Gln Gln Gly Pro Tyr Gly Pro Gly
                530                 535                 540

Ala Ser Ala Ala Ala Ala Gly Gln Tyr Gly Ser Gly Pro Gly Gln
545                 550                 555                 560

Gln Gly Pro Tyr Gly Pro Gly Gln Ser Gly Ser Gly Gln Gln Gly Pro
                565                 570                 575

Gly Gln Gln Gly Pro Tyr Ala Ser Ala Ala Ala Ala Gly Pro Gly
                580                 585                 590

Ser Gly Gln Gln Gly Pro Gly Ala Ser Gly Gln Gln Gly Pro Tyr Gly
                595                 600                 605

Pro Gly Ala Ser Ala Ala Ala Ala Gly Gln Asn Gly Pro Gly Ser
                610                 615                 620

Gly Gln Gln Gly Pro Gly Gln Ser Gly Gln Tyr Gly Pro Gly Gln Gln
625                 630                 635                 640

Gly Pro Gly Gln Gln Gly Pro Gly Ser Ser Ala Ala Ala Ala Gly
                645                 650                 655

Pro Gly Gln Tyr Gly Pro Gly Gln Gln Gly Pro Ser Ala Ser Ala Ala
                660                 665                 670

Ala Ala Ala Gly Pro Gly Ser Gly Gln Gln Gly Pro Gly Ala Ser Gly
                675                 680                 685

Gln Tyr Gly Pro Gly Gln Gln Gly Pro Gly Gln Gln Gly Pro Gly Ser
                690                 695                 700

Ser Ala Ala Ala Ala Gly Gln Tyr Gly Ser Gly Pro Gly Gln Gln
705                 710                 715                 720

Gly Pro Tyr Gly Ser Ala Ala Ala Ala Gly Pro Gly Ser Gly Gln
                725                 730                 735

Tyr Gly Gln Gly Pro Tyr Gly Pro Gly Ala Ser Gly Pro Gly Gln Tyr
                740                 745                 750

Gly Pro Gly Gln Gln Gly Pro Ser Ala Ser Ala Ala Ala Ala Gly
                755                 760                 765

Ser Gly Gln Gln Gly Pro Gly Gln Tyr Gly Pro Tyr Ala Ser Ala Ala
                770                 775                 780

Ala Ala Ala Gly Gln Tyr Gly Ser Gly Pro Gly Gln Gln Gly Pro Tyr
785                 790                 795                 800

Gly Pro Gly Gln Ser Gly Ser Gly Gln Gln Gly Pro Gly Gln Gln Gly
                805                 810                 815

Pro Tyr Ala Ser Ala Ala Ala Ala Gly Pro Gly Gln Gln Gly Pro
                820                 825                 830

Tyr Gly Pro Gly Ser Ser Ala Ala Ala Ala Gly Gln Tyr Gly Tyr
                835                 840                 845

Gly Pro Gly Gln Gln Gly Pro Tyr Gly Pro Gly Ala Ser Gly Gln Asn
                850                 855                 860

Gly Pro Gly Ser Gly Gln Tyr Gly Pro Gly Gln Pro Gly Gln
865                 870                 875                 880

Ser Ala Ala Ala Ala Ala Gly Pro Gly Gln Gln Gly Pro Tyr Gly Pro
                885                 890                 895

Gly Ala Ser Ala Ala Ala Ala Ala Gly Gln Tyr Gly Pro Gly Gln Gln

```
                        900             905             910
Gly Pro Gly Gln Tyr Gly Pro Gly Ser Ser Gly Pro Gly Gln Gln Gly
            915             920             925

Pro Tyr Gly Pro Gly Ser Ser Ala Ala Ala Ala Gly Gln Tyr Gly
            930             935             940

Pro Gly Gln Gln Gly Pro Tyr Gly Pro Gly Gln Ser Ala Ala Ala
945             950             955             960

Ala Gly Gln Tyr Gln Gln Gly Pro Gly Gln Gly Pro Tyr Gly Pro
            965             970             975

Gly Ala Ser Gly Pro Gly Gln Gln Gly Pro Tyr Gly Pro Gly Ala Ser
            980             985             990

Ala Ala Ala Ala Ala Gly Pro Gly Gln Tyr Gly Pro Gly Gln Gln Gly
            995             1000            1005

Pro Ser Ala Ser Ala Ala Ala Ala Gly Gln Tyr Gly Ser Gly
    1010            1015            1020

Pro Gly Gln Tyr Gly Pro Tyr Gly Pro Gly Gln Ser Gly Pro Gly
    1025            1030            1035

Ser Gly Gln Gln Gly Gln Gly Pro Tyr Gly Pro Gly Ala Ser Ala
    1040            1045            1050

Ala Ala Ala Ala Gly Gln Tyr Gly Pro Gly Gln Gln Gly Pro Tyr
    1055            1060            1065

Gly Pro Gly Gln Ser Ala Ala Ala Ala Gly Pro Gly Ser Gly
    1070            1075            1080

Gln Tyr Gly Pro Gly Ala Ser Gly Gln Asn Gly Pro Gly Ser Gly
    1085            1090            1095

Gln Tyr Gly Pro Gly Gln Gln Gly Pro Gly Gln Ser Ala Ala Ala
    1100            1105            1110

Ala Ala Gly Gln Tyr Gln Gln Gly Pro Gly Gln Gln Gly Pro Tyr
    1115            1120            1125

Gly Pro Gly Ala Ser Ala Ala Ala Ala Ala Gly Gln Tyr Gly Ser
    1130            1135            1140

Gly Pro Gly Gln Gln Gly Pro Tyr Gly Pro Gly Gln Ser Gly Ser
    1145            1150            1155

Gly Gln Gln Gly Pro Gly Gln Gln Gly Pro Tyr Ala Ser Ala Ala
    1160            1165            1170

Ala Ala Ala Gly Pro Gly Ser Gly Gln Gln Gly Pro Gly Ala Ser
    1175            1180            1185

Gly Gln Gln Gly Pro Tyr Gly Pro Gly Ala Ser Ala Ala Ala Ala
    1190            1195            1200

Ala Gly Gln Asn Gly Pro Gly Ser Gly Gln Gln Gly Pro Gly Gln
    1205            1210            1215

Ser Gly Gln Tyr Gly Pro Gly Gln Gln Gly Pro Gly Gln Gln Gly
    1220            1225            1230

Pro Gly Ser Ser Ala Ala Ala Ala Ala Gly Pro Gly Gln Tyr Gly
    1235            1240            1245

Pro Gly Gln Gln Gly Pro Ser Ala Ser Ala Ala Ala Ala Gly
    1250            1255            1260

Pro Gly Ser Gly Gln Gln Gly Pro Gly Ala Ser Gly Gln Tyr Gly
    1265            1270            1275

Pro Gly Gln Gln Gly Pro Gly Gln Gln Gly Pro Gly Ser Ser Ala
    1280            1285            1290

Ala Ala Ala Ala Gly Gln Tyr Gly Ser Gly Pro Gly Gln Gln Gly
    1295            1300            1305
```

```
Pro Tyr Gly Ser Ala Ala Ala Ala Gly Pro Gly Ser Gly Gln
    1310            1315            1320

Tyr Gly Gln Gly Pro Tyr Gly Pro Gly Ala Ser Gly Pro Gly Gln
    1325            1330            1335

Tyr Gly Pro Gly Gln Gln Gly Pro Ser Ala Ser Ala Ala Ala
    1340            1345            1350

Ala Gly Ser Gly Gln Gln Gly Pro Gly Gln Tyr Gly Pro Tyr Ala
    1355            1360            1365

Ser Ala Ala Ala Ala Gly Gln Tyr Gly Ser Gly Pro Gly Gln
    1370            1375            1380

Gln Gly Pro Tyr Gly Pro Gly Gln Ser Gly Ser Gly Gln Gln Gly
    1385            1390            1395

Pro Gly Gln Gln Gly Pro Tyr Ala Ser Ala Ala Ala Ala Ala Gly
    1400            1405            1410

Pro Gly Gln Gln Gly Pro Tyr Gly Pro Gly Ser Ser Ala Ala Ala
    1415            1420            1425

Ala Ala Gly Gln Tyr Gly Tyr Gly Pro Gly Gln Gln Gly Pro Tyr
    1430            1435            1440

Gly Pro Gly Ala Ser Gly Gln Asn Gly Pro Gly Ser Gly Gln Tyr
    1445            1450            1455

Gly Pro Gly Gln Gln Gly Pro Gly Gln Ser Ala Ala Ala Ala Ala
    1460            1465            1470

Gly Pro Gly Gln Gln Gly Pro Tyr Gly Pro Gly Ala Ser Ala Ala
    1475            1480            1485

Ala Ala Ala Gly Gln Tyr Gly Pro Gly Gln Gln Gly Pro Gly Gln
    1490            1495            1500

Tyr Gly Pro Gly Ser Ser Gly Pro Gly Gln Gln Gly Pro Tyr Gly
    1505            1510            1515

Pro Gly Ser Ser Ala Ala Ala Ala Ala Gly Gln Tyr Gly Pro Gly
    1520            1525            1530

Gln Gln Gly Pro Tyr Gly Pro Gly Gln Ser Ala Ala Ala Ala Ala
    1535            1540            1545

Gly Gln Tyr Gln Gln Gly Pro Gly Gln Gln Gly Pro Tyr Gly Pro
    1550            1555            1560

Gly Ala Ser Gly Pro Gly Gln Gln Gly Pro Tyr Gly Pro Gly Ala
    1565            1570            1575

Ser Ala Ala Ala Ala Ala Gly Pro Gly Gln Tyr Gly Pro Gly Gln
    1580            1585            1590

Gln Gly Pro Ser Ala Ser Ala Ala Ala Ala Gly Gln Tyr Gly
    1595            1600            1605

Ser Gly Pro Gly Gln Tyr Gly Pro Tyr Gly Pro Gly Gln Ser Gly
    1610            1615            1620

Pro Gly Ser Gly Gln Gln Gly Gln Gly Pro Tyr Gly Pro Gly Ala
    1625            1630            1635

Ser Ala Ala Ala Ala Gly Gln Tyr Gly Pro Gly Gln Gln Gly
    1640            1645            1650

Pro Tyr Gly Pro Gly Gln Ser Ala Ala Ala Ala Gly Pro Gly
    1655            1660            1665

Ser Gly Gln Tyr Gly Pro Gly Ala Ser Gly Gln Asn Gly Pro Gly
    1670            1675            1680

Ser Gly Gln Tyr Gly Pro Gly Gln Gln Gly Pro Gly Gln Ser Ala
    1685            1690            1695
```

-continued

Ala Ala Ala Ala Gly Gln Tyr Gln Gln Gly Pro Gly Gln Gln Gly
1700            1705                1710

Pro Tyr Gly Pro Gly Ala Ser Ala Ala Ala Ala Gly Gln Tyr
1715            1720                1725

Gly Ser Gly Pro Gly Gln Gln Gly Pro Tyr Gly Pro Gly Gln Ser
1730            1735                1740

Gly Ser Gly Gln Gln Gly Pro Gly Gln Gln Gly Pro Tyr Ala Ser
1745            1750                1755

Ala Ala Ala Ala Ala Gly Pro Gly Ser Gly Gln Gln Gly Pro Gly
1760            1765                1770

Ala Ser Gly Gln Gln Gly Pro Tyr Gly Pro Gly Ala Ser Ala Ala
1775            1780                1785

Ala Ala Ala Gly Gln Asn Gly Pro Gly Ser Gly Gln Gln Gly Pro
1790            1795                1800

Gly Gln Ser Gly Gln Tyr Gly Pro Gly Gln Gln Gly Pro Gly Gln
1805            1810                1815

Gln Gly Pro Gly Ser Ser Ala Ala Ala Ala Gly Pro Gly Gln
1820            1825                1830

Tyr Gly Pro Gly Gln Gln Gly Pro Ser Ala Ser Ala Ala Ala Ala
1835            1840                1845

Ala Gly Pro Gly Ser Gly Gln Gln Gly Pro Gly Ala Ser Gly Gln
1850            1855                1860

Tyr Gly Pro Gly Gln Gln Gly Pro Gly Gln Gln Gly Pro Gly Ser
1865            1870                1875

Ser Ala Ala Ala Ala Ala Gly Gln Tyr Gly Ser Gly Pro Gly Gln
1880            1885                1890

Gln Gly Pro Tyr Gly Ser Ala Ala Ala Ala Gly Pro Gly Ser
1895            1900                1905

Gly Gln Tyr Gly Gln Gly Pro Tyr Gly Pro Gly Ala Ser Gly Pro
1910            1915                1920

Gly Gln Tyr Gly Pro Gly Gln Gly Pro Ser Ala Ser Ala Ala
1925            1930                1935

Ala Ala Ala Gly Ser Gly Gln Gln Gly Pro Gly Gln Tyr Gly Pro
1940            1945                1950

Tyr Ala Ser Ala Ala Ala Ala Gly Gln Tyr Gly Ser Gly Pro
1955            1960                1965

Gly Gln Gln Gly Pro Tyr Gly Pro Gly Gln Ser Gly Ser Gly Gln
1970            1975                1980

Gln Gly Pro Gly Gln Gln Gly Pro Tyr Ala Ser Ala Ala Ala
1985            1990                1995

Ala Gly Pro Gly Gln Gln Gly Pro Tyr Gly Pro Gly Ser Ser Ala
2000            2005                2010

Ala Ala Ala Gly Gln Tyr Gly Tyr Gly Pro Gly Gln Gln Gly
2015            2020                2025

Pro Tyr Gly Pro Gly Ala Ser Gly Gln Asn Gly Pro Gly Ser Gly
2030            2035                2040

Gln Tyr Gly Pro Gly Gln Gln Gly Pro Gly Gln Ser Ala Ala Ala
2045            2050                2055

Ala Ala Gly Pro Gly Gln Gln Gly Pro Tyr Gly Pro Gly Ala Ser
2060            2065                2070

Ala Ala Ala Ala Ala Gly Gln Tyr Gly Pro Gly Gln Gln Gly Pro
2075            2080                2085

Gly Gln Tyr Gly Pro Gly Ser Ser Gly Pro Gly Gln Gln Gly Pro

```
                    2090                2095                2100

Tyr Gly Pro Gly Ser Ser Ala Ala Ala Ala Gly Gln Tyr Gly
    2105                2110                2115

Pro Gly Gln Gln Gly Pro Tyr Gly Pro Gly Ser Ala Ala Ala
    2120                2125                2130

Ala Ala Gly Gln Tyr Gln Gln Gly Pro Gly Gln Gln Gly Pro Tyr
    2135                2140                2145

Gly Pro Gly Ala Ser Gly Pro Gly Gln Gln Gly Pro Tyr Gly Pro
    2150                2155                2160

Gly Ala Ser Ala Ala Ala Ala Gly Pro Gly Gln Tyr Gly Pro
    2165                2170                2175

Gly Gln Gln Gly Pro Ser Ala Ser Ala Ala Ala Ala Gly Gln
    2180                2185                2190

Tyr Gly Ser Gly Pro Gly Gln Tyr Gly Pro Tyr Gly Pro Gly Gln
    2195                2200                2205

Ser Gly Pro Gly Ser Gly Gln Gln Gly Gln Gly Pro Tyr Gly Pro
    2210                2215                2220

Gly Ala Ser Ala Ala Ala Ala Gly Gln Tyr Gly Pro Gly Gln
    2225                2230                2235

Gln Gly Pro Tyr Gly Pro Gly Gln Ser Ala Ala Ala Ala Ala Gly
    2240                2245                2250

Pro Gly Ser Gly Gln Tyr Gly Pro Gly Ala Ser Gly Gln Asn Gly
    2255                2260                2265

Pro Gly Ser Gly Gln Tyr Gly Pro Gly Gln Gln Gly Pro Gly Gln
    2270                2275                2280

Ser Ala Ala Ala Ala Gly Gln Tyr Gln Gln Gly Pro Gly Gln
    2285                2290                2295

Gln Gly Pro Tyr Gly Pro Gly Ala Ser Ala Ala Ala Ala Ala Gly
    2300                2305                2310

Gln Tyr Gly Ser Gly Pro Gly Gln Gln Gly Pro Tyr Gly Pro Gly
    2315                2320                2325

Gln Ser Gly Ser Gly Gln Gln Gly Pro Gly Gln Gln Gly Pro Tyr
    2330                2335                2340

Ala Ser Ala Ala Ala Ala Ala Gly Pro Gly Ser Gly Gln Gln Gly
    2345                2350                2355

Ser Ser Val Asp Lys Leu Ala Ala Ala Leu Glu His His His
    2360                2365                2370

His His
    2375

<210> SEQ ID NO 14
<211> LENGTH: 50
<212> TYPE: PRT
<213> ORGANISM: Araneus diadematus

<400> SEQUENCE: 14

Ser Gly Cys Asp Val Leu Val Gln Ala Leu Leu Glu Val Val Ser Ala
1               5                   10                  15

Leu Val Ser Ile Leu Gly Ser Ser Ser Ile Gly Gln Ile Asn Tyr Gly
            20                  25                  30

Ala Ser Ala Gln Tyr Thr Gln Met Val Gly Gln Ser Val Ala Gln Ala
        35                  40                  45

Leu Ala
50
```

<210> SEQ ID NO 15
<211> LENGTH: 30
<212> TYPE: PRT
<213> ORGANISM: Araneus diadematus

<400> SEQUENCE: 15

Ser Gly Cys Asp Val Leu Val Gln Ala Leu Leu Glu Val Val Ser Ala
1               5                   10                  15

Leu Val Ser Ile Leu Gly Ser Ser Ile Gly Gln Ile Asn
            20                  25                  30

<210> SEQ ID NO 16
<211> LENGTH: 21
<212> TYPE: PRT
<213> ORGANISM: Araneus diadematus

<400> SEQUENCE: 16

Ser Gly Cys Asp Val Leu Val Gln Ala Leu Leu Glu Val Val Ser Ala
1               5                   10                  15

Leu Val Ser Ile Leu
            20

<210> SEQ ID NO 17
<211> LENGTH: 1154
<212> TYPE: PRT
<213> ORGANISM: Artificial Sequence
<220> FEATURE:
<223> OTHER INFORMATION: recombinant spider silk protein
      ADF3KaiLargeNRSH1

<400> SEQUENCE: 17

Met His His His His His His His His His Ser Ser Gly Ser Ser
1               5                   10                  15

Leu Glu Val Leu Phe Gln Gly Pro Ala Arg Ala Gly Ser Gly Gln Gln
            20                  25                  30

Gly Pro Gly Gln Gln Gly Pro Gln Gln Gly Pro Gly Gln Gln Gly
            35                  40                  45

Pro Tyr Gly Pro Gly Ala Ser Ala Ala Ala Ala Ala Gly Gly Tyr
    50                  55                  60

Gly Pro Gly Ser Gly Gln Gln Gly Pro Ser Gln Gln Gly Pro Gly Gln
65                  70                  75                  80

Gln Gly Pro Gly Gly Gln Gly Pro Tyr Gly Pro Gly Ala Ser Ala Ala
                85                  90                  95

Ala Ala Ala Ala Gly Gly Tyr Gly Pro Gly Ser Gly Gln Gln Gly Pro
                100                 105                 110

Gly Gly Gln Gly Pro Tyr Gly Pro Gly Ser Ser Ala Ala Ala Ala
            115                 120                 125

Ala Gly Gly Asn Gly Pro Gly Ser Gly Gln Gln Gly Ala Gly Gln Gln
            130                 135                 140

Gly Pro Gly Gln Gln Gly Pro Gly Ala Ser Ala Ala Ala Ala Ala
145                 150                 155                 160

Gly Gly Tyr Gly Pro Gly Ser Gly Gln Gln Gly Pro Gly Gln Gln Gly
                165                 170                 175

Pro Gly Gly Gln Gly Pro Tyr Gly Pro Gly Ala Ser Ala Ala Ala
                180                 185                 190

Ala Ala Gly Gly Tyr Gly Pro Gly Ser Gly Gln Gly Pro Gly Gln Gln
            195                 200                 205

Gly Pro Gly Gly Gln Gly Pro Tyr Gly Pro Gly Ala Ser Ala Ala Ala

```
            210                 215                 220
Ala Ala Gly Gly Tyr Gly Pro Gly Ser Gly Gln Gln Pro Gly
225                 230                 235                 240

Gln Gly Pro Gly Gln Gln Gly Pro Gly Gln Gln Gly Pro Tyr Gly
                245                 250                 255

Pro Gly Ala Ser Ala Ala Ala Ala Ala Gly Gly Tyr Gly Pro Gly
            260                 265                 270

Tyr Gly Gln Gln Gly Pro Gly Gln Gln Gly Pro Gly Gln Gly Pro
        275                 280                 285

Tyr Gly Pro Gly Ala Ser Ala Ala Ser Ala Ala Ser Gly Gly Tyr Gly
    290                 295                 300

Pro Gly Ser Gly Gln Gln Gly Pro Gly Gln Gln Gly Pro Gly Gly Gln
305                 310                 315                 320

Gly Pro Tyr Gly Pro Gly Ala Ser Ala Ala Ala Ala Ala Gly Gly
                325                 330                 335

Tyr Gly Pro Gly Ser Gly Gln Gln Gly Pro Gly Gln Gln Gly Pro Gly
                340                 345                 350

Gln Gln Gly Pro Gly Gln Gln Gly Pro Gly Gln Gln Gly Pro Tyr Gly
                355                 360                 365

Pro Gly Ala Ser Ala Ala Ala Ala Ala Ala Gly Gly Tyr Gly Pro Gly
370                 375                 380

Ser Gly Gln Gln Gly Pro Gly Gln Gln Gly Pro Gly Gln Gln Gly Pro
385                 390                 395                 400

Gly Gln Gln Gly Pro Gly Gln Gln Gly Pro Gly Gln Gln Gly Pro Gly
                405                 410                 415

Gln Gln Gly Pro Gly Gln Gln Gly Pro Gly Gln Gln Gly Pro Gly Gly
                420                 425                 430

Gln Gly Ala Tyr Gly Pro Gly Ala Ser Ala Ala Ala Gly Ala Ala Gly
            435                 440                 445

Gly Tyr Gly Pro Gly Ser Gly Gln Gln Gly Pro Gly Gln Gln Gly Pro
    450                 455                 460

Gly Gln Gln Gly Pro Gly Gln Gln Gly Pro Gly Gln Gln Gly Pro Gly
465                 470                 475                 480

Gln Gln Gly Pro Gly Gln Gln Gly Pro Gly Gln Gln Gly Pro Tyr Gly
                485                 490                 495

Pro Gly Ala Ser Ala Ala Ala Ala Ala Gly Gly Tyr Gly Pro Gly
            500                 505                 510

Ser Gly Gln Gln Gly Pro Gly Gln Gln Gly Pro Gly Gln Gln Gly Pro
515                 520                 525

Gly Gly Gln Gly Pro Tyr Gly Pro Gly Ala Ala Ser Ala Ala Val Ser
530                 535                 540

Val Ser Arg Ala Arg Ala Gly Ser Gly Gln Gln Gly Pro Gly Gln Gln
545                 550                 555                 560

Gly Pro Gly Gln Gln Gly Pro Gly Gln Gln Gly Pro Tyr Gly Pro Gly
                565                 570                 575

Ala Ser Ala Ala Ala Ala Ala Ala Gly Gly Tyr Gly Pro Gly Ser Gly
            580                 585                 590

Gln Gln Gly Pro Ser Gln Gly Pro Gly Gln Gln Gly Pro Gly Gly
                595                 600                 605

Gln Gly Pro Tyr Gly Pro Gly Ala Ser Ala Ala Ala Ala Ala Gly
            610                 615                 620

Gly Tyr Gly Pro Gly Ser Gly Gln Gln Gly Pro Gly Gly Gln Gly Pro
625                 630                 635                 640
```

Tyr Gly Pro Gly Ser Ser Ala Ala Ala Ala Gly Gly Asn Gly
              645                 650                 655

Pro Gly Ser Gly Gln Gln Gly Ala Gly Gln Gly Pro Gly Gln Gln
              660                 665                 670

Gly Pro Gly Ala Ser Ala Ala Ala Ala Gly Gly Tyr Gly Pro
              675                 680                 685

Gly Ser Gly Gln Gln Gly Pro Gly Gln Gln Gly Pro Gly Gln Gly
              690                 695                 700

Pro Tyr Gly Pro Gly Ala Ser Ala Ala Ala Ala Gly Gly Tyr
705                 710                 715                 720

Gly Pro Gly Ser Gly Gln Gly Pro Gly Gln Gln Gly Pro Gly Gln
              725                 730                 735

Gly Pro Tyr Gly Pro Gly Ala Ser Ala Ala Ala Ala Gly Gly
              740                 745                 750

Tyr Gly Pro Gly Ser Gly Gln Gln Gly Pro Gly Gln Gln Gly Pro Gly
              755                 760                 765

Gln Gln Gly Pro Gly Gly Gln Gly Pro Tyr Gly Pro Gly Ala Ser Ala
770                 775                 780

Ala Ala Ala Ala Gly Gly Tyr Gly Pro Gly Tyr Gly Gln Gln Gly
785                 790                 795                 800

Pro Gly Gln Gln Gly Pro Gly Gln Gly Pro Tyr Gly Pro Gly Ala
              805                 810                 815

Ser Ala Ala Ser Ala Ala Ser Gly Gly Tyr Gly Pro Gly Ser Gly Gln
              820                 825                 830

Gln Gly Pro Gly Gln Gln Gly Pro Gly Gln Gly Pro Tyr Gly Pro
              835                 840                 845

Gly Ala Ser Ala Ala Ala Ala Ala Gly Gly Tyr Gly Pro Gly Ser
850                 855                 860

Gly Gln Gln Gly Pro Gly Gln Gln Gly Pro Gly Gln Gln Gly Pro Gly
865                 870                 875                 880

Gln Gln Gly Pro Gly Gly Gln Gly Pro Tyr Gly Pro Gly Ala Ser Ala
              885                 890                 895

Ala Ala Ala Ala Gly Gly Tyr Gly Pro Gly Ser Gly Gln Gln Gly
              900                 905                 910

Pro Gly Gln Gln Gly Pro Gly Gln Gln Gly Pro Gly Gln Gln Gly Pro
              915                 920                 925

Gly Gln Gln Gly Pro Gly Gln Gln Gly Pro Gly Gln Gln Gly Pro Gly
930                 935                 940

Gln Gln Gly Pro Gly Gln Gln Gly Pro Gly Gln Gln Gly Ala Tyr Gly
945                 950                 955                 960

Pro Gly Ala Ser Ala Ala Ala Gly Ala Ala Gly Gly Tyr Gly Pro Gly
              965                 970                 975

Ser Gly Gln Gln Gly Pro Gly Gln Gln Gly Pro Gly Gln Gln Gly Pro
              980                 985                 990

Gly Gln Gln Gly Pro Gly Gln Gln Gly Pro Gly Gln Gln Gly Pro Gly
              995                 1000                1005

Gln Gln Gly Pro Gly Gln Gln Gly Pro Tyr Gly Pro Gly Ala Ser
              1010                1015                1020

Ala Ala Ala Ala Ala Ala Gly Gly Tyr Gly Pro Gly Ser Gly Gln
              1025                1030                1035

Gln Gly Pro Gly Gln Gln Gly Pro Gly Gln Gln Gly Pro Gly Gly
              1040                1045                1050

```
Gln Gly Pro Tyr Gly Pro Gly Ala Ala Ser Ala Val Ser Val
    1055                1060                1065

Gly Gly Tyr Gly Pro Gln Ser Ser Ser Val Pro Val Ala Ser Ala
    1070                1075                1080

Val Ala Ser Arg Leu Ser Ser Pro Ala Ala Ser Ser Arg Val Ser
    1085                1090                1095

Ser Ala Val Ser Ser Leu Val Ser Ser Gly Pro Thr Lys His Ala
    1100                1105                1110

Ala Leu Ser Asn Thr Ile Ser Ser Val Val Ser Gln Val Ser Ala
    1115                1120                1125

Ser Asn Pro Gly Leu Ser Gly Cys Asp Val Leu Val Gln Ala Leu
    1130                1135                1140

Leu Glu Val Val Ser Ala Leu Val Ser Ile Leu
    1145                1150

<210> SEQ ID NO 18
<211> LENGTH: 24
<212> TYPE: PRT
<213> ORGANISM: Artificial Sequence
<220> FEATURE:
<223> OTHER INFORMATION: His tag and start codon

<400> SEQUENCE: 18

Met His His His His His His His His His Ser Ser Gly Ser Ser
1               5                   10                  15

Leu Glu Val Leu Phe Gln Gly Pro
                20

<210> SEQ ID NO 19
<211> LENGTH: 590
<212> TYPE: PRT
<213> ORGANISM: Artificial Sequence
<220> FEATURE:
<223> OTHER INFORMATION: Met-PRT410

<400> SEQUENCE: 19

Met Gly Pro Gly Gln Gln Gly Pro Tyr Gly Pro Gly Ala Ser Ala
1               5                   10                  15

Ala Ala Ala Gly Gln Asn Gly Pro Gly Ser Gly Gln Gln Gly Pro
                20                  25                  30

Gln Ser Gly Gln Tyr Gly Pro Gly Gln Gln Gly Pro Gly Gln Gly
            35                  40                  45

Pro Gly Ser Ser Ala Ala Ala Ala Gly Pro Gly Gln Tyr Gly Pro
        50                  55                  60

Gly Gln Gln Gly Pro Ser Ala Ser Ala Ala Ala Ala Gly Pro Gly
65                  70                  75                  80

Ser Gly Gln Gln Gly Pro Gly Ala Ser Gly Gln Tyr Gly Pro Gly Gln
                85                  90                  95

Gln Gly Pro Gly Gln Gln Gly Pro Gly Ser Ala Ala Ala Ala
                100                 105                 110

Gly Gln Tyr Gly Ser Gly Pro Gly Gln Gln Gly Pro Tyr Gly Ser Ala
            115                 120                 125

Ala Ala Ala Gly Pro Gly Ser Gly Gln Tyr Gly Gln Gly Pro Tyr
        130                 135                 140

Gly Pro Gly Ala Ser Gly Pro Gly Gln Tyr Gly Pro Gly Gln Gln
145                 150                 155                 160

Pro Ser Ala Ser Ala Ala Ala Ala Gly Ser Gly Gln Gln Gly Pro
                165                 170                 175
```

```
Gly Gln Tyr Gly Pro Tyr Ala Ser Ala Ala Ala Ala Gly Gln Tyr
            180                 185                 190

Gly Ser Gly Pro Gly Gln Gly Pro Tyr Gly Pro Gly Gln Ser Gly
        195                 200                 205

Ser Gly Gln Gln Gly Pro Gly Gln Gln Gly Pro Tyr Ala Ser Ala
    210                 215                 220

Ala Ala Ala Gly Pro Gly Gln Gln Gly Pro Tyr Gly Pro Gly Ser Ser
225                 230                 235                 240

Ala Ala Ala Ala Ala Gly Gln Tyr Gly Tyr Gly Pro Gly Gln Gln Gly
                245                 250                 255

Pro Tyr Gly Pro Gly Ala Ser Gly Gln Asn Gly Pro Ser Gly Gln
        260                 265                 270

Tyr Gly Pro Gly Gln Gln Gly Pro Gly Gln Ser Ala Ala Ala Ala
    275                 280                 285

Gly Pro Gly Gln Gln Gly Pro Tyr Gly Pro Gly Ala Ser Ala Ala Ala
        290                 295                 300

Ala Ala Gly Gln Tyr Gly Pro Gly Gln Gln Gly Pro Gly Gln Tyr Gly
305                 310                 315                 320

Pro Gly Ser Ser Gly Pro Gly Gln Gln Gly Pro Tyr Gly Pro Gly Ser
            325                 330                 335

Ser Ala Ala Ala Ala Ala Gly Gln Tyr Gly Pro Gly Gln Gln Gly Pro
            340                 345                 350

Tyr Gly Pro Gly Gln Ser Ala Ala Ala Ala Gly Gln Tyr Gln Gln
        355                 360                 365

Gly Pro Gly Gln Gln Gly Pro Tyr Gly Pro Gly Ala Ser Gly Pro Gly
        370                 375                 380

Gln Gln Gly Pro Tyr Gly Pro Gly Ala Ser Ala Ala Ala Ala Gly
385                 390                 395                 400

Pro Gly Gln Tyr Gly Pro Gly Gln Gly Pro Ser Ala Ser Ala Ala
            405                 410                 415

Ala Ala Ala Gly Gln Tyr Gly Ser Gly Pro Gly Gln Tyr Gly Pro Tyr
            420                 425                 430

Gly Pro Gly Gln Ser Gly Pro Gly Ser Gly Gln Gln Gly Gln Gly Pro
        435                 440                 445

Tyr Gly Pro Gly Ala Ser Ala Ala Ala Ala Gly Gln Tyr Gly Pro
450                 455                 460

Gly Gln Gln Gly Pro Tyr Gly Pro Gly Gln Ser Ala Ala Ala Ala
465                 470                 475                 480

Gly Pro Gly Ser Gly Gln Tyr Gly Pro Gly Ala Ser Gly Gln Asn Gly
            485                 490                 495

Pro Gly Ser Gly Gln Tyr Gly Pro Gly Gln Gln Gly Pro Gly Gln Ser
            500                 505                 510

Ala Ala Ala Ala Ala Gly Gln Tyr Gln Gln Gly Pro Gly Gln Gln Gly
            515                 520                 525

Pro Tyr Gly Pro Gly Ala Ser Ala Ala Ala Ala Gly Gln Tyr Gly
        530                 535                 540

Ser Gly Pro Gly Gln Gln Gly Pro Tyr Gly Pro Gly Gln Ser Gly Ser
545                 550                 555                 560

Gly Gln Gln Gly Pro Gly Gln Gly Pro Tyr Ala Ser Ala Ala Ala
                565                 570                 575

Ala Ala Gly Pro Gly Ser Gly Gln Gln Gly Pro Gly Ala Ser
        580                 585                 590
```

<210> SEQ ID NO 20
<211> LENGTH: 612
<212> TYPE: PRT
<213> ORGANISM: Artificial Sequence
<220> FEATURE:
<223> OTHER INFORMATION: Met-PRT720

<400> SEQUENCE: 20

```
Met Gly Pro Gly Gln Gln Gly Pro Tyr Gly Pro Gly Ala Ser Ala Ala
1               5                   10                  15

Ala Ala Ala Gly Gln Asn Gly Pro Gly Ser Gly Gln Gln Gly Pro Gly
            20                  25                  30

Gln Ser Gly Gln Tyr Gly Pro Gly Gln Gln Gly Pro Gly Gln Gln Gly
        35                  40                  45

Pro Gly Ser Ser Ala Ala Ala Ala Gly Pro Gly Gln Tyr Val Leu
    50                  55                  60

Ile Gly Pro Gly Gln Gln Val Leu Ile Gly Pro Ser Ala Ser Ala Ala
65                  70                  75                  80

Ala Ala Ala Gly Pro Gly Ser Gly Gln Gln Gly Pro Gly Ala Ser Gly
                85                  90                  95

Gln Tyr Gly Pro Gly Gln Gln Gly Pro Gly Gln Gln Gly Pro Gly Ser
            100                 105                 110

Ser Ala Ala Ala Ala Gly Ser Tyr Gly Ser Val Leu Ile Gly Pro
    115                 120                 125

Gly Gln Gln Val Leu Ile Gly Pro Tyr Gly Ser Ala Ala Ala Ala
    130                 135                 140

Gly Pro Gly Ser Gly Gln Tyr Gly Gln Gly Pro Tyr Gly Pro Gly Ala
145                 150                 155                 160

Ser Gly Pro Gly Gln Tyr Gly Pro Gly Gln Gln Gly Pro Ser Ala Ser
                165                 170                 175

Ala Ala Ala Ala Gly Ser Gly Gln Gln Val Leu Ile Gly Pro Gly
            180                 185                 190

Gln Tyr Val Leu Ile Gly Pro Tyr Ala Ser Ala Ala Ala Ala Gly
    195                 200                 205

Gln Tyr Gly Ser Gly Pro Gly Gln Gln Gly Pro Tyr Gly Pro Gly Gln
    210                 215                 220

Ser Gly Ser Gly Gln Gln Gly Pro Gly Gln Gln Gly Pro Tyr Ala Ser
225                 230                 235                 240

Ala Ala Ala Ala Gly Pro Gly Gln Gln Val Leu Ile Gly Pro Tyr
            245                 250                 255

Val Leu Ile Gly Pro Gly Ser Ser Ala Ala Ala Ala Gly Gln Tyr
    260                 265                 270

Gly Tyr Gly Pro Gly Gln Gln Gly Pro Tyr Gly Pro Gly Ala Ser Gly
    275                 280                 285

Gln Asn Gly Pro Gly Ser Gly Gln Tyr Gly Pro Gly Gln Gln Gly Pro
    290                 295                 300

Gly Gln Ser Ala Ala Ala Ala Ala Gly Pro Gly Gln Gln Val Leu Ile
305                 310                 315                 320

Gly Pro Tyr Val Leu Ile Gly Pro Gly Ala Ser Ala Ala Ala Ala
            325                 330                 335

Gly Gln Tyr Gly Pro Gly Gln Gln Gly Pro Gly Gln Tyr Gly Pro Gly
        340                 345                 350

Ser Ser Gly Pro Gly Gln Gln Gly Pro Tyr Gly Pro Gly Ser Ser Ala
            355                 360                 365
```

```
Ala Ala Ala Ala Gly Ser Tyr Gly Pro Gly Gln Gln Val Leu Ile Gly
        370                 375                 380

Pro Tyr Val Leu Ile Gly Pro Gly Pro Ser Ala Ala Ala Ala Ala Gly
385                 390                 395                 400

Gln Tyr Gln Gln Gly Pro Gly Gln Gln Gly Pro Tyr Gly Pro Gly Ala
                405                 410                 415

Ser Gly Pro Gly Gln Gln Gly Pro Tyr Gly Pro Gly Ala Ser Ala Ala
            420                 425                 430

Ala Ala Ala Gly Pro Gly Gln Tyr Val Leu Ile Gly Pro Gly Gln Gln
        435                 440                 445

Val Leu Ile Gly Pro Ser Ala Ser Ala Ala Ala Ala Gly Gln Tyr
450                 455                 460

Gly Ser Gly Pro Gly Gln Tyr Gly Pro Tyr Gly Pro Gly Gln Ser Gly
465                 470                 475                 480

Pro Gly Ser Gly Gln Gln Gly Gln Gly Pro Tyr Gly Pro Gly Ala Ser
            485                 490                 495

Ala Ala Ala Ala Gly Ser Tyr Gly Pro Gly Gln Gln Val Leu Ile
        500                 505                 510

Gly Pro Tyr Val Leu Ile Gly Pro Gly Pro Ser Ala Ala Ala Ala
    515                 520                 525

Gly Pro Gly Ser Gly Gln Tyr Gly Pro Gly Ala Ser Gly Gln Asn Gly
        530                 535                 540

Pro Gly Ser Gly Gln Tyr Gly Pro Gly Gln Gln Gly Pro Gly Gln Ser
545                 550                 555                 560

Ala Ala Ala Ala Ala Gly Gln Tyr Gln Gln Val Leu Ile Gly Pro Gly
                565                 570                 575

Gln Gln Gly Pro Tyr Val Leu Ile Gly Pro Gly Ala Ser Ala Ala Ala
            580                 585                 590

Ala Ala Gly Pro Gly Ser Gly Gln Gln Val Leu Ile Gly Pro Gly Ala
        595                 600                 605

Ser Val Leu Ile
        610

<210> SEQ ID NO 21
<211> LENGTH: 565
<212> TYPE: PRT
<213> ORGANISM: Artificial Sequence
<220> FEATURE:
<223> OTHER INFORMATION: Met-PRT468

<400> SEQUENCE: 21

Met Gly Pro Gly Gln Gln Gly Pro Tyr Gly Pro Gly Ala Ser Ala Ala
1               5                   10                  15

Ala Ala Ala Ala Gly Ser Asn Gly Pro Gly Ser Gly Gln Gln Gly
            20                  25                  30

Pro Gly Gln Ser Gly Gln Tyr Gly Pro Gly Gln Gln Gly Pro Gly Gln
        35                  40                  45

Gln Gly Pro Gly Ser Ser Ala Ala Ala Ala Ala Gly Pro Gly
    50                  55                  60

Gln Tyr Gly Pro Gly Gln Gln Gly Pro Ser Ala Ser Ala Ala Ala Ala
65                  70                  75                  80

Ala Ala Ala Gly Pro Gly Ser Gly Gln Gln Gly Pro Gly Ala Ser Gly
                85                  90                  95

Gln Tyr Gly Pro Gly Gln Gln Gly Pro Gly Gln Gln Gly Pro Gly Ser
            100                 105                 110
```

```
Ser Ala Ala Ala Ala Ala Ala Gly Ser Tyr Gly Ser Gly Pro Gly
            115                 120                 125

Gln Gln Gly Pro Tyr Gly Ser Ala Ala Ala Ala Ala Ala Gly Pro
    130                 135                 140

Gly Ser Gly Gln Tyr Gly Gln Gly Pro Tyr Gly Pro Gly Ala Ser Gly
145                 150                 155                 160

Pro Gly Gln Tyr Gly Pro Gly Gln Gly Pro Ser Ala Ser Ala Ala
                165                 170                 175

Ala Ala Ala Ala Ala Gly Ser Gly Gln Gly Pro Gly Gln Tyr Gly
            180                 185                 190

Pro Tyr Ala Ser Ala Ala Ala Ala Ala Gly Ser Tyr Gly Ser
    195                 200                 205

Gly Pro Gly Gln Gln Gly Pro Tyr Gly Pro Gly Gln Ser Gly Ser Gly
210                 215                 220

Gln Gln Gly Pro Gly Gln Gly Pro Tyr Ala Ser Ala Ala Ala Ala
225                 230                 235                 240

Ala Ala Ala Gly Pro Gly Gln Gln Gly Pro Tyr Gly Pro Gly Ser Ser
            245                 250                 255

Ala Ala Ala Ala Ala Ala Ala Gly Ser Tyr Gly Tyr Gly Pro Gly Gln
            260                 265                 270

Gln Gly Pro Tyr Gly Pro Gly Ala Ser Gly Gln Asn Gly Pro Gly Ser
    275                 280                 285

Gly Gln Tyr Gly Pro Gly Gln Gly Pro Gly Pro Ser Ala Ala Ala
    290                 295                 300

Ala Ala Ala Ala Gly Pro Gly Gln Gln Gly Pro Tyr Gly Pro Gly Ala
305                 310                 315                 320

Ser Ala Ala Ala Ala Ala Ala Gly Ser Tyr Gly Pro Gly Gln Gln
            325                 330                 335

Gly Pro Gly Gln Tyr Gly Pro Gly Ser Ser Gly Pro Gly Gln Gln Gly
            340                 345                 350

Pro Tyr Gly Pro Gly Ser Ser Ala Ala Ala Ala Ala Ala Gly Ser
    355                 360                 365

Tyr Gly Pro Gly Gln Gln Gly Pro Tyr Gly Pro Gly Pro Ser Ala Ala
    370                 375                 380

Ala Ala Ala Ala Ala Gly Ser Tyr Gln Gln Gly Pro Gly Gln Gln Gly
385                 390                 395                 400

Pro Tyr Gly Pro Gly Ala Ser Gly Pro Gly Gln Gln Gly Pro Tyr Gly
            405                 410                 415

Pro Gly Ala Ser Ala Ala Ala Ala Ala Gly Pro Gly Gln Tyr
            420                 425                 430

Gly Pro Gly Gln Gln Gly Pro Ser Ala Ser Ala Ala Ala Ala Ala
            435                 440                 445

Ala Gly Ser Tyr Gly Ser Gly Pro Gly Gln Tyr Gly Pro Tyr Gly Pro
    450                 455                 460

Gly Gln Ser Gly Pro Gly Ser Gly Gln Gly Gln Gly Pro Tyr Gly
465                 470                 475                 480

Pro Gly Ala Ser Ala Ala Ala Ala Ala Ala Gly Ser Tyr Gly Pro
            485                 490                 495

Gly Gln Gln Gly Pro Tyr Gly Pro Gly Ser Ala Ala Ala Ala
            500                 505                 510

Ala Ala Gly Pro Gly Ser Gly Gln Tyr Gly Pro Gly Ala Ser Gly Gln
            515                 520                 525

Asn Gly Pro Gly Ser Gly Gln Tyr Gly Pro Gly Gln Gln Gly Pro Gly
```

```
                530                 535                 540
Pro Ser Ala Ala Ala Ala Ala Ala Gly Pro Gly Ser Gln Gln
545                 550                 555                 560

Gly Pro Gly Ala Ser
                565

<210> SEQ ID NO 22
<211> LENGTH: 592
<212> TYPE: PRT
<213> ORGANISM: Artificial Sequence
<220> FEATURE:
<223> OTHER INFORMATION: Met-PRT665

<400> SEQUENCE: 22

Met Gly Pro Gly Gln Gln Gly Pro Tyr Gly Pro Gly Ala Ser Ala Ala
1               5                   10                  15

Ala Ala Ala Ala Ala Gly Ser Asn Gly Pro Gly Ser Gly Gln Gln Gly
                20                  25                  30

Pro Gly Gln Ser Gly Gln Tyr Gly Pro Gly Gln Gln Gly Pro Gly Gln
            35                  40                  45

Gln Gly Pro Gly Ser Ser Ala Ala Ala Ala Ala Ala Gly Pro Gly
50                  55                  60

Gln Tyr Val Leu Ile Gly Pro Gly Gln Gly Pro Ser Ala Ser Ala
65                  70                  75                  80

Ala Ala Ala Ala Ala Gly Pro Gly Ser Gly Gln Gln Gly Pro Gly
                85                  90                  95

Ala Ser Gly Gln Tyr Gly Pro Gly Gln Gln Gly Pro Gly Gln Gln Gly
            100                 105                 110

Pro Gly Ser Ser Ala Ala Ala Ala Ala Ala Gly Ser Tyr Gly Ser
            115                 120                 125

Val Leu Ile Gly Pro Gly Gln Gln Pro Tyr Gly Ser Ala Ala Ala
130                 135                 140

Ala Ala Ala Ala Gly Pro Gly Ser Gly Gln Tyr Gly Gln Gly Pro Tyr
145                 150                 155                 160

Gly Pro Gly Ala Ser Gly Pro Gly Gln Tyr Gly Pro Gly Gln Gln Gly
                165                 170                 175

Pro Ser Ala Ser Ala Ala Ala Ala Ala Ala Gly Ser Gly Gln Gln
            180                 185                 190

Val Leu Ile Gly Pro Gly Gln Tyr Gly Pro Tyr Ala Ser Ala Ala Ala
            195                 200                 205

Ala Ala Ala Ala Gly Ser Tyr Gly Ser Gly Pro Gly Gln Gln Gly Pro
210                 215                 220

Tyr Gly Pro Gly Gln Ser Gly Ser Gly Gln Gln Gly Pro Gly Gln Gln
225                 230                 235                 240

Gly Pro Tyr Ala Ser Ala Ala Ala Ala Ala Ala Gly Pro Gly Gln
            245                 250                 255

Gln Val Leu Ile Gly Pro Tyr Gly Pro Gly Ser Ser Ala Ala Ala Ala
                260                 265                 270

Ala Ala Ala Gly Ser Tyr Gly Tyr Gly Pro Gly Gln Gln Gly Pro Tyr
            275                 280                 285

Gly Pro Gly Ala Ser Gly Gln Asn Gly Pro Gly Ser Gly Gln Tyr Gly
            290                 295                 300

Pro Gly Gln Gln Gly Pro Gly Pro Ser Ala Ala Ala Ala Ala Ala
305                 310                 315                 320

Gly Pro Gly Gln Gln Val Leu Ile Gly Pro Tyr Gly Pro Gly Ala Ser
```

```
                    325                 330                 335
Ala Ala Ala Ala Ala Ala Gly Ser Tyr Gly Pro Gly Gln Gln Gly
                340                 345                 350

Pro Gly Gln Tyr Gly Pro Gly Ser Ser Gly Pro Gly Gln Gln Gly Pro
                355                 360                 365

Tyr Gly Pro Gly Ser Ser Ala Ala Ala Ala Ala Ala Gly Ser Tyr
                370                 375                 380

Gly Pro Gly Gln Gln Val Leu Ile Gly Pro Tyr Gly Pro Gly Pro Ser
385                 390                 395                 400

Ala Ala Ala Ala Ala Ala Gly Ser Tyr Gln Gln Gly Pro Gly Gln
                405                 410                 415

Gln Gly Pro Tyr Gly Pro Gly Ala Ser Gly Pro Gly Gln Gln Gly Pro
                420                 425                 430

Tyr Gly Pro Gly Ala Ser Ala Ala Ala Ala Ala Ala Gly Pro Gly
                435                 440                 445

Gln Tyr Val Leu Ile Gly Pro Gly Gln Gln Gly Pro Ser Ala Ser Ala
450                 455                 460

Ala Ala Ala Ala Ala Gly Ser Tyr Gly Ser Gly Pro Gly Gln Tyr
465                 470                 475                 480

Gly Pro Tyr Gly Pro Gly Gln Ser Gly Pro Gly Ser Gly Gln Gln Gly
                485                 490                 495

Gln Gly Pro Tyr Gly Pro Gly Ala Ser Ala Ala Ala Ala Ala Ala
                500                 505                 510

Gly Ser Tyr Gly Pro Gly Gln Gln Val Leu Ile Gly Pro Tyr Gly Pro
                515                 520                 525

Gly Pro Ser Ala Ala Ala Ala Ala Ala Gly Pro Gly Ser Gly Gln
                530                 535                 540

Tyr Gly Pro Gly Ala Ser Gly Gln Asn Gly Pro Gly Ser Gly Gln Tyr
545                 550                 555                 560

Gly Pro Gly Gln Gln Gly Pro Gly Pro Ser Ala Ala Ala Ala Ala
                565                 570                 575

Ala Gly Pro Gly Ser Gly Gln Gln Gly Pro Gly Ala Ser Val Leu Ile
                580                 585                 590

<210> SEQ ID NO 23
<211> LENGTH: 619
<212> TYPE: PRT
<213> ORGANISM: Artificial Sequence
<220> FEATURE:
<223> OTHER INFORMATION: Met-PRT666

<400> SEQUENCE: 23

Met Gly Pro Gly Gln Gln Gly Pro Tyr Gly Pro Gly Ala Ser Ala Ala
1               5                   10                  15

Ala Ala Ala Ala Ala Gly Ser Asn Gly Pro Gly Ser Gly Gln Gln Gly
                20                  25                  30

Pro Gly Gln Ser Gly Gln Tyr Gly Pro Gly Gln Gln Gly Pro Gly Gln
                35                  40                  45

Gln Gly Pro Gly Ser Ser Ala Ala Ala Ala Ala Ala Gly Pro Gly
                50                  55                  60

Gln Tyr Val Leu Ile Gly Pro Gly Gln Gln Val Leu Ile Gly Pro Ser
65                  70                  75                  80

Ala Ser Ala Ala Ala Ala Ala Ala Gly Pro Gly Ser Gly Gln Gln
                85                  90                  95

Gly Pro Gly Ala Ser Gly Gln Tyr Gly Pro Gly Gln Gln Gly Pro Gly
```

-continued

```
                100             105                 110
Gln Gln Gly Pro Gly Ser Ser Ala Ala Ala Ala Ala Gly Ser
            115             120             125

Tyr Gly Ser Val Leu Ile Gly Pro Gly Gln Val Leu Ile Gly Pro
            130             135         140

Tyr Gly Ser Ala Ala Ala Ala Ala Ala Gly Pro Gly Ser Gly Gln
145             150             155             160

Tyr Gly Gln Gly Pro Tyr Gly Pro Gly Ala Ser Gly Pro Gly Gln Tyr
            165             170             175

Gly Pro Gly Gln Gln Gly Pro Ser Ala Ser Ala Ala Ala Ala
            180             185             190

Ala Gly Ser Gly Gln Gln Val Leu Ile Gly Pro Gly Gln Tyr Val Leu
            195             200             205

Ile Gly Pro Tyr Ala Ser Ala Ala Ala Ala Ala Gly Ser Tyr
            210             215             220

Gly Ser Gly Pro Gly Gln Gln Gly Pro Tyr Gly Pro Gly Gln Ser Gly
225             230             235             240

Ser Gly Gln Gln Gly Pro Gly Gln Gln Gly Pro Tyr Ala Ser Ala Ala
            245             250             255

Ala Ala Ala Ala Ala Gly Pro Gly Gln Gln Val Leu Ile Gly Pro Tyr
            260             265             270

Val Leu Ile Gly Pro Gly Ser Ser Ala Ala Ala Ala Ala Gly
            275             280             285

Ser Tyr Gly Tyr Gly Pro Gly Gln Gln Gly Pro Tyr Gly Pro Gly Ala
            290             295             300

Ser Gly Gln Asn Gly Pro Gly Ser Gly Gln Tyr Gly Pro Gly Gln Gln
305             310             315             320

Gly Pro Gly Pro Ser Ala Ala Ala Ala Ala Ala Gly Pro Gly Gln
            325             330             335

Gln Val Leu Ile Gly Pro Tyr Val Leu Ile Gly Pro Gly Ala Ser Ala
            340             345             350

Ala Ala Ala Ala Ala Gly Ser Tyr Gly Pro Gly Gln Gln Gly Pro
            355             360             365

Gly Gln Tyr Gly Pro Gly Ser Ser Gly Pro Gly Gln Gln Gly Pro Tyr
            370             375             380

Gly Pro Gly Ser Ser Ala Ala Ala Ala Ala Ala Gly Ser Tyr Gly
385             390             395             400

Pro Gly Gln Gln Val Leu Ile Gly Pro Tyr Val Leu Ile Gly Pro Gly
            405             410             415

Pro Ser Ala Ala Ala Ala Ala Ala Gly Ser Tyr Gln Gln Gly Pro
            420             425             430

Gly Gln Gln Gly Pro Tyr Gly Pro Gly Ala Ser Gly Pro Gly Gln Gln
            435             440             445

Gly Pro Tyr Gly Pro Gly Ala Ser Ala Ala Ala Ala Ala Ala Gly
            450             455             460

Pro Gly Gln Tyr Val Leu Ile Gly Pro Gly Gln Gln Val Leu Ile Gly
465             470             475             480

Pro Ser Ala Ser Ala Ala Ala Ala Ala Gly Ser Tyr Gly Ser
            485             490             495

Gly Pro Gly Gln Tyr Gly Pro Tyr Gly Pro Gly Gln Ser Gly Pro Gly
            500             505             510

Ser Gly Gln Gln Gly Gln Gly Pro Tyr Gly Pro Gly Ala Ser Ala Ala
            515             520             525
```

Ala Ala Ala Ala Ala Gly Ser Tyr Gly Pro Gly Gln Gln Val Leu Ile
            530                 535                 540

Gly Pro Tyr Val Leu Ile Gly Pro Gly Pro Ser Ala Ala Ala Ala Ala
545                 550                 555                 560

Ala Ala Gly Pro Gly Ser Gly Gln Tyr Gly Pro Gly Ala Ser Gly Gln
            565                 570                 575

Asn Gly Pro Gly Ser Gly Gln Tyr Gly Pro Gly Gln Gln Gly Pro Gly
            580                 585                 590

Pro Ser Ala Ala Ala Ala Ala Ala Gly Pro Gly Ser Gly Gln Gln
        595                 600                 605

Val Leu Ile Gly Pro Gly Ala Ser Val Leu Ile
    610                 615

<210> SEQ ID NO 24
<211> LENGTH: 623
<212> TYPE: PRT
<213> ORGANISM: Artificial Sequence
<220> FEATURE:
<223> OTHER INFORMATION: PRT468

<400> SEQUENCE: 24

Met His His His His His Ser Ser Gly Ser Ser Gly Pro Gly Gln
1               5                   10                  15

Gln Gly Pro Tyr Gly Pro Gly Ala Ser Ala Ala Ala Ala Gly Gln
            20                  25                  30

Asn Gly Pro Gly Ser Gly Gln Gln Gly Pro Gly Gln Ser Gly Gln Tyr
            35                  40                  45

Gly Pro Gly Gln Gln Gly Pro Gly Gln Gln Gly Pro Gly Ser Ser Ala
50                  55                  60

Ala Ala Ala Gly Pro Gly Gln Tyr Val Leu Ile Gly Pro Gly Gln
65                  70                  75                  80

Gln Val Leu Ile Gly Pro Ser Ala Ser Ala Ala Ala Ala Gly Pro
                85                  90                  95

Gly Ser Gly Gln Gln Gly Pro Gly Ala Ser Gly Gln Tyr Gly Pro Gly
            100                 105                 110

Gln Gln Gly Pro Gly Gln Gln Gly Pro Gly Ser Ser Ala Ala Ala Ala
        115                 120                 125

Ala Gly Ser Tyr Gly Ser Val Leu Ile Gly Pro Gly Gln Gln Val Leu
            130                 135                 140

Ile Gly Pro Tyr Gly Ser Ala Ala Ala Ala Gly Pro Gly Ser Gly
145                 150                 155                 160

Gln Tyr Gly Gln Gly Pro Tyr Gly Pro Gly Ala Ser Gly Pro Gly Gln
            165                 170                 175

Tyr Gly Pro Gly Gln Gln Gly Pro Ser Ala Ser Ala Ala Ala Ala Ala
            180                 185                 190

Gly Ser Gly Gln Gln Val Leu Ile Gly Pro Gly Gln Tyr Val Leu Ile
        195                 200                 205

Gly Pro Tyr Ala Ser Ala Ala Ala Ala Gly Gln Tyr Gly Ser Gly
    210                 215                 220

Pro Gly Gln Gln Gly Pro Tyr Gly Pro Gly Ser Gly Ser Gly Gln
225                 230                 235                 240

Gln Gly Pro Gly Gln Gln Gly Pro Tyr Ala Ser Ala Ala Ala Ala Ala
            245                 250                 255

Gly Pro Gly Gln Gln Val Leu Ile Gly Pro Tyr Val Leu Ile Gly Pro
            260                 265                 270

Gly Ser Ser Ala Ala Ala Ala Gly Gln Tyr Gly Tyr Gly Pro Gly
            275                 280                 285

Gln Gln Gly Pro Tyr Gly Pro Gly Ala Ser Gly Gln Asn Gly Pro Gly
        290                 295                 300

Ser Gly Gln Tyr Gly Pro Gly Gln Gln Gly Pro Gly Gln Ser Ala Ala
305                 310                 315                 320

Ala Ala Ala Gly Pro Gly Gln Gln Val Leu Ile Gly Pro Tyr Val Leu
                325                 330                 335

Ile Gly Pro Gly Ala Ser Ala Ala Ala Ala Gly Gln Tyr Gly Pro
            340                 345                 350

Gly Gln Gln Gly Pro Gly Gln Tyr Gly Pro Gly Ser Ser Gly Pro Gly
            355                 360                 365

Gln Gln Gly Pro Tyr Gly Pro Gly Ser Ser Ala Ala Ala Ala Gly
        370                 375                 380

Ser Tyr Gly Pro Gly Gln Gln Val Leu Ile Gly Pro Tyr Val Leu Ile
385                 390                 395                 400

Gly Pro Gly Pro Ser Ala Ala Ala Ala Gly Gln Tyr Gln Gln Gly
                405                 410                 415

Pro Gly Gln Gln Gly Pro Tyr Gly Pro Gly Ala Ser Gly Pro Gly Gln
            420                 425                 430

Gln Gly Pro Tyr Gly Pro Gly Ala Ser Ala Ala Ala Ala Gly Pro
        435                 440                 445

Gly Gln Tyr Val Leu Ile Gly Pro Gln Gln Val Leu Ile Gly Pro
        450                 455                 460

Ser Ala Ser Ala Ala Ala Ala Gly Gln Tyr Gly Ser Gly Pro Gly
465                 470                 475                 480

Gln Tyr Gly Pro Tyr Gly Pro Gly Gln Ser Gly Pro Gly Ser Gly Gln
            485                 490                 495

Gln Gly Gln Gly Pro Tyr Gly Pro Gly Ala Ser Ala Ala Ala Ala
            500                 505                 510

Gly Ser Tyr Gly Pro Gly Gln Gln Val Leu Ile Gly Pro Tyr Val Leu
        515                 520                 525

Ile Gly Pro Gly Pro Ser Ala Ala Ala Ala Gly Pro Gly Ser Gly
            530                 535                 540

Gln Tyr Gly Pro Gly Ala Ser Gly Gln Asn Gly Pro Gly Ser Gly Gln
545                 550                 555                 560

Tyr Gly Pro Gly Gln Gln Gly Pro Gly Gln Ser Ala Ala Ala Ala
            565                 570                 575

Gly Gln Tyr Gln Gln Val Leu Ile Gly Pro Gly Gln Gly Pro Tyr
        580                 585                 590

Val Leu Ile Gly Pro Gly Ala Ser Ala Ala Ala Ala Gly Pro Gly
            595                 600                 605

Ser Gly Gln Gln Val Leu Ile Gly Pro Gly Ala Ser Val Leu Ile
610                 615                 620

<210> SEQ ID NO 25
<211> LENGTH: 603
<212> TYPE: PRT
<213> ORGANISM: Artificial Sequence
<220> FEATURE:
<223> OTHER INFORMATION: PRT665

<400> SEQUENCE: 25

Met His His His His His Ser Ser Gly Ser Ser Gly Pro Gly Gln
1               5                   10                  15

-continued

Gln Gly Pro Tyr Gly Pro Gly Ala Ser Ala Ala Ala Ala Ala Ala
                20                  25                  30
Gly Ser Asn Gly Pro Gly Ser Gly Gln Gln Gly Pro Gly Gln Ser Gly
        35                  40                  45
Gln Tyr Gly Pro Gly Gln Gln Gly Pro Gly Gln Gly Pro Gly Ser
    50                  55                  60
Ser Ala Ala Ala Ala Ala Ala Gly Pro Gly Gln Tyr Val Leu Ile
65                  70                  75                  80
Gly Pro Gly Gln Gln Gly Pro Ser Ala Ser Ala Ala Ala Ala Ala
                85                  90                  95
Ala Gly Pro Gly Ser Gln Gln Gly Pro Gly Ala Ser Gly Gln Tyr
                100                 105                 110
Gly Pro Gly Gln Gln Gly Pro Gln Gln Gly Pro Gly Ser Ser Ala
            115                 120                 125
Ala Ala Ala Ala Ala Gly Ser Tyr Gly Ser Val Leu Ile Gly Pro
        130                 135                 140
Gly Gln Gln Gly Pro Tyr Gly Ser Ala Ala Ala Ala Ala Ala Gly
145                 150                 155                 160
Pro Gly Ser Gly Gln Tyr Gly Gln Gly Pro Tyr Gly Pro Gly Ala Ser
                165                 170                 175
Gly Pro Gly Gln Tyr Gly Pro Gly Gln Gln Gly Pro Ser Ala Ser Ala
                180                 185                 190
Ala Ala Ala Ala Ala Gly Ser Gly Gln Gln Val Leu Ile Gly Pro
            195                 200                 205
Gly Gln Tyr Gly Pro Tyr Ala Ser Ala Ala Ala Ala Ala Ala Gly
            210                 215                 220
Ser Tyr Gly Ser Gly Pro Gly Gln Gln Gly Pro Tyr Gly Pro Gly Gln
225                 230                 235                 240
Ser Gly Ser Gly Gln Gln Gly Pro Gly Gln Gln Gly Pro Tyr Ala Ser
                245                 250                 255
Ala Ala Ala Ala Ala Ala Gly Pro Gly Gln Gln Val Leu Ile Gly
            260                 265                 270
Pro Tyr Gly Pro Gly Ser Ser Ala Ala Ala Ala Ala Ala Gly Ser
        275                 280                 285
Tyr Gly Tyr Gly Pro Gly Gln Gln Gly Pro Tyr Gly Pro Gly Ala Ser
                290                 295                 300
Gly Gln Asn Gly Pro Gly Ser Gly Gln Tyr Gly Pro Gly Gln Gln Gly
305                 310                 315                 320
Pro Gly Pro Ser Ala Ala Ala Ala Ala Ala Gly Pro Gly Gln Gln
            325                 330                 335
Val Leu Ile Gly Pro Tyr Gly Pro Gly Ala Ser Ala Ala Ala Ala
            340                 345                 350
Ala Ala Gly Ser Tyr Gly Pro Gly Gln Gln Gly Pro Gly Gln Tyr Gly
        355                 360                 365
Pro Gly Ser Ser Gly Pro Gly Gln Gln Gly Pro Tyr Gly Pro Gly Ser
        370                 375                 380
Ser Ala Ala Ala Ala Ala Ala Ala Gly Ser Tyr Gly Pro Gly Gln Gln
385                 390                 395                 400
Val Leu Ile Gly Pro Tyr Gly Pro Gly Pro Ser Ala Ala Ala Ala Ala
                405                 410                 415
Ala Ala Gly Ser Tyr Gln Gln Gly Pro Gly Gln Gln Gly Pro Tyr Gly
        420                 425                 430

```
Pro Gly Ala Ser Gly Pro Gly Gln Gln Gly Pro Tyr Gly Pro Gly Ala
            435                 440                 445
Ser Ala Ala Ala Ala Ala Ala Gly Pro Gly Gln Tyr Val Leu Ile
    450                 455                 460
Gly Pro Gly Gln Gln Gly Pro Ser Ala Ser Ala Ala Ala Ala Ala
465                 470                 475                 480
Ala Gly Ser Tyr Gly Ser Gly Pro Gln Tyr Gly Pro Tyr Gly Pro
            485                 490                 495
Gly Gln Ser Gly Pro Gly Ser Gly Gln Gln Gly Pro Tyr Gly
            500                 505                 510
Pro Gly Ala Ser Ala Ala Ala Ala Ala Gly Ser Tyr Gly Pro
        515                 520                 525
Gly Gln Gln Val Leu Ile Gly Pro Tyr Gly Pro Gly Pro Ser Ala Ala
        530                 535                 540
Ala Ala Ala Ala Ala Gly Pro Gly Ser Gly Gln Tyr Gly Pro Gly Ala
545                 550                 555                 560
Ser Gly Gln Asn Gly Pro Gly Ser Gly Gln Tyr Gly Pro Gly Gln Gln
                565                 570                 575
Gly Pro Gly Pro Ser Ala Ala Ala Ala Ala Ala Gly Pro Gly Ser
            580                 585                 590
Gly Gln Gln Gly Pro Gly Ala Ser Val Leu Ile
        595                 600

<210> SEQ ID NO 26
<211> LENGTH: 630
<212> TYPE: PRT
<213> ORGANISM: Artificial Sequence
<220> FEATURE:
<223> OTHER INFORMATION: PRT666

<400> SEQUENCE: 26

Met His His His His His Ser Ser Gly Ser Ser Gly Pro Gly Gln
1               5                   10                  15
Gln Gly Pro Tyr Gly Pro Gly Ala Ser Ala Ala Ala Ala Ala Ala
                20                  25                  30
Gly Ser Asn Gly Pro Gly Ser Gly Gln Gln Gly Pro Gly Gln Ser Gly
        35                  40                  45
Gln Tyr Gly Pro Gly Gln Gln Gly Pro Gly Gln Gln Gly Pro Gly Ser
    50                  55                  60
Ser Ala Ala Ala Ala Ala Ala Gly Pro Gly Gln Tyr Val Leu Ile
65                  70                  75                  80
Gly Pro Gly Gln Gln Val Leu Ile Gly Pro Ser Ala Ser Ala Ala Ala
                85                  90                  95
Ala Ala Ala Ala Gly Pro Gly Ser Gly Gln Gln Gly Pro Gly Ala Ser
            100                 105                 110
Gly Gln Tyr Gly Pro Gly Gln Gln Gly Pro Gly Gln Gln Gly Pro Gly
        115                 120                 125
Ser Ser Ala Ala Ala Ala Ala Ala Gly Ser Tyr Gly Ser Val Leu
    130                 135                 140
Ile Gly Pro Gly Gln Gln Val Leu Ile Gly Pro Tyr Gly Ser Ala Ala
145                 150                 155                 160
Ala Ala Ala Ala Ala Gly Pro Gly Ser Gly Gln Tyr Gly Gln Gly Pro
                165                 170                 175
Tyr Gly Pro Gly Ala Ser Gly Pro Gly Gln Tyr Gly Pro Gly Gln Gln
            180                 185                 190
```

```
Gly Pro Ser Ala Ser Ala Ala Ala Ala Ala Gly Ser Gly Gln
        195                 200                 205

Gln Val Leu Ile Gly Pro Gly Gln Tyr Val Leu Ile Gly Pro Tyr Ala
        210                 215                 220

Ser Ala Ala Ala Ala Ala Ala Gly Ser Tyr Gly Ser Gly Pro Gly
225                 230                 235                 240

Gln Gln Gly Pro Tyr Gly Pro Gly Gln Gly Ser Gly Gln Gln Gly
                245                 250                 255

Pro Gly Gln Gln Gly Pro Tyr Ala Ser Ala Ala Ala Ala Ala Ala
                260                 265                 270

Gly Pro Gly Gln Gln Val Leu Ile Gly Pro Tyr Val Leu Ile Gly Pro
        275                 280                 285

Gly Ser Ser Ala Ala Ala Ala Ala Ala Gly Ser Tyr Gly Tyr Gly
        290                 295                 300

Pro Gly Gln Gln Gly Pro Tyr Gly Pro Gly Ala Ser Gly Gln Asn Gly
305                 310                 315                 320

Pro Gly Ser Gly Gln Tyr Gly Pro Gly Gln Gly Pro Gly Pro Ser
                325                 330                 335

Ala Ala Ala Ala Ala Ala Gly Pro Gly Gln Gln Val Leu Ile Gly
                340                 345                 350

Pro Tyr Val Leu Ile Gly Pro Gly Ala Ser Ala Ala Ala Ala Ala
        355                 360                 365

Ala Gly Ser Tyr Gly Pro Gly Gln Gln Gly Pro Gly Gln Tyr Gly Pro
        370                 375                 380

Gly Ser Ser Gly Pro Gly Gln Gln Gly Pro Tyr Gly Pro Gly Ser Ser
385                 390                 395                 400

Ala Ala Ala Ala Ala Ala Ala Gly Ser Tyr Gly Pro Gly Gln Gln Val
                405                 410                 415

Leu Ile Gly Pro Tyr Val Leu Ile Gly Pro Gly Pro Ser Ala Ala Ala
        420                 425                 430

Ala Ala Ala Ala Gly Ser Tyr Gln Gln Gly Pro Gly Gln Gln Gly Pro
        435                 440                 445

Tyr Gly Pro Gly Ala Ser Gly Pro Gly Gln Gln Gly Pro Tyr Gly Pro
450                 455                 460

Gly Ala Ser Ala Ala Ala Ala Ala Ala Gly Pro Gly Gln Tyr Val
465                 470                 475                 480

Leu Ile Gly Pro Gly Gln Val Leu Ile Gly Pro Ser Ala Ser Ala
                485                 490                 495

Ala Ala Ala Ala Ala Gly Ser Tyr Gly Ser Gly Pro Gly Gln Tyr
        500                 505                 510

Gly Pro Tyr Gly Pro Gly Gln Ser Gly Pro Gly Ser Gly Gln Gln Gly
        515                 520                 525

Gln Gly Pro Tyr Gly Pro Gly Ala Ser Ala Ala Ala Ala Ala Ala
        530                 535                 540

Gly Ser Tyr Gly Pro Gly Gln Gln Val Leu Ile Gly Pro Tyr Val Leu
545                 550                 555                 560

Ile Gly Pro Gly Pro Ser Ala Ala Ala Ala Ala Ala Gly Pro Gly
                565                 570                 575

Ser Gly Gln Tyr Gly Pro Gly Ala Gly Gln Asn Gly Pro Gly Ser
                580                 585                 590

Gly Gln Tyr Gly Pro Gly Gln Gln Gly Pro Gly Pro Ser Ala Ala Ala
        595                 600                 605

Ala Ala Ala Ala Gly Pro Gly Ser Gly Gln Gln Val Leu Ile Gly Pro
```

Gly Ala Ser Val Leu Ile
625                 630

<210> SEQ ID NO 27
<211> LENGTH: 593
<212> TYPE: PRT
<213> ORGANISM: Artificial Sequence
<220> FEATURE:
<223> OTHER INFORMATION: M_PRT888

<400> SEQUENCE: 27

Met Gly Ser Ser Gly Pro Gly Val Leu Gly Pro Tyr Gly Pro Gly Ala
1               5                   10                  15

Ser Ala Ala Ala Ala Gly Gln Asn Gly Pro Gly Ser Gly Val Leu
            20                  25                  30

Gly Pro Gly Gln Ser Gly Gln Tyr Gly Pro Gly Val Leu Gly Pro Gly
            35                  40                  45

Val Leu Gly Pro Gly Ser Ser Ala Ala Ala Ala Gly Pro Gly Gln
50                  55                  60

Tyr Gly Pro Gly Val Leu Gly Pro Ser Ala Ser Ala Ala Ala Ala
65                  70                  75                  80

Gly Pro Gly Ser Gly Val Leu Gly Pro Gly Ala Ser Gly Gln Tyr Gly
                85                  90                  95

Pro Gly Val Leu Gly Pro Gly Val Leu Gly Pro Gly Ser Ser Ala Ala
                100                 105                 110

Ala Ala Ala Gly Gln Tyr Gly Ser Gly Pro Gly Val Leu Gly Pro Tyr
            115                 120                 125

Gly Ser Ala Ala Ala Ala Gly Pro Gly Ser Gly Gln Tyr Gly Gln
            130                 135                 140

Gly Pro Tyr Gly Pro Gly Ala Ser Gly Pro Gly Gln Tyr Gly Pro Gly
145                 150                 155                 160

Val Leu Gly Pro Ser Ala Ser Ala Ala Ala Ala Gly Ser Gly Val
                165                 170                 175

Leu Gly Pro Gly Gln Tyr Gly Pro Tyr Ala Ser Ala Ala Ala Ala
            180                 185                 190

Gly Gln Tyr Gly Ser Gly Pro Gly Val Leu Gly Pro Tyr Gly Pro Gly
        195                 200                 205

Gln Ser Gly Ser Gly Val Leu Gly Pro Gly Val Leu Gly Pro Tyr Ala
        210                 215                 220

Ser Ala Ala Ala Ala Gly Pro Gly Val Leu Gly Pro Tyr Gly Pro
225                 230                 235                 240

Gly Ser Ser Ala Ala Ala Ala Gly Gln Tyr Gly Tyr Gly Pro Gly
            245                 250                 255

Val Leu Gly Pro Tyr Gly Pro Gly Ala Ser Gly Gln Asn Gly Pro Gly
            260                 265                 270

Ser Gly Gln Tyr Gly Pro Gly Val Leu Gly Pro Gly Gln Ser Ala Ala
        275                 280                 285

Ala Ala Ala Gly Pro Gly Val Leu Gly Pro Tyr Gly Pro Gly Ala Ser
290                 295                 300

Ala Ala Ala Ala Gly Gln Tyr Gly Pro Gly Val Leu Gly Pro Gly
305                 310                 315                 320

Gln Tyr Gly Pro Gly Ser Ser Gly Pro Gly Val Leu Gly Pro Tyr Gly
            325                 330                 335

Pro Gly Ser Ser Ala Ala Ala Ala Ala Gly Gln Tyr Gly Pro Gly Val

```
                     340                 345                 350
Leu Gly Pro Tyr Gly Pro Gly Gln Ser Ala Ala Ala Ala Gly Gln
            355                 360                 365

Tyr Val Leu Gly Pro Gly Val Leu Gly Pro Tyr Gly Pro Gly Ala Ser
    370                 375                 380

Gly Pro Gly Val Leu Gly Pro Tyr Gly Pro Gly Ala Ser Ala Ala Ala
385                 390                 395                 400

Ala Ala Gly Pro Gly Gln Tyr Gly Pro Gly Val Leu Gly Pro Ser Ala
            405                 410                 415

Ser Ala Ala Ala Ala Gly Gln Tyr Gly Ser Gly Pro Gly Gln Tyr
        420                 425                 430

Gly Pro Tyr Gly Pro Gly Gln Ser Gly Pro Gly Ser Gly Val Leu Gly
            435                 440                 445

Gln Gly Pro Tyr Gly Pro Gly Ala Ser Ala Ala Ala Ala Gly Gln
        450                 455                 460

Tyr Gly Pro Gly Val Leu Gly Pro Tyr Gly Pro Gly Gln Ser Ala Ala
465                 470                 475                 480

Ala Ala Ala Gly Pro Gly Ser Gly Gln Tyr Gly Pro Gly Ala Ser Gly
            485                 490                 495

Gln Asn Gly Pro Gly Ser Gly Gln Tyr Gly Pro Gly Val Leu Gly Pro
        500                 505                 510

Gly Gln Ser Ala Ala Ala Ala Gly Gln Tyr Val Leu Gly Pro Gly
        515                 520                 525

Val Leu Gly Pro Tyr Gly Pro Gly Ala Ser Ala Ala Ala Ala Gly
        530                 535                 540

Gln Tyr Gly Ser Gly Pro Gly Val Leu Gly Pro Tyr Gly Pro Gly Gln
545                 550                 555                 560

Ser Gly Ser Gly Val Leu Gly Pro Val Leu Gly Pro Tyr Ala Ser
            565                 570                 575

Ala Ala Ala Ala Gly Pro Gly Ser Gly Val Leu Gly Pro Gly Ala
        580                 585                 590

Ser
```

<210> SEQ ID NO 28
<211> LENGTH: 590
<212> TYPE: PRT
<213> ORGANISM: Artificial Sequence
<220> FEATURE:
<223> OTHER INFORMATION: M_PRT965

<400> SEQUENCE: 28

```
Met Gly Pro Gly Thr Ser Gly Pro Tyr Gly Pro Gly Ala Ser Ala Ala
1               5                   10                  15

Ala Ala Ala Gly Ala Asn Gly Pro Gly Ser Gly Thr Ser Gly Pro Gly
            20                  25                  30

Ala Ser Gly Ala Tyr Gly Pro Gly Thr Ser Gly Pro Gly Thr Ser Gly
        35                  40                  45

Pro Gly Ser Ser Ala Ala Ala Ala Gly Pro Gly Ala Tyr Gly Pro
    50                  55                  60

Gly Thr Ser Gly Pro Ser Ala Ser Ala Ala Ala Ala Gly Pro Gly
65                  70                  75                  80

Ser Gly Thr Ser Gly Pro Gly Ala Ser Gly Ala Tyr Gly Pro Gly Thr
            85                  90                  95

Ser Gly Pro Gly Thr Ser Gly Pro Gly Ser Ser Ala Ala Ala Ala Ala
        100                 105                 110
```

```
Gly Ala Tyr Gly Ser Gly Pro Gly Thr Ser Gly Pro Tyr Gly Ser Ala
            115                 120                 125
Ala Ala Ala Ala Gly Pro Gly Ser Gly Ala Tyr Gly Ala Gly Pro Tyr
130                 135                 140
Gly Pro Gly Ala Ser Gly Pro Gly Ala Tyr Gly Pro Gly Thr Ser Gly
145                 150                 155                 160
Pro Ser Ala Ser Ala Ala Ala Ala Gly Ser Gly Thr Ser Gly Pro
                165                 170                 175
Gly Ala Tyr Gly Pro Tyr Ala Ser Ala Ala Ala Ala Gly Ala Tyr
            180                 185                 190
Gly Ser Gly Pro Gly Thr Ser Gly Pro Tyr Gly Pro Gly Ala Ser Gly
            195                 200                 205
Ser Gly Thr Ser Gly Pro Gly Thr Ser Gly Pro Tyr Ala Ser Ala Ala
            210                 215                 220
Ala Ala Ala Gly Pro Gly Thr Ser Gly Pro Tyr Gly Pro Gly Ser Ser
225                 230                 235                 240
Ala Ala Ala Ala Ala Gly Ala Tyr Gly Tyr Gly Pro Gly Thr Ser Gly
                245                 250                 255
Pro Tyr Gly Pro Gly Ala Ser Gly Ala Asn Gly Pro Gly Ser Gly Ala
            260                 265                 270
Tyr Gly Pro Gly Thr Ser Gly Pro Gly Ala Ser Ala Ala Ala Ala
            275                 280                 285
Gly Pro Gly Thr Ser Gly Pro Tyr Gly Pro Gly Ala Ser Ala Ala Ala
            290                 295                 300
Ala Ala Gly Ala Tyr Gly Pro Gly Thr Ser Gly Pro Gly Ala Tyr Gly
305                 310                 315                 320
Pro Gly Ser Ser Gly Pro Gly Thr Ser Gly Pro Tyr Gly Pro Gly Ser
            325                 330                 335
Ser Ala Ala Ala Ala Gly Ala Tyr Gly Pro Gly Thr Ser Gly Pro
            340                 345                 350
Tyr Gly Pro Gly Ala Ser Ala Ala Ala Ala Gly Ala Tyr Thr Ser
            355                 360                 365
Gly Pro Gly Thr Ser Gly Pro Tyr Gly Pro Gly Ala Ser Gly Pro Gly
            370                 375                 380
Thr Ser Gly Pro Tyr Gly Pro Gly Ala Ser Ala Ala Ala Ala Gly
385                 390                 395                 400
Pro Gly Ala Tyr Gly Pro Gly Thr Ser Gly Pro Ser Ala Ser Ala Ala
            405                 410                 415
Ala Ala Ala Gly Ala Tyr Gly Ser Gly Pro Gly Ala Tyr Gly Pro Tyr
            420                 425                 430
Gly Pro Gly Ala Ser Gly Pro Gly Ser Gly Thr Ser Gly Ala Gly Pro
            435                 440                 445
Tyr Gly Pro Gly Ala Ser Ala Ala Ala Ala Gly Ala Tyr Gly Pro
            450                 455                 460
Gly Thr Ser Gly Pro Tyr Gly Pro Gly Ala Ser Ala Ala Ala Ala
465                 470                 475                 480
Gly Pro Gly Ser Gly Ala Tyr Gly Pro Gly Ala Ser Gly Ala Asn Gly
                485                 490                 495
Pro Gly Ser Gly Ala Tyr Gly Pro Gly Thr Ser Gly Pro Gly Ala Ser
                500                 505                 510
Ala Ala Ala Ala Ala Gly Ala Tyr Thr Ser Gly Pro Gly Thr Ser Gly
                515                 520                 525
```

```
Pro Tyr Gly Pro Gly Ala Ser Ala Ala Ala Gly Ala Tyr Gly
        530                 535                 540

Ser Gly Pro Gly Thr Ser Gly Pro Tyr Gly Pro Gly Ala Ser Gly Ser
545                 550                 555                 560

Gly Thr Ser Gly Pro Gly Thr Ser Gly Pro Tyr Ala Ser Ala Ala Ala
                565                 570                 575

Ala Ala Gly Pro Gly Ser Gly Thr Ser Gly Pro Gly Ala Ser
            580                 585                 590

<210> SEQ ID NO 29
<211> LENGTH: 593
<212> TYPE: PRT
<213> ORGANISM: Artificial Sequence
<220> FEATURE:
<223> OTHER INFORMATION: M_PRT889

<400> SEQUENCE: 29

Met Gly Ser Ser Gly Pro Gly Val Leu Gly Pro Tyr Gly Pro Gly Ala
1               5                   10                  15

Ser Ala Ala Ala Ala Gly Ile Asn Gly Pro Gly Ser Gly Val Leu
            20                  25                  30

Gly Pro Gly Ile Ser Gly Ile Tyr Gly Pro Gly Val Leu Gly Pro Gly
        35                  40                  45

Val Leu Gly Pro Gly Ser Ser Ala Ala Ala Ala Gly Pro Gly Ile
50                  55                  60

Tyr Gly Pro Gly Val Leu Gly Pro Ser Ala Ser Ala Ala Ala Ala
65                  70                  75                  80

Gly Pro Gly Ser Gly Val Leu Gly Pro Gly Ala Ser Gly Ile Tyr Gly
                85                  90                  95

Pro Gly Val Leu Gly Pro Gly Val Leu Gly Pro Gly Ser Ser Ala Ala
            100                 105                 110

Ala Ala Ala Gly Ile Tyr Gly Ser Gly Pro Gly Val Leu Gly Pro Tyr
            115                 120                 125

Gly Ser Ala Ala Ala Ala Gly Pro Gly Ser Gly Ile Tyr Gly Ile
130                 135                 140

Gly Pro Tyr Gly Pro Gly Ala Ser Gly Pro Gly Ile Tyr Gly Pro Gly
145                 150                 155                 160

Val Leu Gly Pro Ser Ala Ser Ala Ala Ala Ala Gly Ser Gly Val
                165                 170                 175

Leu Gly Pro Gly Ile Tyr Gly Pro Tyr Ala Ser Ala Ala Ala Ala
            180                 185                 190

Gly Ile Tyr Gly Ser Gly Pro Gly Val Leu Gly Pro Tyr Gly Pro Gly
        195                 200                 205

Ile Ser Gly Ser Gly Val Leu Gly Pro Gly Val Leu Gly Pro Tyr Ala
210                 215                 220

Ser Ala Ala Ala Ala Gly Pro Gly Val Leu Gly Pro Tyr Gly Pro
225                 230                 235                 240

Gly Ser Ser Ala Ala Ala Ala Gly Ile Tyr Gly Tyr Gly Pro Gly
                245                 250                 255

Val Leu Gly Pro Tyr Gly Pro Gly Ala Ser Gly Ile Asn Gly Pro Gly
            260                 265                 270

Ser Gly Ile Tyr Gly Pro Gly Val Leu Gly Pro Gly Ile Ser Ala Ala
        275                 280                 285

Ala Ala Ala Gly Pro Gly Val Leu Gly Pro Tyr Gly Pro Gly Ala Ser
            290                 295                 300
```

```
Ala Ala Ala Ala Ala Gly Ile Tyr Gly Pro Gly Val Leu Gly Pro Gly
305                 310                 315                 320

Ile Tyr Gly Pro Gly Ser Ser Gly Pro Gly Val Leu Gly Pro Tyr Gly
                325                 330                 335

Pro Gly Ser Ser Ala Ala Ala Ala Gly Ile Tyr Gly Pro Gly Val
            340                 345                 350

Leu Gly Pro Tyr Gly Pro Gly Ile Ser Ala Ala Ala Ala Gly Ile
        355                 360                 365

Tyr Val Leu Gly Pro Gly Val Leu Gly Pro Tyr Gly Pro Gly Ala Ser
    370                 375                 380

Gly Pro Gly Val Leu Gly Pro Tyr Gly Pro Gly Ala Ser Ala Ala Ala
385                 390                 395                 400

Ala Ala Gly Pro Gly Ile Tyr Gly Pro Gly Val Leu Gly Pro Ser Ala
            405                 410                 415

Ser Ala Ala Ala Ala Gly Ile Tyr Gly Ser Gly Pro Gly Ile Tyr
            420                 425                 430

Gly Pro Tyr Gly Pro Gly Ile Ser Gly Pro Gly Ser Gly Val Leu Gly
        435                 440                 445

Ile Gly Pro Tyr Gly Pro Gly Ala Ser Ala Ala Ala Ala Gly Ile
450                 455                 460

Tyr Gly Pro Gly Val Leu Gly Pro Tyr Gly Pro Gly Ile Ser Ala Ala
465                 470                 475                 480

Ala Ala Ala Gly Pro Gly Ser Gly Ile Tyr Gly Pro Gly Ala Ser Gly
            485                 490                 495

Ile Asn Gly Pro Gly Ser Gly Ile Tyr Gly Pro Gly Val Leu Gly Pro
            500                 505                 510

Gly Ile Ser Ala Ala Ala Ala Gly Ile Tyr Val Leu Gly Pro Gly
        515                 520                 525

Val Leu Gly Pro Tyr Gly Pro Gly Ala Ser Ala Ala Ala Ala Gly
        530                 535                 540

Ile Tyr Gly Ser Gly Pro Gly Val Leu Gly Pro Tyr Gly Pro Gly Ile
545                 550                 555                 560

Ser Gly Ser Gly Val Leu Gly Pro Gly Val Leu Gly Pro Tyr Ala Ser
                565                 570                 575

Ala Ala Ala Ala Gly Pro Gly Ser Gly Val Leu Gly Pro Gly Ala
            580                 585                 590

Ser

<210> SEQ ID NO 30
<211> LENGTH: 590
<212> TYPE: PRT
<213> ORGANISM: Artificial Sequence
<220> FEATURE:
<223> OTHER INFORMATION: M_PRT916

<400> SEQUENCE: 30

Met Gly Pro Gly Val Ile Gly Pro Tyr Gly Pro Gly Ala Ser Ala Ala
1               5                   10                  15

Ala Ala Ala Gly Leu Asn Gly Pro Gly Ser Gly Val Ile Gly Pro Gly
            20                  25                  30

Leu Ser Gly Leu Tyr Gly Pro Gly Val Ile Gly Pro Gly Val Ile Gly
        35                  40                  45

Pro Gly Ser Ser Ala Ala Ala Ala Gly Pro Gly Leu Tyr Gly Pro
50                  55                  60

Gly Val Ile Gly Pro Ser Ala Ser Ala Ala Ala Ala Gly Pro Gly
```

```
            65                  70                  75                  80
        Ser Gly Val Ile Gly Pro Gly Ala Ser Gly Leu Tyr Gly Pro Gly Val
                        85                  90                  95

Ile Gly Pro Gly Val Ile Gly Pro Gly Ser Ala Ala Ala Ala
                        100                 105                 110

Gly Leu Tyr Gly Ser Gly Pro Gly Val Ile Gly Pro Tyr Gly Ser Ala
                        115                 120                 125

Ala Ala Ala Ala Gly Pro Gly Ser Gly Leu Tyr Gly Leu Gly Pro Tyr
                        130                 135                 140

Gly Pro Gly Ala Ser Gly Pro Gly Leu Tyr Gly Pro Gly Val Ile Gly
        145                 150                 155                 160

Pro Ser Ala Ser Ala Ala Ala Ala Gly Ser Gly Val Ile Gly Pro
                        165                 170                 175

Gly Leu Tyr Gly Pro Tyr Ala Ser Ala Ala Ala Ala Gly Leu Tyr
                        180                 185                 190

Gly Ser Gly Pro Gly Val Ile Gly Pro Tyr Gly Pro Gly Leu Ser Gly
                        195                 200                 205

Ser Gly Val Ile Gly Pro Gly Val Ile Gly Pro Tyr Ala Ser Ala Ala
                        210                 215                 220

Ala Ala Ala Gly Pro Gly Val Ile Gly Pro Gly Tyr Gly Pro Gly Ser Ser
        225                 230                 235                 240

Ala Ala Ala Ala Gly Leu Tyr Gly Tyr Gly Pro Gly Val Ile Gly
                        245                 250                 255

Pro Tyr Gly Pro Gly Ala Ser Gly Leu Asn Gly Pro Gly Ser Gly Leu
                        260                 265                 270

Tyr Gly Pro Gly Val Ile Gly Pro Gly Leu Ser Ala Ala Ala Ala
                        275                 280                 285

Gly Pro Gly Val Ile Gly Pro Tyr Gly Pro Gly Ala Ser Ala Ala Ala
                        290                 295                 300

Ala Ala Gly Leu Tyr Gly Pro Gly Val Ile Gly Pro Gly Leu Tyr Gly
        305                 310                 315                 320

Pro Gly Ser Ser Gly Pro Gly Val Ile Gly Pro Tyr Gly Pro Gly Ser
                        325                 330                 335

Ser Ala Ala Ala Ala Ala Gly Leu Tyr Gly Pro Gly Val Ile Gly Pro
                        340                 345                 350

Tyr Gly Pro Gly Leu Ser Ala Ala Ala Ala Gly Leu Tyr Val Ile
                        355                 360                 365

Gly Pro Gly Val Ile Gly Pro Tyr Gly Pro Gly Ala Ser Gly Pro Gly
                        370                 375                 380

Val Ile Gly Pro Tyr Gly Pro Gly Ala Ser Ala Ala Ala Ala Gly
        385                 390                 395                 400

Pro Gly Leu Tyr Gly Pro Gly Val Ile Gly Pro Ser Ala Ser Ala Ala
                        405                 410                 415

Ala Ala Ala Gly Leu Tyr Gly Ser Gly Pro Gly Leu Tyr Gly Pro Tyr
                        420                 425                 430

Gly Pro Gly Leu Ser Gly Pro Gly Ser Gly Val Ile Gly Leu Gly Pro
                        435                 440                 445

Tyr Gly Pro Gly Ala Ser Ala Ala Ala Ala Gly Leu Tyr Gly Pro
                        450                 455                 460

Gly Val Ile Gly Pro Tyr Gly Pro Gly Leu Ser Ala Ala Ala Ala
        465                 470                 475                 480

Gly Pro Gly Ser Gly Leu Tyr Gly Pro Gly Ala Ser Gly Leu Asn Gly
                        485                 490                 495
```

-continued

Pro Gly Ser Gly Leu Tyr Gly Pro Gly Val Ile Gly Pro Gly Leu Ser
                500                 505                 510

Ala Ala Ala Ala Ala Gly Leu Tyr Val Ile Gly Pro Gly Val Ile Gly
            515                 520                 525

Pro Tyr Gly Pro Gly Ala Ser Ala Ala Ala Ala Gly Leu Tyr Gly
        530                 535                 540

Ser Gly Pro Gly Val Ile Gly Pro Tyr Gly Pro Gly Leu Ser Gly Ser
545                 550                 555                 560

Gly Val Ile Gly Pro Gly Val Ile Gly Pro Tyr Ala Ser Ala Ala Ala
                565                 570                 575

Ala Ala Gly Pro Gly Ser Gly Val Ile Gly Pro Gly Ala Ser
            580                 585                 590

<210> SEQ ID NO 31
<211> LENGTH: 590
<212> TYPE: PRT
<213> ORGANISM: Artificial Sequence
<220> FEATURE:
<223> OTHER INFORMATION: M_ PRT918

<400> SEQUENCE: 31

Met Gly Pro Gly Val Phe Gly Pro Tyr Gly Pro Gly Ala Ser Ala Ala
1               5                   10                  15

Ala Ala Ala Gly Ile Asn Gly Pro Gly Ser Gly Val Phe Gly Pro Gly
            20                  25                  30

Ile Ser Gly Ile Tyr Gly Pro Gly Val Phe Gly Pro Gly Val Phe Gly
        35                  40                  45

Pro Gly Ser Ser Ala Ala Ala Ala Gly Pro Gly Ile Tyr Gly Pro
    50                  55                  60

Gly Val Phe Gly Pro Ser Ala Ser Ala Ala Ala Ala Gly Pro Gly
65                  70                  75                  80

Ser Gly Val Phe Gly Pro Gly Ala Ser Gly Ile Tyr Gly Pro Gly Val
                85                  90                  95

Phe Gly Pro Gly Val Phe Gly Pro Gly Ser Ser Ala Ala Ala Ala
                100                 105                 110

Gly Ile Tyr Gly Ser Gly Pro Gly Val Phe Gly Pro Tyr Gly Ser Ala
            115                 120                 125

Ala Ala Ala Gly Pro Gly Ser Gly Ile Tyr Gly Ile Gly Pro Tyr
        130                 135                 140

Gly Pro Gly Ala Ser Gly Pro Gly Ile Tyr Gly Pro Gly Val Phe Gly
145                 150                 155                 160

Pro Ser Ala Ser Ala Ala Ala Ala Gly Ser Gly Val Phe Gly Pro
            165                 170                 175

Gly Ile Tyr Gly Pro Tyr Ala Ser Ala Ala Ala Gly Ile Tyr
        180                 185                 190

Gly Ser Gly Pro Gly Val Phe Gly Pro Tyr Gly Pro Gly Ile Ser Gly
            195                 200                 205

Ser Gly Val Phe Gly Pro Gly Val Phe Gly Pro Tyr Ala Ser Ala Ala
    210                 215                 220

Ala Ala Ala Gly Pro Gly Val Phe Gly Pro Tyr Gly Pro Gly Ser Ser
225                 230                 235                 240

Ala Ala Ala Ala Ala Gly Ile Tyr Gly Tyr Gly Pro Gly Val Phe Gly
            245                 250                 255

Pro Tyr Gly Pro Gly Ala Ser Gly Ile Asn Gly Pro Gly Ser Gly Ile
        260                 265                 270

Tyr Gly Pro Gly Val Phe Gly Pro Gly Ile Ser Ala Ala Ala Ala
            275                 280                 285

Gly Pro Gly Val Phe Gly Pro Tyr Gly Pro Gly Ala Ser Ala Ala
            290                 295                 300

Ala Ala Gly Ile Tyr Gly Pro Gly Val Phe Gly Pro Gly Ile Tyr Gly
305                 310                 315                 320

Pro Gly Ser Ser Gly Pro Gly Val Phe Gly Pro Tyr Gly Pro Gly Ser
            325                 330                 335

Ser Ala Ala Ala Ala Gly Ile Tyr Gly Pro Gly Val Phe Gly Pro
            340                 345                 350

Tyr Gly Pro Gly Ile Ser Ala Ala Ala Ala Gly Ile Tyr Val Phe
            355                 360                 365

Gly Pro Gly Val Phe Gly Pro Tyr Gly Pro Gly Ala Ser Gly Pro Gly
            370                 375                 380

Val Phe Gly Pro Tyr Gly Pro Gly Ala Ser Ala Ala Ala Ala Gly
385                 390                 395                 400

Pro Gly Ile Tyr Gly Pro Gly Val Phe Gly Pro Ser Ala Ser Ala Ala
            405                 410                 415

Ala Ala Ala Gly Ile Tyr Gly Ser Gly Pro Gly Ile Tyr Gly Pro Tyr
            420                 425                 430

Gly Pro Gly Ile Ser Gly Pro Gly Ser Gly Val Phe Gly Ile Gly Pro
            435                 440                 445

Tyr Gly Pro Gly Ala Ser Ala Ala Ala Ala Gly Ile Tyr Gly Pro
            450                 455                 460

Gly Val Phe Gly Pro Tyr Gly Pro Gly Ile Ser Ala Ala Ala Ala
465                 470                 475                 480

Gly Pro Gly Ser Gly Ile Tyr Gly Pro Gly Ala Ser Gly Ile Asn Gly
            485                 490                 495

Pro Gly Ser Gly Ile Tyr Gly Pro Gly Val Phe Gly Pro Gly Ile Ser
            500                 505                 510

Ala Ala Ala Ala Gly Ile Tyr Val Phe Gly Pro Gly Val Phe Gly
            515                 520                 525

Pro Tyr Gly Pro Gly Ala Ser Ala Ala Ala Ala Gly Ile Tyr Gly
            530                 535                 540

Ser Gly Pro Gly Val Phe Gly Pro Tyr Gly Pro Gly Ile Ser Gly Ser
545                 550                 555                 560

Gly Val Phe Gly Pro Gly Val Phe Gly Pro Tyr Ala Ser Ala Ala
            565                 570                 575

Ala Ala Gly Pro Gly Ser Gly Val Phe Gly Pro Gly Ala Ser
            580                 585                 590

<210> SEQ ID NO 32
<211> LENGTH: 601
<212> TYPE: PRT
<213> ORGANISM: Artificial Sequence
<220> FEATURE:
<223> OTHER INFORMATION: PRT888

<400> SEQUENCE: 32

Met His His His His His Ser Ser Gly Ser Ser Gly Pro Gly Val
1               5                   10                  15

Leu Gly Pro Tyr Gly Pro Gly Ala Ser Ala Ala Ala Ala Gly Gln
            20                  25                  30

Asn Gly Pro Gly Ser Gly Val Leu Gly Pro Gly Gln Ser Gly Gln Tyr
            35                  40                  45

-continued

Gly Pro Gly Val Leu Gly Pro Gly Val Leu Gly Pro Gly Ser Ser Ala
 50                  55                  60

Ala Ala Ala Ala Gly Pro Gly Gln Tyr Gly Pro Gly Val Leu Gly Pro
65                  70                  75                  80

Ser Ala Ser Ala Ala Ala Ala Gly Pro Gly Ser Gly Val Leu Gly
                85                  90                  95

Pro Gly Ala Ser Gly Gln Tyr Gly Pro Gly Val Leu Gly Pro Gly Val
            100                 105                 110

Leu Gly Pro Gly Ser Ser Ala Ala Ala Ala Gly Gln Tyr Gly Ser
        115                 120                 125

Gly Pro Gly Val Leu Gly Pro Tyr Gly Ala Ala Ala Ala Gly
130                 135                 140

Pro Gly Ser Gly Gln Tyr Gly Gln Gly Pro Tyr Gly Pro Gly Ala Ser
145                 150                 155                 160

Gly Pro Gly Gln Tyr Gly Pro Gly Val Leu Gly Pro Ser Ala Ser Ala
                165                 170                 175

Ala Ala Ala Gly Ser Gly Val Leu Gly Pro Gly Gln Tyr Gly Pro
        180                 185                 190

Tyr Ala Ser Ala Ala Ala Ala Gly Gln Tyr Gly Ser Gly Pro Gly
        195                 200                 205

Val Leu Gly Pro Tyr Gly Pro Gly Gln Ser Gly Ser Gly Val Leu Gly
    210                 215                 220

Pro Gly Val Leu Gly Pro Tyr Ala Ser Ala Ala Ala Ala Gly Pro
225                 230                 235                 240

Gly Val Leu Gly Pro Tyr Gly Pro Gly Ser Ser Ala Ala Ala Ala
                245                 250                 255

Gly Gln Tyr Gly Tyr Gly Pro Gly Val Leu Gly Pro Tyr Gly Pro Gly
            260                 265                 270

Ala Ser Gly Gln Asn Gly Pro Gly Ser Gly Gln Tyr Gly Pro Gly Val
        275                 280                 285

Leu Gly Pro Gly Gln Ser Ala Ala Ala Ala Gly Pro Gly Val Leu
    290                 295                 300

Gly Pro Tyr Gly Pro Gly Ala Ser Ala Ala Ala Ala Gly Gln Tyr
305                 310                 315                 320

Gly Pro Gly Val Leu Gly Pro Gly Gln Tyr Gly Pro Gly Ser Ser Gly
                325                 330                 335

Pro Gly Val Leu Gly Pro Tyr Gly Pro Gly Ser Ser Ala Ala Ala
            340                 345                 350

Ala Gly Gln Tyr Gly Pro Gly Val Leu Gly Pro Tyr Gly Pro Gly Gln
        355                 360                 365

Ser Ala Ala Ala Ala Gly Gln Tyr Val Leu Gly Pro Gly Val Leu
    370                 375                 380

Gly Pro Tyr Gly Pro Gly Ala Ser Gly Pro Gly Val Leu Gly Pro Tyr
385                 390                 395                 400

Gly Pro Gly Ala Ser Ala Ala Ala Ala Gly Pro Gly Gln Tyr Gly
            405                 410                 415

Pro Gly Val Leu Gly Pro Ser Ala Ser Ala Ala Ala Ala Gly Gln
        420                 425                 430

Tyr Gly Ser Gly Pro Gly Gln Tyr Gly Pro Tyr Gly Pro Gly Gln Ser
    435                 440                 445

Gly Pro Gly Ser Gly Val Leu Gly Gln Gly Pro Tyr Gly Pro Gly Ala
450                 455                 460

Ser Ala Ala Ala Ala Gly Gln Tyr Gly Pro Gly Val Leu Gly Pro
465                 470                 475                 480

Tyr Gly Pro Gly Gln Ser Ala Ala Ala Ala Gly Pro Gly Ser Gly
            485                 490                 495

Gln Tyr Gly Pro Gly Ala Ser Gly Gln Asn Gly Pro Gly Ser Gly Gln
            500                 505                 510

Tyr Gly Pro Gly Val Leu Gly Pro Gly Gln Ser Ala Ala Ala Ala
            515                 520                 525

Gly Gln Tyr Val Leu Gly Pro Gly Val Leu Gly Pro Tyr Gly Pro Gly
            530                 535                 540

Ala Ser Ala Ala Ala Ala Gly Gln Tyr Gly Ser Gly Pro Gly Val
545                 550                 555                 560

Leu Gly Pro Tyr Gly Pro Gly Gln Ser Gly Ser Gly Val Leu Gly Pro
            565                 570                 575

Gly Val Leu Gly Pro Tyr Ala Ser Ala Ala Ala Ala Gly Pro Gly
            580                 585                 590

Ser Gly Val Leu Gly Pro Gly Ala Ser
        595                 600

<210> SEQ ID NO 33
<211> LENGTH: 601
<212> TYPE: PRT
<213> ORGANISM: Artificial Sequence
<220> FEATURE:
<223> OTHER INFORMATION: PRT965

<400> SEQUENCE: 33

Met His His His His His Ser Ser Gly Ser Ser Gly Pro Gly Thr
1               5                   10                  15

Ser Gly Pro Tyr Gly Pro Gly Ala Ser Ala Ala Ala Ala Gly Ala
                20                  25                  30

Asn Gly Pro Gly Ser Gly Thr Ser Gly Pro Gly Ala Ser Gly Ala Tyr
                35                  40                  45

Gly Pro Gly Thr Ser Gly Pro Gly Thr Ser Gly Pro Gly Ser Ser Ala
            50                  55                  60

Ala Ala Ala Ala Gly Pro Gly Ala Tyr Gly Pro Gly Thr Ser Gly Pro
65                  70                  75                  80

Ser Ala Ser Ala Ala Ala Ala Gly Pro Gly Ser Gly Thr Ser Gly
                85                  90                  95

Pro Gly Ala Ser Gly Ala Tyr Gly Pro Gly Thr Ser Gly Pro Gly Thr
            100                 105                 110

Ser Gly Pro Gly Ser Ser Ala Ala Ala Ala Gly Ala Tyr Gly Ser
            115                 120                 125

Gly Pro Gly Thr Ser Gly Pro Tyr Gly Ser Ala Ala Ala Ala Gly
            130                 135                 140

Pro Gly Ser Gly Ala Tyr Gly Ala Gly Pro Tyr Gly Pro Gly Ala Ser
145                 150                 155                 160

Gly Pro Gly Ala Tyr Gly Pro Gly Thr Ser Gly Pro Ser Ala Ser Ala
            165                 170                 175

Ala Ala Ala Gly Ser Gly Thr Ser Gly Pro Gly Ala Tyr Gly Pro
            180                 185                 190

Tyr Ala Ser Ala Ala Ala Ala Gly Ala Tyr Gly Ser Gly Pro Gly
            195                 200                 205

Thr Ser Gly Pro Tyr Gly Pro Gly Ala Ser Gly Ser Gly Thr Ser Gly
            210                 215                 220

```
Pro Gly Thr Ser Gly Pro Tyr Ala Ser Ala Ala Ala Gly Pro
225                 230                 235                 240

Gly Thr Ser Gly Pro Tyr Gly Pro Gly Ser Ser Ala Ala Ala Ala
                245                 250                 255

Gly Ala Tyr Gly Tyr Gly Pro Gly Thr Ser Gly Pro Tyr Gly Pro Gly
            260                 265                 270

Ala Ser Gly Ala Asn Gly Pro Gly Ser Gly Ala Tyr Gly Pro Gly Thr
        275                 280                 285

Ser Gly Pro Gly Ala Ser Ala Ala Ala Ala Gly Pro Gly Thr Ser
290                 295                 300

Gly Pro Tyr Gly Pro Gly Ala Ser Ala Ala Ala Ala Gly Ala Tyr
305                 310                 315                 320

Gly Pro Gly Thr Ser Gly Pro Gly Ala Tyr Gly Pro Gly Ser Ser Gly
                325                 330                 335

Pro Gly Thr Ser Gly Pro Tyr Gly Pro Gly Ser Ser Ala Ala Ala Ala
            340                 345                 350

Ala Gly Ala Tyr Gly Pro Gly Thr Ser Gly Pro Tyr Gly Pro Gly Ala
        355                 360                 365

Ser Ala Ala Ala Ala Gly Ala Tyr Thr Ser Gly Pro Gly Thr Ser
370                 375                 380

Gly Pro Tyr Gly Pro Gly Ala Ser Gly Pro Gly Thr Ser Gly Pro Tyr
385                 390                 395                 400

Gly Pro Gly Ala Ser Ala Ala Ala Ala Gly Pro Gly Ala Tyr Gly
                405                 410                 415

Pro Gly Thr Ser Gly Pro Ser Ser Ala Ala Ala Ala Gly Ala
            420                 425                 430

Tyr Gly Ser Gly Pro Gly Ala Tyr Gly Pro Tyr Gly Pro Gly Ala Ser
        435                 440                 445

Gly Pro Gly Ser Gly Thr Ser Gly Ala Gly Pro Tyr Gly Pro Gly Ala
450                 455                 460

Ser Ala Ala Ala Ala Gly Ala Tyr Gly Pro Gly Thr Ser Gly Pro
465                 470                 475                 480

Tyr Gly Pro Gly Ala Ser Ala Ala Ala Ala Gly Pro Gly Ser Gly
                485                 490                 495

Ala Tyr Gly Pro Gly Ala Ser Gly Ala Asn Gly Pro Gly Ser Gly Ala
            500                 505                 510

Tyr Gly Pro Gly Thr Ser Gly Pro Gly Ala Ser Ala Ala Ala Ala
        515                 520                 525

Gly Ala Tyr Thr Ser Gly Pro Gly Thr Ser Gly Pro Tyr Gly Pro Gly
530                 535                 540

Ala Ser Ala Ala Ala Ala Gly Ala Tyr Gly Ser Gly Pro Gly Thr
545                 550                 555                 560

Ser Gly Pro Tyr Gly Pro Gly Ala Ser Gly Ser Gly Thr Ser Gly Pro
                565                 570                 575

Gly Thr Ser Gly Pro Tyr Ala Ser Ala Ala Ala Ala Gly Pro Gly
            580                 585                 590

Ser Gly Thr Ser Gly Pro Gly Ala Ser
        595                 600

<210> SEQ ID NO 34
<211> LENGTH: 601
<212> TYPE: PRT
<213> ORGANISM: Artificial Sequence
<220> FEATURE:
<223> OTHER INFORMATION: PRT889
```

<400> SEQUENCE: 34

```
Met His His His His His Ser Ser Gly Ser Ser Gly Pro Gly Val
1               5                   10                  15

Leu Gly Pro Tyr Gly Pro Gly Ala Ser Ala Ala Ala Ala Gly Ile
                20                  25                  30

Asn Gly Pro Gly Ser Gly Val Leu Gly Pro Gly Ile Ser Gly Ile Tyr
                35                  40                  45

Gly Pro Gly Val Leu Gly Pro Gly Val Leu Gly Pro Gly Ser Ser Ala
            50                  55                  60

Ala Ala Ala Ala Gly Pro Gly Ile Tyr Gly Pro Gly Val Leu Gly Pro
65                  70                  75                  80

Ser Ala Ser Ala Ala Ala Ala Gly Pro Gly Ser Gly Val Leu Gly
                85                  90                  95

Pro Gly Ala Ser Gly Ile Tyr Gly Pro Gly Val Leu Gly Pro Gly Val
                100                 105                 110

Leu Gly Pro Gly Ser Ser Ala Ala Ala Ala Gly Ile Tyr Gly Ser
                115                 120                 125

Gly Pro Gly Val Leu Gly Pro Tyr Gly Ser Ala Ala Ala Ala Gly
            130                 135                 140

Pro Gly Ser Gly Ile Tyr Gly Ile Gly Pro Tyr Gly Pro Gly Ala Ser
145                 150                 155                 160

Gly Pro Gly Ile Tyr Gly Pro Gly Val Leu Gly Pro Ser Ala Ser Ala
                165                 170                 175

Ala Ala Ala Ala Gly Ser Gly Val Leu Gly Pro Gly Ile Tyr Gly Pro
            180                 185                 190

Tyr Ala Ser Ala Ala Ala Ala Gly Ile Tyr Gly Ser Gly Pro Gly
                195                 200                 205

Val Leu Gly Pro Tyr Gly Pro Gly Ile Ser Gly Ser Gly Val Leu Gly
                210                 215                 220

Pro Gly Val Leu Gly Pro Tyr Ala Ser Ala Ala Ala Ala Gly Pro
225                 230                 235                 240

Gly Val Leu Gly Pro Tyr Gly Pro Gly Ser Ser Ala Ala Ala Ala
                245                 250                 255

Gly Ile Tyr Gly Tyr Gly Pro Gly Val Leu Gly Pro Tyr Gly Pro Gly
                260                 265                 270

Ala Ser Gly Ile Asn Gly Pro Gly Ser Gly Ile Tyr Gly Pro Gly Val
                275                 280                 285

Leu Gly Pro Gly Ile Ser Ala Ala Ala Ala Gly Pro Gly Val Leu
                290                 295                 300

Gly Pro Tyr Gly Pro Gly Ala Ser Ala Ala Ala Ala Gly Ile Tyr
305                 310                 315                 320

Gly Pro Gly Val Leu Gly Pro Gly Ile Tyr Gly Pro Gly Ser Ser Gly
                325                 330                 335

Pro Gly Val Leu Gly Pro Tyr Gly Pro Gly Ser Ser Ala Ala Ala Ala
                340                 345                 350

Ala Gly Ile Tyr Gly Pro Gly Val Leu Gly Pro Tyr Gly Pro Gly Ile
                355                 360                 365

Ser Ala Ala Ala Ala Gly Ile Tyr Val Leu Gly Pro Gly Val Leu
                370                 375                 380

Gly Pro Tyr Gly Pro Gly Ala Ser Gly Pro Gly Val Leu Gly Pro Tyr
385                 390                 395                 400

Gly Pro Gly Ala Ser Ala Ala Ala Ala Gly Pro Gly Ile Tyr Gly
```

```
                        405                 410                 415

Pro Gly Val Leu Gly Pro Ser Ala Ser Ala Ala Ala Ala Gly Ile
            420                 425                 430

Tyr Gly Ser Gly Pro Gly Ile Tyr Gly Pro Tyr Gly Pro Gly Ile Ser
            435                 440                 445

Gly Pro Gly Ser Gly Val Leu Gly Ile Gly Pro Tyr Gly Pro Gly Ala
        450                 455                 460

Ser Ala Ala Ala Ala Gly Ile Tyr Gly Pro Gly Val Leu Gly Pro
465                 470                 475                 480

Tyr Gly Pro Gly Ile Ser Ala Ala Ala Ala Gly Pro Gly Ser Gly
                485                 490                 495

Ile Tyr Gly Pro Gly Ala Ser Gly Ile Asn Gly Pro Gly Ser Gly Ile
                500                 505                 510

Tyr Gly Pro Gly Val Leu Gly Pro Gly Ile Ser Ala Ala Ala Ala
            515                 520                 525

Gly Ile Tyr Val Leu Gly Pro Gly Val Leu Pro Tyr Gly Pro Gly
        530                 535                 540

Ala Ser Ala Ala Ala Ala Gly Ile Tyr Gly Ser Gly Pro Gly Val
545                 550                 555                 560

Leu Gly Pro Tyr Gly Pro Gly Ile Ser Gly Ser Val Leu Gly Pro
                565                 570                 575

Gly Val Leu Gly Pro Tyr Ala Ser Ala Ala Ala Ala Gly Pro Gly
            580                 585                 590

Ser Gly Val Leu Gly Pro Gly Ala Ser
        595                 600

<210> SEQ ID NO 35
<211> LENGTH: 601
<212> TYPE: PRT
<213> ORGANISM: Artificial Sequence
<220> FEATURE:
<223> OTHER INFORMATION: PRT916

<400> SEQUENCE: 35

Met His His His His His Ser Ser Gly Ser Ser Gly Pro Gly Val
1               5                   10                  15

Ile Gly Pro Tyr Gly Pro Gly Ala Ser Ala Ala Ala Ala Gly Leu
            20                  25                  30

Asn Gly Pro Gly Ser Gly Val Ile Gly Pro Gly Leu Ser Gly Leu Tyr
        35                  40                  45

Gly Pro Gly Val Ile Gly Pro Gly Val Ile Gly Pro Gly Ser Ser Ala
    50                  55                  60

Ala Ala Ala Ala Gly Pro Gly Leu Tyr Gly Pro Gly Val Ile Gly Pro
65                  70                  75                  80

Ser Ala Ser Ala Ala Ala Ala Gly Pro Gly Ser Gly Val Ile Gly
                85                  90                  95

Pro Gly Ala Ser Gly Leu Tyr Gly Pro Gly Val Ile Gly Pro Gly Val
            100                 105                 110

Ile Gly Pro Gly Ser Ser Ala Ala Ala Ala Gly Leu Tyr Gly Ser
            115                 120                 125

Gly Pro Gly Val Ile Gly Pro Tyr Gly Ser Ala Ala Ala Ala Gly
        130                 135                 140

Pro Gly Ser Gly Leu Tyr Gly Leu Gly Pro Tyr Gly Pro Gly Ala Ser
145                 150                 155                 160

Gly Pro Gly Leu Tyr Gly Pro Gly Val Ile Gly Pro Ser Ala Ser Ala
```

-continued

```
                165                 170                 175
Ala Ala Ala Ala Gly Ser Gly Val Ile Gly Pro Gly Leu Tyr Gly Pro
                180                 185                 190
Tyr Ala Ser Ala Ala Ala Ala Gly Leu Tyr Gly Ser Gly Pro Gly
            195                 200                 205
Val Ile Gly Pro Tyr Gly Pro Gly Leu Ser Gly Ser Gly Val Ile Gly
            210                 215                 220
Pro Gly Val Ile Gly Pro Tyr Ala Ser Ala Ala Ala Ala Gly Pro
225                 230                 235                 240
Gly Val Ile Gly Pro Tyr Gly Pro Gly Ser Ser Ala Ala Ala Ala
                245                 250                 255
Gly Leu Tyr Gly Tyr Gly Pro Gly Val Ile Gly Pro Tyr Gly Pro Gly
            260                 265                 270
Ala Ser Gly Leu Asn Gly Pro Gly Ser Gly Leu Tyr Gly Pro Gly Val
            275                 280                 285
Ile Gly Pro Gly Leu Ser Ala Ala Ala Ala Gly Pro Gly Val Ile
            290                 295                 300
Gly Pro Tyr Gly Pro Gly Ala Ser Ala Ala Ala Ala Gly Leu Tyr
305                 310                 315                 320
Gly Pro Gly Val Ile Gly Pro Gly Leu Tyr Gly Pro Gly Ser Ser Gly
                325                 330                 335
Pro Gly Val Ile Gly Pro Tyr Gly Pro Gly Ser Ser Ala Ala Ala
                340                 345                 350
Ala Gly Leu Tyr Gly Pro Gly Val Ile Gly Pro Tyr Gly Pro Gly Leu
            355                 360                 365
Ser Ala Ala Ala Ala Gly Leu Tyr Val Ile Gly Pro Gly Val Ile
            370                 375                 380
Gly Pro Tyr Gly Pro Gly Ala Ser Gly Pro Gly Val Ile Gly Pro Tyr
385                 390                 395                 400
Gly Pro Gly Ala Ser Ala Ala Ala Ala Gly Pro Gly Leu Tyr Gly
                405                 410                 415
Pro Gly Val Ile Gly Pro Ser Ala Ser Ala Ala Ala Ala Gly Leu
                420                 425                 430
Tyr Gly Ser Gly Pro Gly Leu Tyr Gly Pro Tyr Gly Pro Gly Leu Ser
            435                 440                 445
Gly Pro Gly Ser Gly Val Ile Gly Leu Gly Pro Tyr Gly Pro Gly Ala
            450                 455                 460
Ser Ala Ala Ala Ala Gly Leu Tyr Gly Pro Gly Val Ile Gly Pro
465                 470                 475                 480
Tyr Gly Pro Gly Leu Ser Ala Ala Ala Ala Gly Pro Gly Ser Gly
            485                 490                 495
Leu Tyr Gly Gly Ala Ser Gly Leu Asn Gly Pro Gly Ser Gly Leu
            500                 505                 510
Tyr Gly Pro Gly Val Ile Gly Pro Gly Leu Ser Ala Ala Ala Ala
            515                 520                 525
Gly Leu Tyr Val Ile Gly Pro Gly Val Ile Gly Pro Tyr Gly Pro Gly
            530                 535                 540
Ala Ser Ala Ala Ala Ala Gly Leu Tyr Gly Ser Gly Pro Gly Val
545                 550                 555                 560
Ile Gly Pro Tyr Gly Pro Gly Leu Ser Gly Ser Gly Val Ile Gly Pro
                565                 570                 575
Gly Val Ile Gly Pro Tyr Ala Ser Ala Ala Ala Ala Gly Pro Gly
                580                 585                 590
```

```
Ser Gly Val Ile Gly Pro Gly Ala Ser
        595                 600

<210> SEQ ID NO 36
<211> LENGTH: 601
<212> TYPE: PRT
<213> ORGANISM: Artificial Sequence
<220> FEATURE:
<223> OTHER INFORMATION: PRT918

<400> SEQUENCE: 36

Met His His His His His Ser Ser Gly Ser Gly Pro Gly Val
1               5                   10                  15

Phe Gly Pro Tyr Gly Pro Gly Ala Ser Ala Ala Ala Ala Gly Ile
            20                  25                  30

Asn Gly Pro Gly Ser Gly Val Phe Gly Pro Gly Ile Ser Gly Ile Tyr
        35                  40                  45

Gly Pro Gly Val Phe Gly Pro Gly Val Phe Gly Pro Gly Ser Ser Ala
    50                  55                  60

Ala Ala Ala Gly Pro Gly Ile Tyr Gly Pro Gly Val Phe Gly Pro
65                  70                  75                  80

Ser Ala Ser Ala Ala Ala Ala Gly Pro Gly Ser Gly Val Phe Gly
                85                  90                  95

Pro Gly Ala Ser Gly Ile Tyr Gly Pro Gly Val Phe Gly Pro Gly Val
            100                 105                 110

Phe Gly Pro Gly Ser Ser Ala Ala Ala Ala Gly Ile Tyr Gly Ser
            115                 120                 125

Gly Pro Gly Val Phe Gly Pro Tyr Gly Ser Ala Ala Ala Ala Gly
    130                 135                 140

Pro Gly Ser Gly Ile Tyr Gly Ile Gly Pro Tyr Gly Pro Gly Ala Ser
145                 150                 155                 160

Gly Pro Gly Ile Tyr Gly Pro Gly Val Phe Gly Pro Ser Ala Ser Ala
                165                 170                 175

Ala Ala Ala Gly Ser Gly Val Phe Gly Pro Gly Ile Tyr Gly Pro
            180                 185                 190

Tyr Ala Ser Ala Ala Ala Ala Gly Ile Tyr Gly Ser Gly Pro Gly
        195                 200                 205

Val Phe Gly Pro Tyr Gly Pro Gly Ile Ser Gly Ser Gly Val Phe Gly
        210                 215                 220

Pro Gly Val Phe Gly Pro Tyr Ala Ser Ala Ala Ala Ala Gly Pro
225                 230                 235                 240

Gly Val Phe Gly Pro Tyr Gly Pro Gly Ser Ser Ala Ala Ala Ala
                245                 250                 255

Gly Ile Tyr Gly Tyr Gly Pro Gly Val Phe Gly Pro Tyr Gly Pro Gly
            260                 265                 270

Ala Ser Gly Ile Asn Gly Pro Gly Ser Gly Ile Tyr Gly Pro Gly Val
        275                 280                 285

Phe Gly Pro Gly Ile Ser Ala Ala Ala Ala Gly Pro Gly Val Phe
            290                 295                 300

Gly Pro Tyr Gly Pro Gly Ala Ser Ala Ala Ala Ala Gly Ile Tyr
305                 310                 315                 320

Gly Pro Gly Val Phe Gly Pro Gly Ile Tyr Gly Pro Gly Ser Ser Gly
                325                 330                 335

Pro Gly Val Phe Gly Pro Tyr Gly Pro Gly Ser Ser Ala Ala Ala Ala
            340                 345                 350
```

-continued

```
Ala Gly Ile Tyr Gly Pro Gly Val Phe Gly Pro Tyr Gly Pro Gly Ile
        355                 360                 365

Ser Ala Ala Ala Ala Gly Ile Tyr Val Phe Gly Pro Gly Val Phe
    370                 375                 380

Gly Pro Tyr Gly Pro Gly Ala Ser Gly Pro Gly Val Phe Gly Pro Tyr
385                 390                 395                 400

Gly Pro Gly Ala Ser Ala Ala Ala Ala Gly Pro Gly Ile Tyr Gly
                405                 410                 415

Pro Gly Val Phe Gly Pro Ser Ala Ser Ala Ala Ala Ala Gly Ile
            420                 425                 430

Tyr Gly Ser Gly Pro Gly Ile Tyr Gly Pro Tyr Gly Pro Gly Ile Ser
        435                 440                 445

Gly Pro Gly Ser Gly Val Phe Gly Ile Gly Pro Tyr Gly Pro Gly Ala
    450                 455                 460

Ser Ala Ala Ala Ala Gly Ile Tyr Gly Pro Gly Val Phe Gly Pro
465                 470                 475                 480

Tyr Gly Pro Gly Ile Ser Ala Ala Ala Ala Gly Pro Gly Ser Gly
                485                 490                 495

Ile Tyr Gly Pro Gly Ala Ser Gly Ile Asn Gly Pro Gly Ser Gly Ile
        500                 505                 510

Tyr Gly Pro Gly Val Phe Gly Pro Gly Ile Ser Ala Ala Ala Ala
    515                 520                 525

Gly Ile Tyr Val Phe Gly Pro Gly Val Phe Gly Pro Tyr Gly Pro Gly
    530                 535                 540

Ala Ser Ala Ala Ala Ala Gly Ile Tyr Gly Ser Gly Pro Gly Val
545                 550                 555                 560

Phe Gly Pro Tyr Gly Pro Gly Ile Ser Gly Ser Gly Val Phe Gly Pro
                565                 570                 575

Gly Val Phe Gly Pro Tyr Ala Ser Ala Ala Ala Ala Gly Pro Gly
            580                 585                 590

Ser Gly Val Phe Gly Pro Gly Ala Ser
    595                 600
```

<210> SEQ ID NO 37
<211> LENGTH: 565
<212> TYPE: PRT
<213> ORGANISM: Artificial Sequence
<220> FEATURE:
<223> OTHER INFORMATION: M_PRT525

<400> SEQUENCE: 37

```
Met Gly Pro Gly Gln Gln Gly Pro Tyr Gly Pro Gly Ala Ser Ala Ala
1               5                   10                  15

Ala Ala Ala Ala Ala Gly Ser Asn Gly Pro Gly Ser Gly Gln Gln Gly
                20                  25                  30

Pro Gly Gln Ser Gly Gln Tyr Gly Pro Gly Gln Gln Gly Pro Gly Gln
        35                  40                  45

Gln Gly Pro Gly Ser Ser Ala Ala Ala Ala Ala Ala Gly Pro Gly Gly
    50                  55                  60

Gln Tyr Gly Pro Gly Gln Gln Gly Pro Ser Ala Ser Ala Ala Ala Ala
65                  70                  75                  80

Ala Ala Ala Gly Pro Gly Ser Gly Gln Gln Gly Pro Gly Ala Ser Gly
                85                  90                  95

Gln Tyr Gly Pro Gly Gln Gln Gly Pro Gly Gln Gln Gly Pro Gly Ser
            100                 105                 110
```

```
Ser Ala Ala Ala Ala Ala Ala Gly Ser Tyr Gly Ser Gly Pro Gly
    115                 120                 125

Gln Gln Gly Pro Tyr Gly Ser Ala Ala Ala Ala Ala Ala Gly Pro
    130                 135                 140

Gly Ser Gly Gln Tyr Gly Gln Gly Pro Tyr Gly Pro Gly Ala Ser Gly
145                 150                 155                 160

Pro Gly Gln Tyr Gly Pro Gly Gln Gln Gly Pro Ser Ala Ser Ala Ala
                165                 170                 175

Ala Ala Ala Ala Ala Gly Ser Gly Gln Gln Gly Pro Gly Gln Tyr Gly
            180                 185                 190

Pro Tyr Ala Ser Ala Ala Ala Ala Ala Ala Gly Ser Tyr Gly Ser
        195                 200                 205

Gly Pro Gly Gln Gln Gly Pro Tyr Gly Pro Gly Gln Ser Gly Ser Gly
    210                 215                 220

Gln Gln Gly Pro Gly Gln Gln Gly Pro Tyr Ala Ser Ala Ala Ala Ala
225                 230                 235                 240

Ala Ala Ala Gly Pro Gly Gln Gln Pro Tyr Gly Pro Gly Ser Ser
            245                 250                 255

Ala Ala Ala Ala Ala Ala Ala Gly Ser Tyr Gly Tyr Gly Pro Gly Gln
            260                 265                 270

Gln Gly Pro Tyr Gly Pro Gly Ala Ser Gly Gln Asn Gly Pro Gly Ser
        275                 280                 285

Gly Gln Tyr Gly Pro Gly Gln Gln Gly Pro Gly Pro Ser Ala Ala Ala
    290                 295                 300

Ala Ala Ala Gly Pro Gly Gln Gln Gly Pro Tyr Gly Pro Gly Ala
305                 310                 315                 320

Ser Ala Ala Ala Ala Ala Ala Gly Ser Tyr Gly Pro Gly Gln Gln
        325                 330                 335

Gly Pro Gly Gln Tyr Gly Pro Gly Ser Ser Gly Pro Gly Gln Gln Gly
    340                 345                 350

Pro Tyr Gly Pro Gly Ser Ser Ala Ala Ala Ala Ala Ala Gly Ser
        355                 360                 365

Tyr Gly Pro Gly Gln Gln Gly Pro Tyr Gly Pro Gly Pro Ser Ala Ala
    370                 375                 380

Ala Ala Ala Ala Ala Gly Ser Tyr Gln Gln Gly Pro Gly Gln Gln Gly
385                 390                 395                 400

Pro Tyr Gly Pro Gly Ala Ser Gly Pro Gly Gln Gln Gly Pro Tyr Gly
                405                 410                 415

Pro Gly Ala Ser Ala Ala Ala Ala Ala Ala Gly Pro Gly Gln Tyr
            420                 425                 430

Gly Pro Gly Gln Gln Gly Pro Ser Ala Ser Ala Ala Ala Ala Ala
    435                 440                 445

Ala Gly Ser Tyr Gly Ser Gly Pro Gly Gln Tyr Gly Pro Tyr Gly Pro
    450                 455                 460

Gly Gln Ser Gly Pro Gly Ser Gly Gln Gln Gly Pro Gly Pro Tyr Gly
465                 470                 475                 480

Pro Gly Ala Ser Ala Ala Ala Ala Ala Ala Gly Ser Tyr Gly Pro
            485                 490                 495

Gly Gln Gln Gly Pro Tyr Gly Pro Gly Pro Ser Ala Ala Ala Ala Ala
        500                 505                 510

Ala Ala Gly Pro Gly Ser Gly Gln Tyr Gly Pro Gly Ala Ser Gly Gln
        515                 520                 525
```

Asn Gly Pro Gly Ser Gly Gln Tyr Gly Pro Gly Gln Gly Pro Gly
            530                 535                 540

Pro Ser Ala Ala Ala Ala Ala Ala Gly Pro Gly Ser Gly Gln Gln
545                 550                 555                 560

Gly Pro Gly Ala Ser
            565

<210> SEQ ID NO 38
<211> LENGTH: 565
<212> TYPE: PRT
<213> ORGANISM: Artificial Sequence
<220> FEATURE:
<223> OTHER INFORMATION: M_PRT699

<400> SEQUENCE: 38

Met Gly Pro Gly Val Leu Gly Pro Tyr Gly Pro Gly Ala Ser Ala Ala
1               5                   10                  15

Ala Ala Ala Ala Gly Ser Asn Gly Pro Gly Ser Gly Val Leu Gly
                20                  25                  30

Pro Gly Gln Ser Gly Gln Tyr Gly Pro Gly Val Leu Gly Pro Gly Val
            35                  40                  45

Leu Gly Pro Gly Ser Ser Ala Ala Ala Ala Ala Gly Pro Gly
50                  55                  60

Gln Tyr Gly Pro Gly Val Leu Gly Pro Ser Ala Ser Ala Ala Ala
65                  70                  75                  80

Ala Ala Ala Gly Pro Gly Ser Gly Val Leu Gly Pro Gly Ala Ser Gly
                85                  90                  95

Gln Tyr Gly Pro Gly Val Leu Gly Pro Gly Val Leu Gly Pro Gly Ser
            100                 105                 110

Ser Ala Ala Ala Ala Ala Ala Gly Ser Tyr Gly Ser Gly Pro Gly
            115                 120                 125

Val Leu Gly Pro Tyr Gly Ser Ala Ala Ala Ala Ala Gly Pro
130                 135                 140

Gly Ser Gly Gln Tyr Gly Gln Gly Pro Tyr Gly Pro Gly Ala Ser Gly
145                 150                 155                 160

Pro Gly Gln Tyr Gly Pro Gly Val Leu Gly Pro Ser Ala Ser Ala Ala
                165                 170                 175

Ala Ala Ala Ala Gly Ser Gly Val Leu Gly Pro Gly Gln Tyr Gly
            180                 185                 190

Pro Tyr Ala Ser Ala Ala Ala Ala Ala Gly Ser Tyr Gly Ser
            195                 200                 205

Gly Pro Gly Val Leu Gly Pro Tyr Gly Pro Gly Gln Ser Gly Ser Gly
210                 215                 220

Val Leu Gly Pro Gly Val Leu Gly Pro Tyr Ala Ser Ala Ala Ala Ala
225                 230                 235                 240

Ala Ala Ala Gly Pro Gly Val Leu Gly Pro Tyr Gly Pro Gly Ser Ser
                245                 250                 255

Ala Ala Ala Ala Ala Ala Gly Ser Tyr Gly Tyr Gly Pro Gly Val
            260                 265                 270

Leu Gly Pro Tyr Gly Pro Gly Ala Ser Gly Gln Asn Gly Pro Gly Ser
            275                 280                 285

Gly Gln Tyr Gly Pro Gly Val Leu Gly Pro Gly Ser Ala Ala Ala
            290                 295                 300

Ala Ala Ala Ala Gly Pro Gly Val Leu Gly Pro Tyr Gly Pro Gly Ala
305                 310                 315                 320

Ser Ala Ala Ala Ala Ala Gly Ser Tyr Gly Pro Gly Val Leu
            325                 330                 335

Gly Pro Gly Gln Tyr Gly Pro Gly Ser Ser Gly Pro Gly Val Leu Gly
            340                 345                 350

Pro Tyr Gly Pro Gly Ser Ser Ala Ala Ala Ala Ala Ala Gly Ser
            355                 360                 365

Tyr Gly Pro Gly Val Leu Gly Pro Tyr Gly Pro Gly Pro Ser Ala Ala
            370                 375                 380

Ala Ala Ala Ala Ala Gly Ser Tyr Val Leu Gly Pro Gly Val Leu Gly
385                 390                 395                 400

Pro Tyr Gly Pro Gly Ala Ser Gly Pro Gly Val Leu Gly Pro Tyr Gly
            405                 410                 415

Pro Gly Ala Ser Ala Ala Ala Ala Ala Ala Gly Pro Gly Gln Tyr
            420                 425                 430

Gly Pro Gly Val Leu Gly Pro Ser Ala Ser Ala Ala Ala Ala Ala
            435                 440                 445

Ala Gly Ser Tyr Gly Ser Gly Pro Gly Gln Tyr Gly Pro Tyr Gly Pro
            450                 455                 460

Gly Gln Ser Gly Pro Gly Ser Gly Val Leu Gly Gln Gly Pro Tyr Gly
465                 470                 475                 480

Pro Gly Ala Ser Ala Ala Ala Ala Ala Gly Ser Tyr Gly Pro
            485                 490                 495

Gly Val Leu Gly Pro Tyr Gly Pro Gly Pro Ser Ala Ala Ala Ala
            500                 505                 510

Ala Ala Gly Pro Gly Ser Gly Gln Tyr Gly Pro Gly Ala Ser Gly Gln
            515                 520                 525

Asn Gly Pro Gly Ser Gly Gln Tyr Gly Pro Gly Val Leu Gly Pro Gly
            530                 535                 540

Pro Ser Ala Ala Ala Ala Ala Ala Gly Pro Gly Ser Gly Val Leu
545                 550                 555                 560

Gly Pro Gly Ala Ser
            565

<210> SEQ ID NO 39
<211> LENGTH: 565
<212> TYPE: PRT
<213> ORGANISM: Artificial Sequence
<220> FEATURE:
<223> OTHER INFORMATION: M_PRT698

<400> SEQUENCE: 39

Met Gly Pro Gly Val Leu Gly Pro Tyr Gly Pro Gly Ala Ser Ala Ala
1               5                   10                  15

Ala Ala Ala Ala Ala Gly Ser Asn Gly Pro Gly Ser Gly Val Leu Gly
            20                  25                  30

Pro Gly Ile Ser Gly Ile Tyr Gly Pro Gly Val Leu Gly Pro Gly Val
            35                  40                  45

Leu Gly Pro Gly Ser Ser Ala Ala Ala Ala Ala Ala Gly Pro Gly
            50                  55                  60

Ile Tyr Gly Pro Gly Val Leu Gly Pro Ser Ala Ser Ala Ala Ala Ala
65                  70                  75                  80

Ala Ala Ala Gly Pro Gly Ser Gly Val Leu Gly Pro Gly Ala Ser Gly
            85                  90                  95

Ile Tyr Gly Pro Gly Val Leu Gly Pro Gly Val Leu Gly Pro Gly Ser
            100                 105                 110

```
Ser Ala Ala Ala Ala Ala Ala Gly Ser Tyr Gly Ser Gly Pro Gly
            115                 120                 125

Val Leu Gly Pro Tyr Gly Ser Ala Ala Ala Ala Ala Ala Gly Pro
    130                 135                 140

Gly Ser Gly Ile Tyr Gly Ile Gly Pro Tyr Gly Pro Gly Ala Ser Gly
145                 150                 155                 160

Pro Gly Ile Tyr Gly Pro Gly Val Leu Gly Pro Ser Ala Ser Ala Ala
                165                 170                 175

Ala Ala Ala Ala Ala Gly Ser Gly Val Leu Gly Pro Gly Ile Tyr Gly
            180                 185                 190

Pro Tyr Ala Ser Ala Ala Ala Ala Ala Gly Ser Tyr Gly Ser
            195                 200                 205

Gly Pro Gly Val Leu Gly Pro Tyr Gly Pro Gly Ile Ser Gly Ser Gly
    210                 215                 220

Val Leu Gly Pro Gly Val Leu Gly Pro Tyr Ala Ser Ala Ala Ala Ala
225                 230                 235                 240

Ala Ala Ala Gly Pro Gly Val Leu Gly Pro Tyr Gly Pro Gly Ser Ser
            245                 250                 255

Ala Ala Ala Ala Ala Ala Gly Ser Tyr Gly Tyr Gly Pro Gly Val
            260                 265                 270

Leu Gly Pro Tyr Gly Pro Gly Ala Ser Gly Ile Asn Gly Pro Gly Ser
    275                 280                 285

Gly Ile Tyr Gly Pro Gly Val Leu Gly Pro Gly Pro Ser Ala Ala Ala
    290                 295                 300

Ala Ala Ala Ala Gly Pro Gly Val Leu Gly Pro Tyr Gly Pro Gly Ala
305                 310                 315                 320

Ser Ala Ala Ala Ala Ala Ala Gly Ser Tyr Gly Pro Gly Val Leu
            325                 330                 335

Gly Pro Gly Ile Tyr Gly Pro Gly Ser Ser Gly Pro Gly Val Leu Gly
            340                 345                 350

Pro Tyr Gly Pro Gly Ser Ser Ala Ala Ala Ala Ala Ala Gly Ser
    355                 360                 365

Tyr Gly Pro Gly Val Leu Gly Pro Tyr Gly Pro Gly Pro Ser Ala Ala
    370                 375                 380

Ala Ala Ala Ala Ala Gly Ser Tyr Val Leu Gly Pro Gly Val Leu Gly
385                 390                 395                 400

Pro Tyr Gly Pro Gly Ala Ser Gly Pro Gly Val Leu Gly Pro Tyr Gly
            405                 410                 415

Pro Gly Ala Ser Ala Ala Ala Ala Ala Ala Gly Pro Gly Ile Tyr
            420                 425                 430

Gly Pro Gly Val Leu Gly Pro Ser Ala Ser Ala Ala Ala Ala Ala
            435                 440                 445

Ala Gly Ser Tyr Gly Ser Gly Pro Gly Ile Tyr Gly Pro Tyr Gly Pro
    450                 455                 460

Gly Ile Ser Gly Pro Gly Ser Gly Val Leu Gly Ile Gly Pro Tyr Gly
465                 470                 475                 480

Pro Gly Ala Ser Ala Ala Ala Ala Ala Ala Gly Ser Tyr Gly Pro
            485                 490                 495

Gly Val Leu Gly Pro Tyr Gly Pro Gly Ser Ala Ala Ala Ala Ala
            500                 505                 510

Ala Ala Gly Pro Gly Ser Gly Ile Tyr Gly Pro Gly Ala Ser Gly Ile
            515                 520                 525

Asn Gly Pro Gly Ser Gly Ile Tyr Gly Pro Gly Val Leu Gly Pro Gly
```

-continued

```
                    530                 535                 540
Pro Ser Ala Ala Ala Ala Ala Ala Gly Pro Gly Ser Gly Val Leu
545                 550                 555                 560

Gly Pro Gly Ala Ser
                565

<210> SEQ ID NO 40
<211> LENGTH: 576
<212> TYPE: PRT
<213> ORGANISM: Artificial Sequence
<220> FEATURE:
<223> OTHER INFORMATION: PRT699

<400> SEQUENCE: 40

Met His His His His His Ser Ser Gly Ser Gly Pro Gly Val
1               5                   10                  15

Leu Gly Pro Tyr Gly Pro Gly Ala Ser Ala Ala Ala Ala Ala Ala
                20                  25                  30

Gly Ser Asn Gly Pro Gly Ser Gly Val Leu Gly Pro Gln Ser Gly
                35                  40                  45

Gln Tyr Gly Pro Gly Val Leu Gly Pro Val Leu Gly Pro Gly Ser
50                  55                  60

Ser Ala Ala Ala Ala Ala Ala Gly Pro Gly Gln Tyr Gly Pro Gly
65                  70                  75                  80

Val Leu Gly Pro Ser Ala Ser Ala Ala Ala Ala Ala Ala Gly Pro
                85                  90                  95

Gly Ser Gly Val Leu Gly Pro Ala Ser Gly Gln Tyr Gly Pro Gly
                100                 105                 110

Val Leu Gly Pro Gly Val Leu Gly Pro Gly Ser Ser Ala Ala Ala
                115                 120                 125

Ala Ala Ala Gly Ser Tyr Gly Ser Gly Pro Gly Val Leu Gly Pro Tyr
                130                 135                 140

Gly Ser Ala Ala Ala Ala Ala Ala Gly Pro Gly Ser Gly Gln Tyr
145                 150                 155                 160

Gly Gln Gly Pro Tyr Gly Pro Gly Ala Ser Gly Pro Gly Gln Tyr Gly
                165                 170                 175

Pro Gly Val Leu Gly Pro Ser Ala Ser Ala Ala Ala Ala Ala Ala
                180                 185                 190

Gly Ser Gly Val Leu Gly Pro Gly Gln Tyr Gly Pro Tyr Ala Ser Ala
                195                 200                 205

Ala Ala Ala Ala Ala Gly Ser Tyr Gly Ser Gly Pro Gly Val Leu
                210                 215                 220

Gly Pro Tyr Gly Pro Gly Gln Ser Gly Ser Gly Val Leu Gly Pro Gly
225                 230                 235                 240

Val Leu Gly Pro Tyr Ala Ser Ala Ala Ala Ala Ala Ala Gly Pro
                245                 250                 255

Gly Val Leu Gly Pro Tyr Gly Pro Gly Ser Ser Ala Ala Ala Ala
                260                 265                 270

Ala Ala Gly Ser Tyr Gly Tyr Gly Pro Gly Val Leu Gly Pro Tyr Gly
                275                 280                 285

Pro Gly Ala Ser Gly Gln Asn Gly Pro Gly Ser Gly Gln Tyr Gly Pro
                290                 295                 300

Gly Val Leu Gly Pro Gly Pro Ser Ala Ala Ala Ala Ala Ala Gly
305                 310                 315                 320

Pro Gly Val Leu Gly Pro Tyr Gly Pro Gly Ala Ser Ala Ala Ala Ala
```

-continued

```
                325                 330                 335
Ala Ala Ala Gly Ser Tyr Gly Pro Gly Val Leu Gly Pro Gly Gln Tyr
            340                 345                 350
Gly Pro Gly Ser Ser Gly Pro Gly Val Leu Gly Pro Tyr Gly Pro Gly
            355                 360                 365
Ser Ser Ala Ala Ala Ala Ala Ala Gly Ser Tyr Gly Pro Gly Val
        370                 375                 380
Leu Gly Pro Tyr Gly Pro Gly Pro Ser Ala Ala Ala Ala Ala Ala
385                 390                 395                 400
Gly Ser Tyr Val Leu Gly Pro Gly Val Leu Gly Pro Tyr Gly Pro Gly
            405                 410                 415
Ala Ser Gly Pro Gly Val Leu Gly Pro Tyr Gly Pro Gly Ala Ser Ala
            420                 425                 430
Ala Ala Ala Ala Ala Ala Gly Pro Gly Gln Tyr Gly Pro Gly Val Leu
        435                 440                 445
Gly Pro Ser Ala Ser Ala Ala Ala Ala Ala Gly Ser Tyr Gly
450                 455                 460
Ser Gly Pro Gly Gln Tyr Gly Pro Tyr Gly Pro Gly Gln Ser Gly Pro
465                 470                 475                 480
Gly Ser Gly Val Leu Gly Gln Gly Pro Tyr Gly Pro Gly Ala Ser Ala
            485                 490                 495
Ala Ala Ala Ala Ala Gly Ser Tyr Gly Pro Gly Val Leu Gly Pro
        500                 505                 510
Tyr Gly Pro Gly Pro Ser Ala Ala Ala Ala Ala Gly Pro Gly
            515                 520                 525
Ser Gly Gln Tyr Gly Pro Gly Ala Ser Gly Gln Asn Gly Pro Gly Ser
        530                 535                 540
Gly Gln Tyr Gly Pro Gly Val Leu Gly Pro Gly Pro Ser Ala Ala Ala
545                 550                 555                 560
Ala Ala Ala Ala Gly Pro Gly Ser Gly Val Leu Gly Pro Gly Ala Ser
            565                 570                 575
```

<210> SEQ ID NO 41
<211> LENGTH: 576
<212> TYPE: PRT
<213> ORGANISM: Artificial Sequence
<220> FEATURE:
<223> OTHER INFORMATION: PRT698

<400> SEQUENCE: 41

```
Met His His His His His Ser Ser Gly Ser Gly Pro Gly Val
1               5                   10                  15
Leu Gly Pro Tyr Gly Pro Gly Ala Ser Ala Ala Ala Ala Ala Ala
            20                  25                  30
Gly Ser Asn Gly Pro Gly Ser Gly Val Leu Gly Pro Gly Ile Ser Gly
        35                  40                  45
Ile Tyr Gly Pro Gly Val Leu Gly Pro Gly Val Leu Gly Pro Gly Ser
    50                  55                  60
Ser Ala Ala Ala Ala Ala Ala Ala Gly Pro Gly Ile Tyr Gly Pro Gly
65                  70                  75                  80
Val Leu Gly Pro Ser Ala Ser Ala Ala Ala Ala Ala Gly Pro
            85                  90                  95
Gly Ser Gly Val Leu Gly Pro Gly Ala Ser Gly Ile Tyr Gly Pro Gly
            100                 105                 110
Val Leu Gly Pro Gly Val Leu Gly Pro Gly Ser Ser Ala Ala Ala Ala
```

```
            115                 120                 125
Ala Ala Ala Gly Ser Tyr Gly Ser Gly Pro Gly Val Leu Gly Pro Tyr
    130                 135                 140
Gly Ser Ala Ala Ala Ala Ala Ala Gly Pro Gly Ser Gly Ile Tyr
145                 150                 155                 160
Gly Ile Gly Pro Tyr Gly Pro Gly Ala Ser Gly Pro Gly Ile Tyr Gly
                165                 170                 175
Pro Gly Val Leu Gly Pro Ser Ser Ala Ala Ala Ala Ala Ala
                180                 185                 190
Gly Ser Gly Val Leu Gly Pro Gly Ile Tyr Gly Pro Tyr Ala Ser Ala
                195                 200                 205
Ala Ala Ala Ala Ala Gly Ser Tyr Gly Ser Gly Pro Gly Val Leu
    210                 215                 220
Gly Pro Tyr Gly Pro Gly Ile Ser Gly Ser Gly Val Leu Gly Pro Gly
225                 230                 235                 240
Val Leu Gly Pro Tyr Ala Ser Ala Ala Ala Ala Ala Ala Gly Pro
                245                 250                 255
Gly Val Leu Gly Pro Tyr Gly Pro Gly Ser Ser Ala Ala Ala Ala
                260                 265                 270
Ala Ala Gly Ser Tyr Gly Tyr Gly Pro Gly Val Leu Gly Pro Tyr Gly
    275                 280                 285
Pro Gly Ala Ser Gly Ile Asn Gly Pro Gly Ser Gly Ile Tyr Gly Pro
                290                 295                 300
Gly Val Leu Gly Pro Gly Pro Ser Ala Ala Ala Ala Ala Ala Gly
305                 310                 315                 320
Pro Gly Val Leu Gly Pro Tyr Gly Pro Gly Ala Ser Ala Ala Ala
                325                 330                 335
Ala Ala Ala Gly Ser Tyr Gly Pro Gly Val Leu Gly Pro Gly Ile Tyr
    340                 345                 350
Gly Pro Gly Ser Ser Gly Pro Gly Val Leu Gly Pro Tyr Gly Pro Gly
                355                 360                 365
Ser Ser Ala Ala Ala Ala Ala Ala Gly Ser Tyr Gly Pro Gly Val
    370                 375                 380
Leu Gly Pro Tyr Gly Pro Gly Pro Ser Ala Ala Ala Ala Ala Ala
385                 390                 395                 400
Gly Ser Tyr Val Leu Gly Pro Gly Val Leu Gly Pro Tyr Gly Pro Gly
                405                 410                 415
Ala Ser Gly Pro Gly Val Leu Gly Pro Tyr Gly Pro Gly Ala Ser Ala
                420                 425                 430
Ala Ala Ala Ala Ala Gly Pro Gly Ile Tyr Gly Pro Gly Val Leu
    435                 440                 445
Gly Pro Ser Ala Ser Ala Ala Ala Ala Ala Gly Ser Tyr Gly
    450                 455                 460
Ser Gly Pro Gly Ile Tyr Gly Pro Tyr Gly Pro Gly Ile Ser Gly Pro
465                 470                 475                 480
Gly Ser Gly Val Leu Gly Ile Gly Pro Tyr Gly Pro Gly Ala Ser Ala
                485                 490                 495
Ala Ala Ala Ala Ala Gly Ser Tyr Gly Pro Gly Val Leu Gly Pro
    500                 505                 510
Tyr Gly Pro Gly Pro Ser Ala Ala Ala Ala Ala Ala Gly Pro Gly
    515                 520                 525
Ser Gly Ile Tyr Gly Pro Gly Ala Ser Gly Ile Asn Gly Pro Gly Ser
                530                 535                 540
```

```
Gly Ile Tyr Gly Pro Gly Val Leu Gly Pro Gly Pro Ser Ala Ala Ala
545                 550                 555             560

Ala Ala Ala Ala Gly Pro Gly Ser Gly Val Leu Gly Pro Gly Ala Ser
                565             570             575
```